United States Patent
Mukhopadhyay et al.

(10) Patent No.: US 10,513,713 B2
(45) Date of Patent: Dec. 24, 2019

(54) MODIFIED HOST CELLS HAVING TOLERANCE TO α-OLEFINS

(71) Applicants: The Regents of the University of California, Oakland, CA (US); Total Marketing Services, Puteaux (FR)

(72) Inventors: Aindrila Mukhopadhyay, Oakland, CA (US); Florence Mingardon, Emeryville, CA (US); Angelique Chanal, Paris (FR)

(73) Assignees: The Regents of the University of California, Oakland, CA (US); Total Marketing Services, Puteaux (FR)

( * ) Notice: Subject to any disclaimer, the term of this patent is extended or adjusted under 35 U.S.C. 154(b) by 0 days.

(21) Appl. No.: 15/307,783

(22) PCT Filed: Apr. 29, 2015

(86) PCT No.: PCT/US2015/028296
§ 371 (c)(1),
(2) Date: Oct. 28, 2016

(87) PCT Pub. No.: WO2015/168288
PCT Pub. Date: Nov. 5, 2015

(65) Prior Publication Data
US 2017/0051317 A1  Feb. 23, 2017

Related U.S. Application Data

(60) Provisional application No. 61/986,669, filed on Apr. 30, 2014.

(51) Int. Cl.
*C07K 14/245* (2006.01)
*C12P 5/02* (2006.01)

(52) U.S. Cl.
CPC ............ *C12P 5/026* (2013.01); *C07K 14/245* (2013.01)

(58) Field of Classification Search
CPC ................................ C12P 5/026; C07K 14/245
See application file for complete search history.

(56) References Cited

U.S. PATENT DOCUMENTS

| | | |
|---|---|---|
| 2005/0255538 A1 | 11/2005 | Buxser et al. |
| 2007/0099277 A1 | 5/2007 | Anderson et al. |
| 2011/0294183 A1 | 12/2011 | Dunlop et al. |
| 2013/0078686 A1 | 3/2013 | Holtzapple et al. |
| 2014/0093923 A1 | 4/2014 | Reppas et al. |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Schuster et al., Antimicrob. Agents Chemother. 58(11):6870-6878, Sep. 2, 2014.*
Bohnert, et al., "Site-Directed Mutagenesis Reveals Putative Substrate Binding Residues in the *Escherichia coli* RND Efflux Pump AcrB," Journal of Bacteriology 190(24):8225-8229 (2008).
Dunlop, et al., "Engineering microbial biofuel tolerance and export using efflux pumps," Molecular Systems Biology 7:487 (2011).
Eicher, et al., "Transport of drugs by the multidrug transporter AcrB involves an access and a deep binding pocket that are separated by a switch-loop," Proceedings of the National Academy of Sciencs of the United States of America 109(15):5687-92 (2012).
Fisher, et al., Enhancing Tolerance to Short-Chain Alcohols by Engineering the *Escherichia coli* AcrB Efflux Pump to Secrete the Non-native Substrate n-Butanol. ACS Synthetic Biology (2013).
Foo, et al. "Directed evolution of an *E. coli* inner membrane transporter for imporved efflux of biofuel molecules," Biotechnology for Biofuels 6(1):81 (2013).
Husain, et al.,"Vestibules are Part of the Substrate Path in the Multidrug Efflux Transporter AcrB of *Escherichia coli*," Journal of Bacteriology 193(2):5847-9 (2011).
Murakami, et al., "Crystal structure of bacterial multidrug efflux transporter AcrB," Nature 419(6907):587-93 (2002).
Murakami, et al., "Extramembrane Central Pore of Multidrug Exporter AcrB in *Escherichia coli* Plays an Important Role in Drug Transport," The Journal of Biological Chemistry 279(5):3743-8 (2004).
Su, et al., "Conformation of the AcrB Multidrug Efflux Pump in Mutants of the Putative Proton Relay Pathway," Journal of Bacteriology 188(2):7290-6 (2006).
Takatsuka, et al., "Mechanism of recognition of compounds of diverse structures by the multidrug efflux pump AcrB of *Escherichia coli*," Proceedings of the National Academy of Sciences of the United States of America 107(15):6559-65 (2010).
Takatsuka, et al., "Site-Directed Disulfide Cross-Linking Shows that Cleft Flexibility in the Periplasmic Domain is Needed for the Multidrug Efflux Pump AcrB of *Escherichia coli*," Journal of Bacteriology 189(23):8677-84 (2007).
Tikhonova, et al., "Sequential Mechanism of Assembly of Multidrug Efflux Pump AcrAB-TolC," Chemistry and Biology 18(4):454-63 (2011).
Vargiu, et al., "Multidrug binding properties of the AcrB efflux pump characterized by molecular dynamics simulations," Proceedings of the National Academy of Sciences of the United States of America 109(50):20637-42 (2012).
Wagner, et al., "Consequences of Membrane Protein Overexpression in *Escherichia coli*," Molecular & Cellular Proteomics : MCP 6(9): 1527-50 (2007).

(Continued)

*Primary Examiner* — Delia M Ramirez
(74) *Attorney, Agent, or Firm* — Kilpatrick Townsend & Stockton LLP

(57) ABSTRACT

The present invention provides methods for improving microbial tolerance to alpha olefin compounds, host cells having increased tolerance to such compounds, and method of using the host cells to produce alpha olefin compounds.

17 Claims, 11 Drawing Sheets
Specification includes a Sequence Listing.

(56) References Cited

OTHER PUBLICATIONS

Yu, et al., "AcrB Trimer Stability and Efflux Activity, Insight from Mutagenesis Studies," PLoS One 6(12):e28390 (2011).
PCT/US2015/28296 , "International Search Report and Written Opinion", dated Nov. 12, 2015, 7 pages.

* cited by examiner

```
                sequences alignments, illustrative AcrB domains

SEQ ID NO:1: AcrB E. coli
SEQ ID NO:2: Pseudomonas putida 66% identity with AcrB
SEQ ID NO:3: Marinobacter aqueolei 59% identity with AcrB
SEQ ID NO:4: Pseudoalteromonas haloplanktis 62% of identity with AcrB
SEQ ID NO:5: AcrF 78% of identity with AcrB Illustrative domain structures of SEQ ID NO:1:
transmembrane domains--highlighted
Italics, underlined, increased font size: illustrative mutations improving tolerance
Bolded, underlined: Amino acids important for binding
Underlined: Amino acids important for H+ transport SEQ ID NO:1  MPNFFIDRPI FAWVIAIIMLAGGLAILK LPVAQYPTIAPPAVTISASYPGADAKTVQDT    60
SEQ ID NO:2  M   FFIDRPIFAWVIA+++IML G L+ILKLP+ QYP+IAPPA+ I+ +YPGA A+TVQDT
SEQ ID NO:3  MP FFI+RPIFAWV+A+++ML GGLA+   L V  Q+P +APPA+ +S +YPGA A+TVQDT
SEQ ID NO:4  M  +FID+PIFAWV+AII+MLAG LA+   LP+AQYP+IAPPA++I+A+YPGA A+T++D+
SEQ ID NO:5  M NFFI RPIFAWV+AII+M+AG LAIL+LPVAQYPTIAPPAV++SA+YPGADA+TVQDT SEQ ID NO:1  VTQVIEQNMNGIDNLMYMSSNSDSTGTVQ ITLTFESGTDADI AQVQVQNKLQLAMPLLPQ   120
SEQ ID NO:2  V QVIEQ +NGIDNL Y+SS S+S G++ IT TFE GT+ D AQVQVQNKL LA PLLPQ
SEQ ID NO:3  V QVIEQ +NG+D L Y+SS S+S G++ I  TFE GTD DIAQVQVQNKLQLA PLLP+
SEQ ID NO:4  VTQVIEQ M G+D L+YMSS S+S G+  +TLTF + TD DIAQVQVQNKL  A PLLP+
SEQ ID NO:5  VTQVIEQNMNGIDNLMYMSS SDS G+V ITLTF+SGTD DIAQVQVQNKLQLA PLLPQ SEQ ID NO:1  EVQQGVSVEKSSSS FLMV VGVINTDGTMTQEDISDYVAANMKDAISRTSGVGDVQLFGS    180
SEQ ID NO:2  EVQQQG+ V K+  +FL+V+G+++  DG+MT++D+++Y+ +NM+D ISRT+GVGD Q+FG+
SEQ ID NO:3  EVQ+QG+ V K   +F  V  + +  DG  TQ D++DY+ +N++D ++RT GVGD  LFGS
SEQ ID NO:4  EVQ+QGV V K++ +FL+V+  ++  DG+MT  DI DYVA+N++D +SR  GVG+ QLFGS
SEQ ID NO:5  EVQQQG+SVEKSSSS+LMV G ++ +   TQ+DISDYVA+N+KD +SR +GVGDVQLFG+

FIG. 8
```

```
SEQ ID NO:1    QYAMRIWMNPNELNKFQLTPVDVITAIKAQNAQVAAGQLGGTPPVKGQQLNASIIAQTRL    240
SEQ ID NO:2    QYAMRIW++P +LNKFQLTPVDV TA+ AQN QV++GQLGG P + G QLNA+II +TRL
SEQ ID NO:3    QYAMR+W++P +LN +QLTP DVI +++AQN QV+AGQLGG P   +G QL A++I + R+
SEQ ID NO:4    QYAMRIW++P +L  F+LTP D+   AI AQNAQV+AGQLGG P + GQQLNA+I AQ+RL
SEQ ID NO:5    QYAMRIW++ + LNK++LTPVDVI   +K QN Q+AAGQLGGTP + GQQLNASIIAQTR

SEQ ID NO:1    TSTEEFGKILLKVNQDGSRVLLRDVAKIELGGENYDIAEFNGQPASGLGIKLATGANAL    300
SEQ ID NO:2     + E+F   ILLKVN+DGS+V L DVA++ LGGENY + A+FNG+PASGL +KLATGANAL
SEQ ID NO:3     + EEF   ILLKVN DGS+V L DVA++ LG ENY    ++NG PA+G+ ++LATGAN L
SEQ ID NO:4     + E+F   IL+K N DGS V L+DVA++ELGGENY ++A +NG PA+G+GIKLA+GANAL
SEQ ID NO:5     + EEFGK+ L+VN DGS V L+DVA++ELGGENY++IA   NG+PA+GLGIKLATGANAL

SEQ ID NO:1    DTAAAIRAELAKMEPFFPSGLKIVYPYDTTPFVKISIHEVVKTLVEAIILVFLVMYLFLQ    360
SEQ ID NO:2    DTA A+R    +  +EPFFP G+K V+PYDTTP V SI   V+  TL+EA++LVFLVMYLFLQ
SEQ ID NO:3    +TA    ++  LA++E F P G++IV+PYDTTP V SI   V    TL+EA++LVFLVM+LFLQ
SEQ ID NO:4    DTA    ++  L  ++PFFP GL +   PYDTTPFV +SI +VV TL+EA+ILVF+VMYLFLQ
SEQ ID NO:5    DTA AI+A+LA+++PFFP G+K++YPYDTTPFV++SIHEVVKTL EAI+LVFLVMYLFLQ

SEQ ID NO:1    NFRATLIPTIAVPVVLLGTFAVLAAFGFSINTLTMFGMVLAIGLLVDDAIVVENVERVM    420
SEQ ID NO:2    NFRAT+I T+ VPVVLLGTF +LAA GFSINTLTMF MVLAIGLLVDDAIVVENVERVM
SEQ ID NO:3    ++RAT+IPT+AVPVVLL TF VL AFGF+++N +TMF MVLAIGLLVDDAIVVENVER+M
SEQ ID NO:4    NFRATLIPTIAVPVVLLGTFA+L   FG+SINTLTMF MVLAIGLLVDDAIVVENVER+M
SEQ ID NO:5    N RATLIPTIAVPVVLLGTFA+LAAFG+SINTLTMFGMVLAIGLLVDDAIVVENVERVM

SEQ ID NO:1    AEEGLPPKEATRKSMGQIQGALVGIAMVLSAVFVPMAFFGGSTGAIYRQFSITIVSAMAL    480
SEQ ID NO:2    +EEGLPPKEAT++SM QIQGALVGIA+VLSAV +PMAFFGGSTG IYRQFSITIVSAM L
SEQ ID NO:3    EEGL PKEA +KSM QI GAL+GI +V+SAVF+PMAFFGGSTG IYRQFS+TI+SAM+
SEQ ID NO:4    EE  L   +ATRKSM +I+GALVGIAMVLSAVF+PMAFF GSTG  IYRQFSITIVSAM L
SEQ ID NO:5    E+ LPPKEAT KSM QIQGALVGIAMVLSAVF+PMAFFGGSTGAIYRQFSITIVSAMAL
```

FIG. 8 (Cont. 1)

```
SEQ ID NO:1  SVLVALILTPALCATMLKPIAKGDHGEGKKGFFGWFNRMFEKSTHHYTDSVGGILRSTGR  540
SEQ ID NO:2  SVLVALI TPALCATMLKP+ KG+H       K GFFGWFNR F++S + Y  SVG ILR+
SEQ ID NO:3  SVLVA I TPALCAT+LKP   GD      +KGFFGWFNR F++S    Y   V +++ GR
SEQ ID NO:4  SVLVALILTPALCAT+LKP    D         FF  FNR  F+K+         VG ++ + R
SEQ ID NO:5  SVLVALILTPALCAT+LKP++      +H E K GFFGWFN   F+ S +HYT+SVG IL STGR

SEQ ID NO:1  YLVLYLIIVVGMAYLFVRLPSSFLPDEDQGVFMTMVQLPAGATQERTQKVLNEVTHYYLT  600
SEQ ID NO:2  +L+ Y +IVVGM +LF R+P++FLP+EDQGV       VQ PAG++ ERTQ V+++++ Y L
SEQ ID NO:3  ++ +YL++VV + +LF   LP++FLPDEDQGV + MVQLP AT ERT+ VL E  +Y L
SEQ ID NO:4  YL++Y ++V GM Y+F   LP++FLPDEDQG+        V LPAG+T E+T  V+ +V ++YL
SEQ ID NO:5  YL++Y +IV GM   LF+RLPSSFLP+EDQGVF+TM+QLPAGATQERTQKVL++VT YYL

SEQ ID NO:1  KEKNNVESVFAVNGFGFAGRQNTGIAFVSLKDWADRPGEENKVEAITMRATRAFSQIKD  660
SEQ ID NO:2  E + V SVF VNGF  FAGRGQ++G+AF+ LK W +R  +EN V A+  RA + F  +D
SEQ ID NO:3  +E    V+SV +V GF FAGRGQN+GI FV LK +ADR      V A+  R+    F+QIKD
SEQ ID NO:4  +    V S+F V GF FAG GQN+ I FV+LK W +R   ++  V A+   +   FS IK+
SEQ ID NO:5  EK NVESVF VNGF F+G+ QN G+AFVSLK W +R G+EN  EA+  RA       +I+D

SEQ ID NO:1  AMVFAFNLPAIVELGTATGFDFELIDQAGLGHEKLTQARNQLLAEAAKHPDMLTSVRPNG  720
SEQ ID NO:2  AMVFAF   PA++ELG ATGFD  L D+ G+GHEKL +ARNQ LA+AA+       +L++VRPNG
SEQ ID NO:3  A+VF     PAI+ELG ATGFD  L D   +GH   L  A N+ ++ A    P+ L  VR NG
SEQ ID NO:4  A VFAF   PAIVELGTA GF+   L D+ GLGH++L   ARN LL   A+K P +L  VRPNG
SEQ ID NO:5  V   FN+PAIVELGTATGFDFELIDQAGLGH+ LTQARNQLL    AA+HP  L SVRPNG

SEQ ID NO:1  LEDTPQFKIDIDQEKAQALGVSINDINTTLGAAWGGSYVNDFIDRGRVKKVYVMSEAKYR  780
SEQ ID NO:2  L D PQ+++ ID E+A ALGV+I DIN TL  A G  SYVNDFIDRGRVKKVY+  E   R
SEQ ID NO:3  L D PQ+++ ID EKA+ L VSI DIN T+ AAWG SYVNDF+  GRVKKVYV     R
SEQ ID NO:4  ED P+ ++DID   KA+ALGV+    DIN+TL  AWG   YVNDFIDRGRVKKVY+  EA  R
SEQ ID NO:5  LEDT QFK+++DQEKAQALGVS++DIN T+     A GG+YVNDFIDRGRVKK+YV ++AK+R
```

FIG. 8 (Cont. 2)

```
SEQ ID NO:1   MLPDDIGDWYVRAADGQMVPFSAFSSSRWEYGSPRLERYNGLPSMEILGQAAPGKSTGEA   840
SEQ ID NO:2   M P+D+   WYVR   G+MVPFS+F+    W  YGSP+L RYNG+ +MEILG  APG STGEA
SEQ ID NO:3    + P+D   W+VR  A G+MVPF+AF++   W +GSPRL+RY GLP+ +I G   A G STG+A
SEQ ID NO:4   M+P+D+   WYVR   +G MVPF+AF+SS  W YGSPRLERYNG   +MEI G AAPG STG+A
SEQ ID NO:5   MLP+D+   YVR+A+G+MVPFSAF++S  W YGSPRLERYNGLPSMEI G+AAPG S+G+A

SEQ ID NO:1   MELMEQLASKLPTGVGYDWTGMSYQERLSGNQAPSLYAISLIVVFLCLAALYESWSIPFS   900
SEQ ID NO:2   M    +E++A +LP+G+G+  WTGMSY+E+LSG+Q P+L+A+S++ VFLCLAALYESWSIP +
SEQ ID NO:3   M    +E++A+ LP G+G  ++TG+S++E+ +GNQA    LY +S++VVFLCLAALYESWSIPF+
SEQ ID NO:4   M+ ME+L   +LP G+   +W+G+SYQER SG QAP LY +SL+ VFLCLAALYESWS+PF+
SEQ ID NO:5   M LME LASKLP G+GYDWTGMSYQERLSGNQAP+L AIS +VVFLCLAALYESWSIP S

SEQ ID NO:1   VMLVVPLGVIGALLAATFRGLTNDVYFQVGLLTTIGLSAKNAILIVEFAKDLMDKEGKGL   960
SEQ ID NO:2   V+LVVPLG+IGAL+A + RGL+NDVYF VGLLTTIGL+AKNAILIVEFAK+L  ++G+ L
SEQ ID NO:3   V+++VPLGV+GA+LA    RGL+NDV+FQVG+LTT+GL+AKNAILIVEFA+  L  ++EGK L
SEQ ID NO:4   VM++VPLG+ GA++AA      L+ND+Y QVGLLTTIGL++KNAILIVEFA    M+ EG   L
SEQ ID NO:5   VMLVVPLG++G LLAAT        NDVYF VGLLTTIGLSAKNAILIVEFAKDLM+KEGKG+

SEQ ID NO:1   IEATLDAVRMRLRPILMTSLAFILGVMPLVISTGAGSGAQNAVGTGVMGGMVTATVLAIF   1020
SEQ ID NO:2    +A ++A RMRLRPI+MTSLAFILGV+PL I++GAG+G+Q+A+GTGV+GGM++ATVLAIF
SEQ ID NO:3   ++AT +A R+RLRPI+MTSLAFI GV+P+ I++GA S  +Q+A+GT V+GG +  AT+LAIF
SEQ ID NO:4   ++A +  AV++RLRP+LMTSLAFI GV+PL I++ AGSGAQNA+G   ++GG  + A+  L +
SEQ ID NO:5   +EATL AVRMRLRPILMTSLAFILGV+PL IS GAGSGAQNAVG GVMGGMV+AT+LAIF

SEQ ID NO:1   FVPVFFVVVRRRFSRKNEDIEHSHTVDHH   1049
SEQ ID NO:2   +VP+FFV V   F   K   +
SEQ ID NO:3   FVP+F+V VV    RK+ D
SEQ ID NO:4   FVP+FFV+VR+ FS K+
SEQ ID NO:5   FVPVFFVV+RR F
```

FIG. 8 (Cont. 3)

SEQUENCE LISTING

<160> NUMBER OF SEQ ID NOS: 33

<210> SEQ ID NO 1
<211> LENGTH: 1049
<212> TYPE: PRT
<213> ORGANISM: E. coli

<400> SEQUENCE: 1

Met Pro Asn Phe Phe Ile Asp Arg Pro Ile Phe Ala Trp Val Ile Ala
1               5                   10                  15

-continued

Ile Ile Ile Met Leu Ala Gly Gly Leu Ala Ile Leu Lys Leu Pro Val
            20                  25                  30

Ala Gln Tyr Pro Thr Ile Ala Pro Ala Val Thr Ile Ser Ala Ser
        35                  40                  45

Tyr Pro Gly Ala Asp Ala Lys Thr Val Gln Asp Thr Val Thr Gln Val
    50                  55                  60

Ile Glu Gln Asn Met Asn Gly Ile Asp Asn Leu Met Tyr Met Ser Ser
65                  70                  75                  80

Asn Ser Asp Ser Thr Gly Thr Val Gln Ile Thr Leu Thr Phe Glu Ser
                85                  90                  95

Gly Thr Asp Ala Asp Ile Ala Gln Val Gln Val Gln Asn Lys Leu Gln
                100                 105                 110

Leu Ala Met Pro Leu Leu Pro Gln Glu Val Gln Gln Gln Gly Val Ser
                115                 120                 125

Val Glu Lys Ser Ser Ser Ser Phe Leu Met Val Val Gly Val Ile Asn
130                 135                 140

Thr Asp Gly Thr Met Thr Gln Glu Asp Ile Ser Asp Tyr Val Ala Ala
145                 150                 155                 160

Asn Met Lys Asp Ala Ile Ser Arg Thr Ser Gly Val Gly Asp Val Gln
                165                 170                 175

Leu Phe Gly Ser Gln Tyr Ala Met Arg Ile Trp Met Asn Pro Asn Glu
                180                 185                 190

Leu Asn Lys Phe Gln Leu Thr Pro Val Asp Val Ile Thr Ala Ile Lys
                195                 200                 205

Ala Gln Asn Ala Gln Val Ala Ala Gly Gln Leu Gly Gly Thr Pro Pro
                210                 215                 220

Val Lys Gly Gln Gln Leu Asn Ala Ser Ile Ile Ala Gln Thr Arg Leu
225                 230                 235                 240

Thr Ser Thr Glu Glu Phe Gly Lys Ile Leu Leu Lys Val Asn Gln Asp
                245                 250                 255

Gly Ser Arg Val Leu Leu Arg Asp Val Ala Lys Ile Glu Leu Gly Gly
                260                 265                 270

Glu Asn Tyr Asp Ile Ile Ala Glu Phe Asn Gly Gln Pro Ala Ser Gly
                275                 280                 285

Leu Gly Ile Lys Leu Ala Thr Gly Ala Asn Ala Leu Asp Thr Ala Ala
                290                 295                 300

Ala Ile Arg Ala Glu Leu Ala Lys Met Glu Pro Phe Phe Pro Ser Gly
305                 310                 315                 320

Leu Lys Ile Val Tyr Pro Tyr Asp Thr Thr Pro Phe Val Lys Ile Ser
                325                 330                 335

Ile His Glu Val Val Lys Thr Leu Val Glu Ala Ile Ile Leu Val Phe
                340                 345                 350

Leu Val Met Tyr Leu Phe Leu Gln Asn Phe Arg Ala Thr Leu Ile Pro
                355                 360                 365

Thr Ile Ala Val Pro Val Val Leu Leu Gly Thr Phe Ala Val Leu Ala
                370                 375                 380

Ala Phe Gly Phe Ser Ile Asn Thr Leu Thr Met Phe Gly Met Val Leu
385                 390                 395                 400

Ala Ile Gly Leu Leu Val Asp Asp Ala Ile Val Val Glu Asn Val
                405                 410                 415

Glu Arg Val Met Ala Glu Glu Gly Leu Pro Pro Lys Glu Ala Thr Arg
                420                 425                 430

```
Lys Ser Met Gly Gln Ile Gln Gly Ala Leu Val Gly Ile Ala Met Val
            435                 440                 445

Leu Ser Ala Val Phe Val Pro Met Ala Phe Gly Gly Ser Thr Gly
450                 455                 460

Ala Ile Tyr Arg Gln Phe Ser Ile Thr Ile Val Ser Ala Met Ala Leu
465                 470                 475                 480

Ser Val Leu Val Ala Leu Ile Leu Thr Pro Ala Leu Cys Ala Thr Met
                485                 490                 495

Leu Lys Pro Ile Ala Lys Gly Asp His Gly Glu Gly Lys Lys Gly Phe
            500                 505                 510

Phe Gly Trp Phe Asn Arg Met Phe Glu Lys Ser Thr His His Tyr Thr
            515                 520                 525

Asp Ser Val Gly Gly Ile Leu Arg Ser Thr Gly Arg Tyr Leu Val Leu
            530                 535                 540

Tyr Leu Ile Ile Val Val Gly Met Ala Tyr Leu Phe Val Arg Leu Pro
545                 550                 555                 560

Ser Ser Phe Leu Pro Asp Glu Asp Gln Gly Val Phe Met Thr Met Val
                565                 570                 575

Gln Leu Pro Ala Gly Ala Thr Gln Glu Arg Thr Gln Lys Val Leu Asn
            580                 585                 590

Glu Val Thr His Tyr Tyr Leu Thr Lys Glu Lys Asn Asn Val Glu Ser
            595                 600                 605

Val Phe Ala Val Asn Gly Phe Gly Phe Ala Gly Arg Gly Gln Asn Thr
            610                 615                 620

Gly Ile Ala Phe Val Ser Leu Lys Asp Trp Ala Asp Arg Pro Gly Glu
625                 630                 635                 640

Glu Asn Lys Val Glu Ala Ile Thr Met Arg Ala Thr Arg Ala Phe Ser
                645                 650                 655

Gln Ile Lys Asp Ala Met Val Phe Ala Phe Asn Leu Pro Ala Ile Val
            660                 665                 670

Glu Leu Gly Thr Ala Thr Gly Phe Asp Phe Glu Leu Ile Asp Gln Ala
            675                 680                 685

Gly Leu Gly His Glu Lys Leu Thr Gln Ala Arg Asn Gln Leu Leu Ala
            690                 695                 700

Glu Ala Ala Lys His Pro Asp Met Leu Thr Ser Val Arg Pro Asn Gly
705                 710                 715                 720

Leu Glu Asp Thr Pro Gln Phe Lys Ile Asp Ile Asp Gln Glu Lys Ala
                725                 730                 735

Gln Ala Leu Gly Val Ser Ile Asn Asp Ile Asn Thr Thr Leu Gly Ala
            740                 745                 750

Ala Trp Gly Gly Ser Tyr Val Asn Asp Phe Ile Asp Arg Gly Arg Val
            755                 760                 765

Lys Lys Val Tyr Val Met Ser Glu Ala Lys Tyr Arg Met Leu Pro Asp
770                 775                 780

Asp Ile Gly Asp Trp Tyr Val Arg Ala Ala Asp Gly Gln Met Val Pro
785                 790                 795                 800

Phe Ser Ala Phe Ser Ser Arg Trp Glu Tyr Gly Ser Pro Arg Leu
                805                 810                 815

Glu Arg Tyr Asn Gly Leu Pro Ser Met Glu Ile Leu Gly Gln Ala Ala
                820                 825                 830

Pro Gly Lys Ser Thr Gly Glu Ala Met Glu Leu Met Glu Gln Leu Ala
            835                 840                 845

Ser Lys Leu Pro Thr Gly Val Gly Tyr Asp Trp Thr Gly Met Ser Tyr
```

```
              850                 855                 860
Gln Glu Arg Leu Ser Gly Asn Gln Ala Pro Ser Leu Tyr Ala Ile Ser
865                 870                 875                 880

Leu Ile Val Val Phe Leu Cys Leu Ala Ala Leu Tyr Glu Ser Trp Ser
                885                 890                 895

Ile Pro Phe Ser Val Met Leu Val Val Pro Leu Gly Val Ile Gly Ala
                900                 905                 910

Leu Leu Ala Ala Thr Phe Arg Gly Leu Thr Asn Asp Val Tyr Phe Gln
                915                 920                 925

Val Gly Leu Leu Thr Thr Ile Gly Leu Ser Ala Lys Asn Ala Ile Leu
        930                 935                 940

Ile Val Glu Phe Ala Lys Asp Leu Met Asp Lys Glu Gly Lys Gly Leu
945                 950                 955                 960

Ile Glu Ala Thr Leu Asp Ala Val Arg Met Arg Leu Arg Pro Ile Leu
                965                 970                 975

Met Thr Ser Leu Ala Phe Ile Leu Gly Val Met Pro Leu Val Ile Ser
                980                 985                 990

Thr Gly Ala Gly Ser Gly Ala Gln Asn Ala Val Gly Thr Gly Val Met
        995                 1000                1005

Gly Gly Met Val Thr Ala Thr Val Leu Ala Ile Phe  Phe Val Pro
        1010                1015                1020

Val Phe  Phe Val Val Arg  Arg Arg Phe Ser Arg  Lys Asn Glu
        1025                1030                1035

Asp Ile  Glu His Ser His Thr  Val Asp His His
        1040                1045
```

<210> SEQ ID NO 2
<211> LENGTH: 1050
<212> TYPE: PRT
<213> ORGANISM: Pseudomonas putida

<400> SEQUENCE: 2

```
Met Ser Lys Phe Phe Ile Asp Arg Pro Ile Phe Ala Trp Val Ile Ala
1               5                   10                  15

Leu Val Ile Met Leu Val Gly Ala Leu Ser Ile Leu Lys Leu Pro Ile
                20                  25                  30

Asn Gln Tyr Pro Ser Ile Ala Pro Pro Ala Ile Ala Ile Ala Val Thr
                35                  40                  45

Tyr Pro Gly Ala Ser Ala Gln Thr Val Gln Asp Thr Val Val Gln Val
        50                  55                  60

Ile Glu Gln Gln Leu Asn Gly Ile Asp Asn Leu Arg Tyr Val Ser Ser
65                  70                  75                  80

Glu Ser Asn Ser Asp Gly Ser Met Thr Ile Thr Ala Thr Phe Glu Gln
                85                  90                  95

Gly Thr Asn Pro Asp Thr Ala Gln Val Gln Val Gln Asn Lys Leu Asn
                100                 105                 110

Leu Ala Thr Pro Leu Leu Pro Gln Glu Val Gln Gln Gln Gly Ile Arg
        115                 120                 125

Val Thr Lys Ala Val Lys Asn Phe Leu Leu Val Ile Gly Leu Val Ser
        130                 135                 140

Glu Asp Gly Ser Met Thr Lys Asp Asp Leu Ala Asn Tyr Ile Val Ser
145                 150                 155                 160

Asn Met Gln Asp Pro Ile Ser Arg Thr Ala Gly Val Gly Asp Phe Gln
                165                 170                 175
```

```
Val Phe Gly Ala Gln Tyr Ala Met Arg Ile Trp Leu Asp Pro Ala Lys
                180                 185                 190

Leu Asn Lys Phe Gln Leu Thr Pro Val Asp Val Lys Thr Ala Val Ala
            195                 200                 205

Ala Gln Asn Val Gln Val Ser Ser Gly Gln Leu Gly Gly Leu Pro Ala
        210                 215                 220

Leu Pro Gly Thr Gln Leu Asn Ala Thr Ile Ile Gly Lys Thr Arg Leu
225                 230                 235                 240

Gln Thr Ala Glu Gln Phe Glu Ser Ile Leu Leu Lys Val Asn Lys Asp
                245                 250                 255

Gly Ser Gln Val Arg Leu Gly Asp Val Ala Gln Val Gly Leu Gly Gly
            260                 265                 270

Glu Asn Tyr Ala Val Ser Ala Gln Phe Asn Gly Lys Pro Ala Ser Gly
        275                 280                 285

Leu Ala Val Lys Leu Ala Thr Gly Ala Asn Ala Leu Asp Thr Ala Lys
290                 295                 300

Ala Leu Arg Glu Thr Ile Lys Gly Leu Glu Pro Phe Phe Pro Pro Gly
305                 310                 315                 320

Val Lys Ala Val Phe Pro Tyr Asp Thr Thr Pro Val Val Thr Glu Ser
                325                 330                 335

Ile Ser Gly Val Ile His Thr Leu Ile Glu Ala Val Val Leu Val Phe
            340                 345                 350

Leu Val Met Tyr Leu Phe Leu Gln Asn Phe Arg Ala Thr Ile Ile Thr
        355                 360                 365

Thr Met Thr Val Pro Val Val Leu Leu Gly Thr Phe Gly Ile Leu Ala
370                 375                 380

Ala Ala Gly Phe Ser Ile Asn Thr Leu Thr Met Phe Ala Met Val Leu
385                 390                 395                 400

Ala Ile Gly Leu Leu Val Asp Asp Ala Ile Val Val Glu Asn Val
                405                 410                 415

Glu Arg Val Met Ser Glu Glu Gly Leu Pro Pro Lys Glu Ala Thr Lys
            420                 425                 430

Arg Ser Met Glu Gln Ile Gln Gly Ala Leu Val Gly Ile Ala Leu Val
        435                 440                 445

Leu Ser Ala Val Leu Leu Pro Met Ala Phe Phe Gly Gly Ser Thr Gly
450                 455                 460

Val Ile Tyr Arg Gln Phe Ser Ile Thr Ile Val Ser Ala Met Gly Leu
465                 470                 475                 480

Ser Val Leu Val Ala Leu Ile Phe Thr Pro Ala Leu Cys Ala Thr Met
                485                 490                 495

Leu Lys Pro Leu Lys Lys Gly Glu His His Thr Ala Lys Gly Gly Phe
            500                 505                 510

Phe Gly Trp Phe Asn Arg Asn Phe Asp Arg Ser Val Asn Gly Tyr Glu
        515                 520                 525

Arg Ser Val Gly Ala Ile Leu Arg Asn Lys Val Pro Phe Leu Leu Ala
530                 535                 540

Tyr Ala Leu Ile Val Val Gly Met Ile Trp Leu Phe Ala Arg Ile Pro
545                 550                 555                 560

Thr Ala Phe Leu Pro Glu Glu Asp Gln Gly Val Leu Phe Ala Gln Val
                565                 570                 575

Gln Thr Pro Ala Gly Ser Ser Ala Glu Arg Thr Gln Val Val Asp
            580                 585                 590

Gln Met Arg Glu Tyr Leu Leu Lys Asp Glu Ala Asp Thr Val Ser Ser
```

-continued

```
            595                 600                 605
Val Phe Thr Val Asn Gly Phe Asn Phe Ala Gly Arg Gly Gln Ser Ser
610                 615                 620

Gly Met Ala Phe Ile Met Leu Lys Pro Trp Asp Glu Arg Ser Lys Glu
625                 630                 635                 640

Asn Ser Val Phe Ala Leu Ala Gln Arg Ala Gln His Phe Phe Thr
                    645                 650                 655

Phe Arg Asp Ala Met Val Phe Ala Pro Pro Ala Val Leu Glu
                660                 665                 670

Leu Gly Asn Ala Thr Gly Phe Asp Val Phe Leu Gln Asp Arg Gly Gly
                675                 680                 685

Val Gly His Glu Lys Leu Met Glu Ala Arg Asn Gln Phe Leu Ala Lys
            690                 695                 700

Ala Ala Gln Ser Lys Ile Leu Ser Ala Val Arg Pro Asn Gly Leu Asn
705                 710                 715                 720

Asp Glu Pro Gln Tyr Gln Leu Thr Ile Asp Asp Glu Arg Ala Ser Ala
                    725                 730                 735

Leu Gly Val Thr Ile Ala Asp Ile Asn Asn Thr Leu Ser Ile Ala Leu
                740                 745                 750

Gly Ala Ser Tyr Val Asn Asp Phe Ile Asp Arg Gly Arg Val Lys Lys
            755                 760                 765

Val Tyr Ile Gln Gly Glu Pro Ser Ala Arg Met Ser Pro Glu Asp Leu
770                 775                 780

Gln Lys Trp Tyr Val Arg Asn Gly Ala Gly Glu Met Val Pro Phe Ser
785                 790                 795                 800

Ser Phe Ala Lys Gly Glu Trp Thr Tyr Gly Ser Pro Lys Leu Ser Arg
                805                 810                 815

Tyr Asn Gly Val Glu Ala Met Glu Ile Leu Gly Ala Pro Ala Pro Gly
                820                 825                 830

Tyr Ser Thr Gly Glu Ala Met Ala Glu Val Glu Arg Ile Ala Gly Glu
            835                 840                 845

Leu Pro Ser Gly Ile Gly Phe Ser Trp Thr Gly Met Ser Tyr Glu Glu
850                 855                 860

Lys Leu Ser Gly Ser Gln Met Pro Ala Leu Phe Ala Leu Ser Val Leu
865                 870                 875                 880

Phe Val Phe Leu Cys Leu Ala Ala Leu Tyr Glu Ser Trp Ser Ile Pro
                885                 890                 895

Ile Ala Val Val Leu Val Val Pro Leu Gly Ile Ile Gly Ala Leu Ile
                900                 905                 910

Ala Thr Ser Leu Arg Gly Leu Ser Asn Asp Val Tyr Phe Leu Val Gly
            915                 920                 925

Leu Leu Thr Thr Ile Gly Leu Ala Ala Lys Asn Ala Ile Leu Ile Val
            930                 935                 940

Glu Phe Ala Lys Glu Leu His Glu Gln Gly Arg Ser Leu Tyr Asp Ala
945                 950                 955                 960

Ala Ile Glu Ala Cys Arg Met Arg Leu Arg Pro Ile Ile Met Thr Ser
                965                 970                 975

Leu Ala Phe Ile Leu Gly Val Val Pro Leu Thr Ile Ala Ser Gly Ala
                980                 985                 990

Gly Ala Gly Ser Gln His Ala Ile Gly Thr Gly Val Ile Gly Gly Met
            995                 1000                1005

Ile Ser Ala Thr Val Leu Ala Ile Phe Trp Val Pro Leu Phe Phe
        1010                1015                1020
```

```
Val Ala Val Ser Ser Leu Phe Gly Ser Lys Glu Pro Glu Lys Asp
    1025                1030                1035

Val Thr Pro Glu Asn Pro Arg Tyr Glu Ala Gly Gln
    1040                1045                1050
```

<210> SEQ ID NO 3
<211> LENGTH: 1036
<212> TYPE: PRT
<213> ORGANISM: Marinobacter aqueolei

<400> SEQUENCE: 3

```
Met Pro Arg Phe Phe Ile Glu Arg Pro Ile Phe Ala Trp Val Val Ala
1               5                   10                  15

Leu Met Leu Met Leu Gly Gly Gly Leu Ala Val Lys Asn Leu Ala Val
            20                  25                  30

Asn Gln Phe Pro Asp Val Ala Pro Pro Ala Ile Ala Leu Ser Val Asn
        35                  40                  45

Tyr Pro Gly Ala Ser Ala Gln Thr Val Gln Asp Thr Val Val Gln Val
    50                  55                  60

Ile Glu Gln Gln Leu Asn Gly Leu Asp Gly Leu Arg Tyr Ile Ser Ser
65                  70                  75                  80

Glu Ser Asn Ser Asp Gly Ser Met Thr Ile Ile Ala Thr Phe Glu Gln
                85                  90                  95

Gly Thr Asp Pro Asp Ile Ala Gln Val Gln Val Gln Asn Lys Leu Gln
            100                 105                 110

Leu Ala Asn Pro Leu Leu Pro Glu Glu Val Gln Arg Gln Gly Ile Arg
        115                 120                 125

Val Ser Lys Tyr Lys Val Asn Phe Phe Thr Val Phe Ala Leu Thr Ser
    130                 135                 140

Pro Asp Gly Lys Tyr Thr Gln Gly Asp Leu Ala Asp Tyr Ile Val Ser
145                 150                 155                 160

Asn Ile Gln Asp Pro Val Ala Arg Thr Gln Gly Val Gly Asp Phe Leu
                165                 170                 175

Leu Phe Gly Ser Gln Tyr Ala Met Arg Leu Trp Leu Asp Pro Glu Lys
            180                 185                 190

Leu Asn Ser Tyr Gln Leu Thr Pro Gln Asp Val Ile Asn Ser Val Arg
        195                 200                 205

Ala Gln Asn Val Gln Val Ser Ala Gly Gln Leu Gly Gly Leu Pro Thr
    210                 215                 220

Ala Glu Gly Val Gln Leu Gln Ala Thr Val Ile Gly Lys Gln Arg Met
225                 230                 235                 240

Lys Thr Ala Glu Glu Phe Glu Asn Ile Leu Leu Lys Val Asn Pro Asp
                245                 250                 255

Gly Ser Gln Val Arg Leu Ala Asp Val Ala Glu Val Asn Leu Gly Asn
            260                 265                 270

Glu Asn Tyr Ala Thr Thr Gly Lys Tyr Asn Gly Ala Pro Ala Ala Gly
        275                 280                 285

Met Ala Leu Arg Leu Ala Thr Gly Ala Asn Gln Leu Glu Thr Ala Gly
    290                 295                 300

Arg Val Lys Glu Thr Leu Ala Glu Leu Glu Arg Phe Leu Pro Glu Gly
305                 310                 315                 320

Val Glu Ile Val Phe Pro Tyr Asp Thr Thr Pro Val Val Ser Ala Ser
                325                 330                 335

Ile Glu Thr Val Ala Met Thr Leu Ile Glu Ala Val Val Leu Val Phe
```

-continued

```
                 340                 345                 350
Leu Val Met Phe Leu Phe Leu Gln Ser Trp Arg Ala Thr Ile Ile Pro
                355                 360                 365
Thr Leu Ala Val Pro Val Val Leu Leu Ala Thr Phe Gly Val Leu Tyr
            370                 375             380
Ala Phe Gly Phe Thr Val Asn Val Met Thr Met Phe Ala Met Val Leu
385                 390                 395                 400
Ala Ile Gly Leu Leu Val Asp Asp Ala Ile Val Val Glu Asn Val
                405                 410                 415
Glu Arg Leu Met Glu Glu Gly Leu Ser Pro Lys Glu Ala Ala Lys
                420                 425                 430
Lys Ser Met Asp Gln Ile Ser Gly Ala Leu Leu Gly Ile Gly Leu Val
                435                 440                 445
Ile Ser Ala Val Phe Leu Pro Met Ala Phe Phe Gly Gly Ser Thr Gly
            450                 455             460
Val Ile Tyr Arg Gln Phe Ser Val Thr Ile Ile Ser Ala Met Ser Phe
465                 470                 475                 480
Ser Val Leu Val Ala Phe Ile Phe Thr Pro Ala Leu Cys Ala Thr Leu
                485                 490                 495
Leu Lys Pro Gly Asp Gln His Val Arg Lys Gly Phe Phe Gly Trp Phe
                500                 505                 510
Asn Arg Thr Phe Asp Arg Ser Ala Asp Arg Tyr Lys Ser Gly Val Ser
                515                 520                 525
Tyr Leu Ile Lys Arg Lys Gly Arg Phe Met Gly Val Tyr Leu Leu Leu
                530                 535                 540
Val Val Ala Val Gly Phe Leu Phe Lys Gly Leu Pro Thr Ala Phe Leu
545                 550                 555                 560
Pro Asp Glu Asp Gln Gly Val Met Ile Val Met Val Gln Leu Pro Thr
                565                 570                 575
Asn Ala Thr Gly Glu Arg Thr Glu Ala Val Leu Ala Glu Ala Gly Asn
                580                 585                 590
Tyr Leu Leu Glu Glu Glu Ser Glu Val Val Lys Ser Val Met Ser Val
                595                 600                 605
Arg Gly Phe Asn Phe Ala Gly Arg Gly Gln Asn Ser Gly Ile Leu Phe
                610                 615                 620
Val Asp Leu Lys Pro Phe Ala Asp Arg Glu Ser Phe Ala Gln Ser Val
625                 630                 635                 640
Phe Ala Leu Ala Gly Arg Ser Gly Ala Arg Phe Ala Gln Ile Lys Asp
                645                 650                 655
Ala Ile Val Phe Pro Ile Val Pro Ala Ile Leu Glu Leu Gly Asn
                660                 665                 670
Ala Thr Gly Phe Asp Leu Tyr Leu Lys Asp Asn Gly Ala Ile Gly His
                675                 680                 685
His Ala Leu Met Ala Ala Thr Asn Glu Phe Ile Ser Arg Ala Asn Ala
                690                 695                 700
Ala Pro Glu Leu Asn Met Val Arg His Asn Gly Leu Pro Asp Glu Pro
705                 710                 715                 720
Gln Tyr Gln Val Ile Ile Asp Asp Glu Lys Ala Arg Leu Leu Gln Val
                725                 730                 735
Ser Ile Ala Asp Ile Asn Ala Thr Met Ser Ala Ala Trp Gly Ser Ser
                740                 745                 750
Tyr Val Asn Asp Phe Leu His Asn Gly Arg Val Lys Lys Val Tyr Val
                755                 760                 765
```

```
Gln Gly Lys Pro Asp Ser Arg Leu Ala Pro Glu Asp Phe Asp Lys Trp
    770                 775                 780

Phe Val Arg Asn Ala Gln Gly Glu Met Val Pro Phe Ala Ala Phe Ala
785                 790                 795                 800

Thr Gly Glu Trp Val Phe Gly Ser Pro Arg Leu Gln Arg Tyr Gln Gly
                805                 810                 815

Leu Pro Ala Thr Gln Ile Gln Gly Ala Pro Ala Asn Gly Tyr Ser Thr
            820                 825                 830

Gly Asp Ala Met Ala Ala Leu Glu Arg Ile Ala Ala Asp Leu Pro Gln
        835                 840                 845

Gly Leu Gly Leu Glu Tyr Thr Gly Leu Ser Phe Glu Glu Lys Gln Ala
    850                 855                 860

Gly Asn Gln Ala Met Met Leu Tyr Leu Leu Ser Ile Leu Val Val Phe
865                 870                 875                 880

Leu Cys Leu Ala Ala Leu Tyr Glu Ser Trp Ser Ile Pro Phe Ala Val
                885                 890                 895

Ile Met Leu Val Pro Leu Gly Val Leu Gly Ala Val Leu Ala Thr Met
            900                 905                 910

Ala Arg Gly Leu Ser Asn Asp Val Phe Phe Gln Val Gly Met Leu Thr
        915                 920                 925

Thr Met Gly Leu Ala Ala Lys Asn Ala Ile Leu Ile Val Glu Phe Ala
    930                 935                 940

Arg Gln Leu Tyr Glu Gln Glu Gly Lys Pro Leu Leu Gln Ala Thr Ala
945                 950                 955                 960

Glu Ala Ala Arg Leu Arg Leu Arg Pro Ile Ile Met Thr Ser Leu Ala
                965                 970                 975

Phe Ile Phe Gly Val Leu Pro Met Ala Ile Ala Ser Gly Ala Ser Ser
            980                 985                 990

Ala Ser Gln His Ala Ile Gly Thr Ala Val Val Gly Gly Thr Leu Ala
        995                 1000                1005

Ala Thr Ile Leu Ala Ile Phe Phe Val Pro Leu Phe Tyr Val Phe
    1010                1015                1020

Val Val Gly Leu Thr Gly Lys Arg Lys Ser Ala Asp Asp
    1025                1030                1035

<210> SEQ ID NO 4
<211> LENGTH: 1043
<212> TYPE: PRT
<213> ORGANISM: Pseudoalteromonas haloplanktis

<400> SEQUENCE: 4

Met Ser Arg Tyr Phe Ile Asp Lys Pro Ile Phe Ala Trp Val Leu Ala
1               5                   10                  15

Ile Ile Val Met Leu Ala Gly Ile Leu Ala Val Lys Ser Leu Pro Ile
                20                  25                  30

Ala Gln Tyr Pro Ser Ile Ala Pro Pro Ala Ile Ser Ile Thr Ala Asn
            35                  40                  45

Tyr Pro Gly Ala Ser Ala Gln Thr Leu Glu Asp Ser Val Thr Gln Val
        50                  55                  60

Ile Glu Gln Lys Met Lys Gly Leu Asp Gly Leu Leu Tyr Met Ser Ser
65                  70                  75                  80

Thr Ser Glu Ser Asn Gly Ser Ala Thr Leu Thr Leu Thr Phe Asn Ala
                85                  90                  95

Asp Thr Asp Pro Asp Ile Ala Gln Val Gln Val Gln Asn Lys Leu Ala
```

```
            100             105             110
Thr Ala Thr Pro Leu Leu Pro Glu Glu Val Gln Arg Gln Gly Val Val
        115             120             125
Val Ala Lys Ala Ala Arg Asn Phe Leu Leu Val Leu Ala Phe Val Ser
        130             135             140
Lys Asp Gly Ser Met Thr Asn Ile Asp Ile Gly Asp Tyr Val Ala Ser
145             150             155             160
Asn Val Gln Asp Ile Val Ser Arg Val Asp Gly Val Gly Glu Ala Gln
                165             170             175
Leu Phe Gly Ser Gln Tyr Ala Met Arg Ile Trp Leu Asp Pro Ala Lys
            180             185             190
Leu Gln Asn Phe Lys Leu Thr Pro Asn Asp Ile Gly Ala Ala Ile Thr
        195             200             205
Ala Gln Asn Ala Gln Val Ser Ala Gly Gln Leu Gly Gly Met Pro Ala
        210             215             220
Ile Ala Gly Gln Gln Leu Asn Ala Thr Ile Thr Ala Gln Ser Arg Leu
225             230             235             240
Gln Thr Pro Glu Gln Phe Glu Asn Ile Leu Val Lys Thr Asn Ser Asp
                245             250             255
Gly Ser Val Val Arg Leu Lys Asp Val Ala Arg Val Glu Leu Gly Gly
            260             265             270
Glu Asn Tyr Gly Val Val Ala Arg Tyr Asn Gly Asp Pro Ala Ala Gly
            275             280             285
Ile Gly Ile Lys Leu Ala Ser Gly Ala Asn Ala Leu Asp Thr Ala Glu
        290             295             300
Gly Val Lys Lys Ala Leu Glu Asp Leu Lys Pro Phe Phe Pro Glu Gly
305             310             315             320
Leu Asp Val Ala Ile Pro Tyr Asp Thr Thr Pro Phe Val Ser Leu Ser
                325             330             335
Ile Glu Lys Val Val His Thr Leu Ile Glu Ala Val Ile Leu Val Phe
            340             345             350
Val Val Met Tyr Leu Phe Leu Gln Asn Phe Arg Ala Thr Leu Ile Pro
        355             360             365
Thr Ile Ala Val Pro Val Val Leu Leu Gly Thr Phe Ala Ile Leu Tyr
        370             375             380
Thr Phe Gly Tyr Ser Ile Asn Thr Leu Thr Met Phe Ala Met Val Leu
385             390             395             400
Ala Ile Gly Leu Leu Val Asp Asp Ala Ile Val Val Val Glu Asn Val
                405             410             415
Glu Arg Leu Met Thr Glu Glu Lys Leu Ser Ala Leu Asp Ala Thr Arg
            420             425             430
Lys Ser Met Asp Glu Ile Lys Gly Ala Leu Val Gly Ile Ala Met Val
            435             440             445
Leu Ser Ala Val Phe Ile Pro Met Ala Phe Phe Ser Gly Ser Thr Gly
        450             455             460
Val Ile Tyr Arg Gln Phe Ser Ile Thr Ile Val Ser Ala Met Gly Leu
465             470             475             480
Ser Val Leu Val Ala Leu Ile Leu Thr Pro Ala Leu Cys Ala Thr Leu
                485             490             495
Leu Lys Pro Ser His Val His Asp Lys Thr Ser Phe Ile Gly Arg Phe
            500             505             510
Phe Ser Gly Phe Asn Arg Gly Phe Asp Lys Thr Asn Arg Gly Ala Gln
            515             520             525
```

```
Gly Ile Val Gly Arg Met Ile Ser Gln Ser Lys Arg Tyr Leu Leu Ile
    530                 535                 540

Tyr Gly Val Leu Val Gly Met Val Tyr Val Phe Ser Ser Leu Pro
545                 550                 555                 560

Thr Ala Phe Leu Pro Asp Glu Asp Gln Gly Ile Leu Phe Asn Gln Val
                565                 570                 575

Met Leu Pro Ala Gly Ser Thr Ile Glu Gln Thr Leu Gly Val Val Glu
                580                 585                 590

Lys Val Glu Asn His Tyr Leu Asn Asp Gln Ala Glu Ala Val Gly Ser
                595                 600                 605

Ile Phe Thr Val Thr Gly Phe Ser Phe Ala Gly Ser Gly Gln Asn Ser
    610                 615                 620

Ala Ile Gly Phe Val Asn Leu Lys His Trp Asp Glu Arg Gln Arg Asp
625                 630                 635                 640

Asp Leu Ser Val Asn Ala Val Ala Gly Lys Gly Met Gly Tyr Phe Ser
                645                 650                 655

Thr Ile Lys Glu Ala Phe Val Phe Ala Phe Pro Pro Ala Ile Val
                660                 665                 670

Glu Leu Gly Thr Ala Asn Gly Phe Asn Met Phe Leu Gln Asp Arg Val
    675                 680                 685

Gly Leu Gly His Asp Glu Leu Leu Asn Ala Arg Asn Met Leu Leu Gly
    690                 695                 700

Met Ala Ser Lys Ser Pro Val Leu Ala Gly Val Arg Pro Asn Gly Gln
705                 710                 715                 720

Glu Asp Met Pro Glu Leu Gln Leu Asp Ile Asp Leu Ala Lys Ala Glu
                725                 730                 735

Ala Leu Gly Val Thr Gln Thr Asp Ile Asn Ser Thr Leu Ser Thr Ala
                740                 745                 750

Trp Gly Ser Arg Tyr Val Asn Asp Phe Ile Asp Arg Gly Arg Val Lys
    755                 760                 765

Lys Val Tyr Met Gln Gly Glu Ala Asp Ser Arg Met Val Pro Glu Asp
770                 775                 780

Leu Asn Lys Trp Tyr Val Arg Asn Asn Gly Asp Met Val Pro Phe
785                 790                 795                 800

Ala Ala Phe Ala Ser Ser His Trp Ser Tyr Gly Ser Pro Arg Leu Glu
                805                 810                 815

Arg Tyr Asn Gly Phe Ser Ala Met Glu Ile Gln Gly Ser Ala Ala Pro
                820                 825                 830

Gly Tyr Ser Thr Gly Gln Ala Met Asp Glu Met Glu Arg Leu Val Lys
    835                 840                 845

Gln Leu Pro Asn Gly Ile Ala Ser Glu Trp Ser Gly Ile Ser Tyr Gln
    850                 855                 860

Glu Arg Ser Ser Gly Gly Gln Ala Pro Leu Leu Tyr Gly Leu Ser Leu
865                 870                 875                 880

Leu Phe Val Phe Leu Cys Leu Ala Ala Leu Tyr Glu Ser Trp Ser Val
                885                 890                 895

Pro Phe Ala Val Met Ile Ile Val Pro Leu Gly Ile Phe Gly Ala Ile
                900                 905                 910

Met Ala Ala Leu Ile Gly Asn Leu Ser Asn Asp Ile Tyr Leu Gln Val
    915                 920                 925

Gly Leu Leu Thr Thr Ile Gly Leu Ala Ser Lys Asn Ala Ile Leu Ile
    930                 935                 940
```

```
Val Glu Phe Ala Ile His Lys Met Glu Glu Gly Leu Ser Leu Val Asp
945                 950                 955                 960

Ala Ala Ile Ala Ala Val Lys Leu Arg Leu Arg Pro Val Leu Met Thr
            965                 970                 975

Ser Leu Ala Phe Ile Cys Gly Val Val Pro Leu Ala Ile Ala Ser Ser
            980                 985                 990

Ala Gly Ser Gly Ala Gln Asn Ala Leu Gly Ile Ser Ile Ile Gly Gly
    995                 1000                1005

Thr Leu Ala Ala Ser Thr Leu Val Val Leu Phe Val Pro Leu Phe
    1010                1015                1020

Phe Val Leu Val Arg Lys Thr Phe Ser Ser Lys Ser Ala Val Ala
    1025                1030                1035

Thr Lys Glu Ser Glu
    1040

<210> SEQ ID NO 5
<211> LENGTH: 1034
<212> TYPE: PRT
<213> ORGANISM: E. coli

<400> SEQUENCE: 5

Met Ala Asn Phe Phe Ile Arg Arg Pro Ile Phe Ala Trp Val Leu Ala
1               5                   10                  15

Ile Ile Leu Met Met Ala Gly Ala Leu Ala Ile Leu Gln Leu Pro Val
            20                  25                  30

Ala Gln Tyr Pro Thr Ile Ala Pro Pro Ala Val Ser Val Ser Ala Asn
        35                  40                  45

Tyr Pro Gly Ala Asp Ala Gln Thr Val Gln Asp Thr Val Thr Gln Val
    50                  55                  60

Ile Glu Gln Asn Met Asn Gly Ile Asp Asn Leu Met Tyr Met Ser Ser
65                  70                  75                  80

Thr Ser Asp Ser Ala Gly Ser Val Thr Ile Thr Leu Thr Phe Gln Ser
                85                  90                  95

Gly Thr Asp Pro Asp Ile Ala Gln Val Gln Val Gln Asn Lys Leu Gln
            100                 105                 110

Leu Ala Thr Pro Leu Leu Pro Gln Glu Val Gln Gln Gln Gly Ile Ser
        115                 120                 125

Val Glu Lys Ser Ser Ser Tyr Leu Met Val Ala Gly Phe Val Ser
    130                 135                 140

Asp Asn Pro Gly Thr Thr Gln Asp Asp Ile Ser Asp Tyr Val Ala Ser
145                 150                 155                 160

Asn Val Lys Asp Thr Leu Ser Arg Leu Asn Gly Val Gly Asp Val Gln
                165                 170                 175

Leu Phe Gly Ala Gln Tyr Ala Met Arg Ile Trp Leu Asp Ala Asp Leu
            180                 185                 190

Leu Asn Lys Tyr Lys Leu Thr Pro Val Asp Val Ile Asn Gln Leu Lys
        195                 200                 205

Val Gln Asn Asp Gln Ile Ala Ala Gly Gln Leu Gly Gly Thr Pro Ala
    210                 215                 220

Leu Pro Gly Gln Gln Leu Asn Ala Ser Ile Ile Ala Gln Thr Arg Phe
225                 230                 235                 240

Lys Asn Pro Glu Glu Phe Gly Lys Val Thr Leu Arg Val Asn Ser Asp
                245                 250                 255

Gly Ser Val Val Arg Leu Lys Asp Val Ala Arg Val Glu Leu Gly Gly
            260                 265                 270
```

-continued

Glu Asn Tyr Asn Val Ile Ala Arg Ile Asn Gly Lys Pro Ala Ala Gly
            275                 280                 285

Leu Gly Ile Lys Leu Ala Thr Gly Ala Asn Ala Leu Asp Thr Ala Lys
290                 295                 300

Ala Ile Lys Ala Lys Leu Ala Glu Leu Gln Pro Phe Phe Pro Gln Gly
305                 310                 315                 320

Met Lys Val Leu Tyr Pro Tyr Asp Thr Thr Pro Phe Val Gln Leu Ser
            325                 330                 335

Ile His Glu Val Val Lys Thr Leu Phe Glu Ala Ile Met Leu Val Phe
            340                 345                 350

Leu Val Met Tyr Leu Phe Leu Gln Asn Met Arg Ala Thr Leu Ile Pro
            355                 360                 365

Thr Ile Ala Val Pro Val Val Leu Leu Gly Thr Phe Ala Ile Leu Ala
370                 375                 380

Ala Phe Gly Tyr Ser Ile Asn Thr Leu Thr Met Phe Gly Met Val Leu
385                 390                 395                 400

Ala Ile Gly Leu Leu Val Asp Asp Ala Ile Val Val Glu Asn Val
            405                 410                 415

Glu Arg Val Met Met Glu Asp Lys Leu Pro Pro Lys Glu Ala Thr Glu
            420                 425                 430

Lys Ser Met Ser Gln Ile Gln Gly Ala Leu Val Gly Ile Ala Met Val
435                 440                 445

Leu Ser Ala Val Phe Ile Pro Met Ala Phe Phe Gly Gly Ser Thr Gly
450                 455                 460

Ala Ile Tyr Arg Gln Phe Ser Ile Thr Ile Val Ser Ala Met Ala Leu
465                 470                 475                 480

Ser Val Leu Val Ala Leu Ile Leu Thr Pro Ala Leu Cys Ala Thr Leu
            485                 490                 495

Leu Lys Pro Val Ser Ala Glu His His Glu Asn Lys Gly Gly Phe Phe
            500                 505                 510

Gly Trp Phe Asn Thr Thr Phe Asp His Ser Val Asn His Tyr Thr Asn
            515                 520                 525

Ser Val Gly Lys Ile Leu Gly Ser Thr Gly Arg Tyr Leu Leu Ile Tyr
            530                 535                 540

Ala Leu Ile Val Ala Gly Met Val Val Leu Phe Leu Arg Leu Pro Ser
545                 550                 555                 560

Ser Phe Leu Pro Glu Glu Asp Gln Gly Val Phe Leu Thr Met Ile Gln
            565                 570                 575

Leu Pro Ala Gly Ala Thr Gln Glu Arg Thr Gln Lys Val Leu Asp Gln
            580                 585                 590

Val Thr Asp Tyr Tyr Leu Lys Asn Glu Lys Ala Asn Val Glu Ser Val
            595                 600                 605

Phe Thr Val Asn Gly Phe Ser Phe Ser Gly Gln Ala Gln Asn Ala Gly
610                 615                 620

Met Ala Phe Val Ser Leu Lys Pro Trp Glu Glu Arg Asn Gly Asp Glu
625                 630                 635                 640

Asn Ser Ala Glu Ala Val Ile His Arg Ala Lys Met Glu Leu Gly Lys
            645                 650                 655

Ile Arg Asp Gly Phe Val Ile Pro Phe Asn Met Pro Ala Ile Val Glu
            660                 665                 670

Leu Gly Thr Ala Thr Gly Phe Asp Phe Glu Leu Ile Asp Gln Ala Gly
            675                 680                 685

-continued

Leu Gly His Asp Ala Leu Thr Gln Ala Arg Asn Gln Leu Leu Gly Met
    690                 695                 700

Ala Ala Gln His Pro Ala Ser Leu Val Ser Val Arg Pro Asn Gly Leu
705                 710                 715                 720

Glu Asp Thr Ala Gln Phe Lys Leu Glu Val Asp Gln Glu Lys Ala Gln
                725                 730                 735

Ala Leu Gly Val Ser Leu Ser Asp Ile Asn Gln Thr Ile Ser Thr Ala
            740                 745                 750

Leu Gly Gly Thr Tyr Val Asn Asp Phe Ile Asp Arg Gly Arg Val Lys
        755                 760                 765

Lys Leu Tyr Val Gln Ala Asp Ala Lys Phe Arg Met Leu Pro Glu Asp
770                 775                 780

Val Asp Lys Leu Tyr Val Arg Ser Ala Asn Gly Glu Met Val Pro Phe
785                 790                 795                 800

Ser Ala Phe Thr Thr Ser His Trp Val Tyr Gly Ser Pro Arg Leu Glu
                805                 810                 815

Arg Tyr Asn Gly Leu Pro Ser Met Glu Ile Gln Gly Glu Ala Ala Pro
            820                 825                 830

Gly Thr Ser Ser Gly Asp Ala Met Ala Leu Met Glu Asn Leu Ala Ser
        835                 840                 845

Lys Leu Pro Ala Gly Ile Gly Tyr Asp Trp Thr Gly Met Ser Tyr Gln
850                 855                 860

Glu Arg Leu Ser Gly Asn Gln Ala Pro Ala Leu Val Ala Ile Ser Phe
865                 870                 875                 880

Val Val Val Phe Leu Cys Leu Ala Ala Leu Tyr Glu Ser Trp Ser Ile
                885                 890                 895

Pro Val Ser Val Met Leu Val Val Pro Leu Gly Ile Val Gly Val Leu
            900                 905                 910

Leu Ala Ala Thr Leu Phe Asn Gln Lys Asn Asp Val Tyr Phe Met Val
        915                 920                 925

Gly Leu Leu Thr Thr Ile Gly Leu Ser Ala Lys Asn Ala Ile Leu Ile
930                 935                 940

Val Glu Phe Ala Lys Asp Leu Met Glu Lys Glu Gly Lys Gly Val Val
945                 950                 955                 960

Glu Ala Thr Leu Met Ala Val Arg Met Arg Leu Arg Pro Ile Leu Met
                965                 970                 975

Thr Ser Leu Ala Phe Ile Leu Gly Val Leu Pro Leu Ala Ile Ser Asn
            980                 985                 990

Gly Ala Gly Ser Gly Ala Gln Asn Ala Val Gly Ile Gly Val Met Gly
        995                 1000                1005

Gly Met Val Ser Ala Thr Leu Leu Ala Ile Phe Phe Val Pro Val
    1010                1015                1020

Phe Phe Val Val Ile Arg Arg Cys Phe Lys Gly
    1025                1030

<210> SEQ ID NO 6
<211> LENGTH: 33
<212> TYPE: DNA
<213> ORGANISM: Artificial Sequence
<220> FEATURE:
<223> OTHER INFORMATION: synthetic primer - DelB F

<400> SEQUENCE: 6
ctgaacagtc caagtcttaa cttaaacagg agc                          33

```
<210> SEQ ID NO 7
<211> LENGTH: 25
<212> TYPE: DNA
<213> ORGANISM: Artificial Sequence
<220> FEATURE:
<223> OTHER INFORMATION: synthetic primer - DelB R

<400> SEQUENCE: 7
catactagca ctaacccgca gcagg                                                25

<210> SEQ ID NO 8
<211> LENGTH: 29
<212> TYPE: DNA
<213> ORGANISM: Artificial Sequence
<220> FEATURE:
<223> OTHER INFORMATION: synthetic primer - DelAB F

<400> SEQUENCE: 8
cgtgccatat gttcgtgaat ttacaggcg                                            29

<210> SEQ ID NO 9
<211> LENGTH: 25
<212> TYPE: DNA
<213> ORGANISM: Artificial Sequence
<220> FEATURE:
<223> OTHER INFORMATION: synthetic primer - DelAB R

<400> SEQUENCE: 9
catactagca ctaacccgca gcagg                                                25

<210> SEQ ID NO 10
<211> LENGTH: 59
<212> TYPE: DNA
<213> ORGANISM: Artificial Sequence
<220> FEATURE:
<223> OTHER INFORMATION: synthetic primer - TolC F

<400> SEQUENCE: 10
aaagatcttt taagaaggag atatacatat gaagaaattg ctccccattc ttatcggcc           59

<210> SEQ ID NO 11
<211> LENGTH: 60
<212> TYPE: DNA
<213> ORGANISM: Artificial Sequence
<220> FEATURE:
<223> OTHER INFORMATION: synthetic primer - TolC R

<400> SEQUENCE: 11
actcgaggga tcctcagtgg tggtggtggt ggtggttacg aaagggtta tgaccgttac           60

<210> SEQ ID NO 12
<211> LENGTH: 55
<212> TYPE: DNA
<213> ORGANISM: Artificial Sequence
<220> FEATURE:
<223> OTHER INFORMATION: synthetic primer - AcrA F

<400> SEQUENCE: 12
taaagatctt ttaagaagga gatatacaga tgaacaaaaa cagagggttt acgcc              55

<210> SEQ ID NO 13
<211> LENGTH: 56
<212> TYPE: DNA
<213> ORGANISM: Artificial Sequence
<220> FEATURE:
<223> OTHER INFORMATION: synthetic primer - AcrA R
```

<400> SEQUENCE: 13
aaaacatatg ttaacggctc ctgtttaagt taagacttgg actgttcagg ctgagc       56

<210> SEQ ID NO 14
<211> LENGTH: 36
<212> TYPE: DNA
<213> ORGANISM: Artificial Sequence
<220> FEATURE:
<223> OTHER INFORMATION: synthetic primer - AcrB F

<400> SEQUENCE: 14
ccaagtctta acttaaacag gagccgttaa catatg       36

<210> SEQ ID NO 15
<211> LENGTH: 27
<212> TYPE: DNA
<213> ORGANISM: Artificial Sequence
<220> FEATURE:
<223> OTHER INFORMATION: synthetic primer - AcrB R

<400> SEQUENCE: 15
gatccttact cgagggatcc tcagtgg       27

<210> SEQ ID NO 16
<211> LENGTH: 60
<212> TYPE: DNA
<213> ORGANISM: Artificial Sequence
<220> FEATURE:
<223> OTHER INFORMATION: synthetic primer - Fdc1 F

<400> SEQUENCE: 16
aaagatcttt taagaaggag atatacatat gaggaagcta aatccagctt tagaatttag       60

<210> SEQ ID NO 17
<211> LENGTH: 60
<212> TYPE: DNA
<213> ORGANISM: Artificial Sequence
<220> FEATURE:
<223> OTHER INFORMATION: synthetic primer - Fdc1 R

<400> SEQUENCE: 17
tccttcttaa acccgggtcc ttatttatat ccgtaccttt tccaattttc atttactttg       60

<210> SEQ ID NO 18
<211> LENGTH: 59
<212> TYPE: DNA
<213> ORGANISM: Artificial Sequence
<220> FEATURE:
<223> OTHER INFORMATION: synthetic primer - Pal2 F

<400> SEQUENCE: 18
ataaggaccc gggtttaaga aggagatata caaatggatc aaatcgaagc aatgttgtg       59

<210> SEQ ID NO 19
<211> LENGTH: 38
<212> TYPE: DNA
<213> ORGANISM: Artificial Sequence
<220> FEATURE:
<223> OTHER INFORMATION: synthetic primer - Pal2 R

<400> SEQUENCE: 19
cttactcgag ttagcaaatc ggaatcggag ctccgttc       38

<210> SEQ ID NO 20
<211> LENGTH: 27

```
<212> TYPE: DNA
<213> ORGANISM: Artificial Sequence
<220> FEATURE:
<223> OTHER INFORMATION: synthetic primer - Cam F

<400> SEQUENCE: 20
cggtgctcag cctgaacagt ccaagtc                                        27

<210> SEQ ID NO 21
<211> LENGTH: 34
<212> TYPE: DNA
<213> ORGANISM: Artificial Sequence
<220> FEATURE:
<223> OTHER INFORMATION: synthetic primer - Cam R

<400> SEQUENCE: 21
tctttcgact gagcctttcg ttttatttga tgcc                                34

<210> SEQ ID NO 22
<211> LENGTH: 28
<212> TYPE: DNA
<213> ORGANISM: Artificial Sequence
<220> FEATURE:
<223> OTHER INFORMATION: synthetic primer - A279T R

<400> SEQUENCE: 22
gccgttaaac tctgtgatga tgtcgtag                                       28

<210> SEQ ID NO 23
<211> LENGTH: 28
<212> TYPE: DNA
<213> ORGANISM: Artificial Sequence
<220> FEATURE:
<223> OTHER INFORMATION: synthetic primer - A279T F

<400> SEQUENCE: 23
ctacgacatc atcacagagt taacggc                                        28

<210> SEQ ID NO 24
<211> LENGTH: 22
<212> TYPE: DNA
<213> ORGANISM: Artificial Sequence
<220> FEATURE:
<223> OTHER INFORMATION: synthetic primer - Q584R R

<400> SEQUENCE: 24
gtgtacgttc ccgcgttgca cc                                             22

<210> SEQ ID NO 25
<211> LENGTH: 22
<212> TYPE: DNA
<213> ORGANISM: Artificial Sequence
<220> FEATURE:
<223> OTHER INFORMATION: synthetic primer - Q584R F

<400> SEQUENCE: 25
ggtgcaacgc gggaacgtac ac                                             22

<210> SEQ ID NO 26
<211> LENGTH: 34
<212> TYPE: DNA
<213> ORGANISM: Artificial Sequence
<220> FEATURE:
<223> OTHER INFORMATION: synthetic primer - F617L R

<400> SEQUENCE: 26
```
ctgaccacgt cccgcaaggc cgaagccgtt aacg                          34

<210> SEQ ID NO 27
<211> LENGTH: 34
<212> TYPE: DNA
<213> ORGANISM: Artificial Sequence
<220> FEATURE:
<223> OTHER INFORMATION: synthetic primer - F617L F

<400> SEQUENCE: 27
cgttaacggc ttcggccttg cgggacgtgg tcag                          34

<210> SEQ ID NO 28
<211> LENGTH: 23
<212> TYPE: DNA
<213> ORGANISM: Artificial Sequence
<220> FEATURE:
<223> OTHER INFORMATION: synthetic primer - L822P R

<400> SEQUENCE: 28
catggatggc gggccgttgt aac                                      23

<210> SEQ ID NO 29
<211> LENGTH: 23
<212> TYPE: DNA
<213> ORGANISM: Artificial Sequence
<220> FEATURE:
<223> OTHER INFORMATION: synthetic primer - L822P F

<400> SEQUENCE: 29
gttacaacgg cccgccatcc atg                                      23

<210> SEQ ID NO 30
<211> LENGTH: 22
<212> TYPE: DNA
<213> ORGANISM: Artificial Sequence
<220> FEATURE:
<223> OTHER INFORMATION: synthetic primer - F927S R

<400> SEQUENCE: 30
ggcctacctg ggagtaaacg tc                                       22

<210> SEQ ID NO 31
<211> LENGTH: 22
<212> TYPE: DNA
<213> ORGANISM: Artificial Sequence
<220> FEATURE:
<223> OTHER INFORMATION: synthetic primer - F927S F

<400> SEQUENCE: 31
gacgtttact cccaggtagg cc                                       22

<210> SEQ ID NO 32
<211> LENGTH: 24
<212> TYPE: DNA
<213> ORGANISM: Artificial Sequence
<220> FEATURE:
<223> OTHER INFORMATION: synthetic primer - F1033Y R

<400> SEQUENCE: 32
cattcttgcg gctatagcgg cggc                                     24

<210> SEQ ID NO 33
<211> LENGTH: 24
<212> TYPE: DNA
<213> ORGANISM: Artificial Sequence

```
<220> FEATURE:
<223> OTHER INFORMATION: synthetic primer - F1033Y F

<400> SEQUENCE: 33
gccgccgcta tagccgcaag aatg                                              24
```

MODIFIED HOST CELLS HAVING TOLERANCE TO α-OLEFINS

CROSS-REFERENCE TO RELATE APPLICATIONS

This application is a U.S. National Stage entry of International Application No. PCT/US2015/028296, filed Apr. 29, 2015, which claims benefit of priority to U.S. provisional application No. 61/986,669, filed Apr. 30, 2014, each of which is herein incorporated by reference.

STATEMENT AS TO RIGHTS TO INVENTIONS MADE UNDER FEDERALLY SPONSORED RESEARCH AND DEVELOPMENT

The invention was made with government support under Contract No. DE-AC02-05CH11231 awarded by the U.S. Department of Energy. The government has certain rights in the invention.

REFERENCE TO SUBMISSION OF A SEQUENCE LISTING AS AN ASCII TEXT FILE

This application includes a Sequence Listing as a text file named "077429_1028525_SEQ_LST_ST25" created on Oct. 28, 2016 and containing 50,785 bytes. The material contained in this text file is hereby incorporated by reference in its entirety for all purposes.

BACKGROUND OF THE INVENTION

Recent interest in biofuels and alternative sources of chemicals has made microbial production of bulk chemicals an important focus of development. However, many chemicals of industrial interest are toxic to the microorganisms producing them. Microbial production levels are thus constrained by the toxicity limits of the organism to the final product. Host engineering to improve strain tolerance towards target compounds is thus important to increase production levels.

Different compounds may require different host engineering approaches, as toxicity relates to the mode of inhibition, chemical properties, and hydrophobicity of a compound. Hydrophobic solvent-like compounds are hypothesized to impact membrane permeability and fluidity, diminish energy transduction and interfere with membrane protein function, affecting a range of essential cellular processes (Wagner et al, 2007). The cell defense mechanisms that respond to these compounds include induction of chaperones, modification of membrane composition and cellular morphology, and induction of active membrane efflux pump transporter portents that export the compounds out of the cells and the membrane. Of these, efflux pumps have recently emerged as an important target in engineering of host cells (Doshi et al. 2013; Dunlop et al. 2011; Dunlop et al, 2010; Fisher et al. 2013; Foo and Leong 2013).

Efflux pump proteins, also referred to herein simply as "pump" proteins, provide the general mechanism for the export of toxic compounds from cells (Nikaido 2009: Takatsuka et al. 2010). One of the best-characterized families of pumps, and also the key pumps in gram negative bacteria for tolerance towards solvent-like compounds, belong to the hydrophobe/amphiphile efflux (HAE1) family of resistance-nodulation-di vision (RND) pumps (Nikaido and Takatsuka 2009; Ramos et al. 2002; Tseng et al. 1999). RND efflux pumps are composed of 3 subunits: (i) an inner membrane unit proton antiporter that binds the substrate and transports if through (ii) the outer membrane channel subunit, and (iii) periplasmic subunit that connects and stabilizes the inner and outer membrane units (Nikaido and Takatsuka 2009).

The *E. coli* AcrAB-TolC efflux pump is a member of the HAE1 family. AcrAB-TolC is composed of AcrB (inner membrane protein), TolC (outer membrane protein) and AcrA (periplasmic protein) and has been extensively studied (Murakami et al. 2002; Tikhonova et al. 2011). There are many reports in the scientific literature characterizing the mechanism of action of AcrB, including its rotational conformation changes (Seeger et al. 2006; Seeger et al. 2008; Sennhauser et al. 2007; Takatsuka and Nikaido 2009; Takatsuka and Nikaido 2010) as well as potential binding pockets and the amino acids involved in substrate recognition (Eicher et al. 2012; Husain and Nikaido 2010; Vargiu and Nikaido 2012). The reported substrate entry points have been located in the periplasm (Takatsuka and Nikaido 2007), the membrane and/or in the cytoplasm side of the pump (Eicher et al. 2012; Husain and Nikaido 2010; Murakami et al. 2004; Murakami and Yamaguchi 2003; Sennhauser et al. 2007). Although AcrB functions with AcrA and TolC in *E. coli*, AcrB also has efflux pump activity in the absence of AcrA and TolC (see, e.g., Kapoor & Wendell, *Nano Lett.* 2013, 13, 2189-2193, 2013).

AcrB has broad substrate specificity that ranges from detergents to antibiotics and solvents. This pump is reported to play a major role in the secretion of various alkanes such as hexane, heptane, octane, and nonane (Takatsuka et al. 2010) and also in imparting tolerance to various terpene based biofuel compounds (Dunlop et al. 2011).

Production of α-olefins by microorganisms is hampered by toxicity of the compound to the host cells. There is therefore a need to improve tolerance. This invention addresses that need, in part, by providing host cells with genetic modifications to an acrB gene, or homolog, that result in improved tolerance to α-olefins and accordingly, increased α-olefin yields from modified host cells that produce the compounds.

SUMMARY OF THE INVENTION

The present invention is based, in part, on the discovery that an AcrB polypeptide can be engineered such that expression of the modified AcrB polypeptide in a host cell that produces an α-olefin compound improves tolerance of the host cell to the compound. This section summarizes illustrative embodiments of the invention, but does not limit the invention to these embodiments.

In one aspect, the invention provides a microorganism host cell comprising a recombinant non-naturally occurring variant AcrB-like polypeptide that comprises at least one amino acid sequence mutation relative to a native AcrB-like polypeptide sequence, wherein the non-naturally occurring AcrB-like polypeptide reduces accumulation of alpha-olefin compounds in the host cell in comparison to a wild-type host cell that expresses the native AcrB-like polypeptide at a native level. The sequence mutation may be an amino acid substitution relative to the native AcrB-like polypeptide sequence, e.g., an amino acid other than the corresponding amino acid of SEQ ID NO:1. In some embodiments, the recombinant non-naturally occurring variant AcrB-like polypeptide amino acid sequence is substantially identical to SEQ ID NO:1 and comprises one or more amino acid substitutions within 2 to 8 Angstroms of, or at, a position corresponding to amino acid 279, amino acid 584, amino acid 617, amino acid 822, amino acid 927, or amino acid 1033, as numbered with reference to SEQ ID NO:1. In some embodiments, the recombinant non-naturally occurring variant AcrB-like polypeptide comprises an amino acid other than alanine at a position corresponding to amino acid 279. In some embodiments, the recombinant non-naturally occurring variant AcrB-like polypeptide comprises a threonine at a position corresponding to amino acid 279. In some embodiments, the recombinant non-naturally occurring variant AcrB-like polypeptide comprises an amino acid other than a glutamine at a position corresponding to amino acid 584. In some embodiments, the recombinant non-naturally occurring variant AcrB-like polypeptide comprises an arginine at a position corresponding to amino acid 584. In some embodiments, the recombinant non-naturally occurring AcrB-like polypeptide comprises an amino acid other than a leucine at a position corresponding to amino acid 617. In some embodiments, the recombinant non-naturally occurring AcrB-like polypeptide comprises a phenylalanine at a position corresponding to amino acid 617. In some embodiments, the recombinant non-naturally occurring variant AcrB-like polypeptide comprises an amino acid other than a leucine at a position corresponding to amino acid 822. In some embodiments, the recombinant non-naturally occurring variant AcrB-like polypeptide comprises proline at a position corresponding to amino acid 822. In some embodiments, the recombinant non-naturally occurring variant AcrB-like polypeptide comprises an amino acid residue other than a phenylalanine at a position corresponding to amino acid 927. In some embodiments, the recombinant non-naturally occurring variant AcrB-like polypeptide comprises a serine at a position corresponding to amino acid 927. In some embodiments, the recombinant non-naturally occurring variant AcrB-like polypeptide comprises an amino acid residue other than a phenylalanine at a position corresponding to amino acid 1033. In some embodiments, the recombinant non-naturally occurring variant AcrB-like polypeptide comprises a tyrosine at a position corresponding to amino acid 1033. In some embodiments, the alpha-olefin compounds comprise 1-hexene, or a derivative thereof. In such embodiments, the host cell typically produces a greater amount of the 1-hexene, or derivative thereof, as compared to a wild-type host cell that expresses the native AcrB-like polypeptide at a native level. In additional embodiments, the host cell further comprises the proteins necessary to produce 1-hexene or a derivative thereof. The host cell may be a bacterial cell, e.g., either a gram negative or a gram positive host cell. In some embodiments, the bacterial host cell is a gram negative cell, such as an *E. coli* cell. In some embodiments, the host cell is a yeast host cell.

In a further aspect, the invention provides a recombinant variant AcrB polypeptide, wherein the recombinant variant AcrB polypeptide has at least 70% identity, or at least 80%, 85%, 90%, or 95% identity, to SEQ ID NO:1 and comprises one or more amino acid substitutions within 2 to 8 Angstroms of, or at, a position corresponding to amino acid 279, amino acid 584, amino acid 617, amino acid 822, amino acid 927, or amino acid 1033 of SEQ ID NO: 1. In some embodiments, the variant AcrB polypeptide comprises an amino acid other than alanine at a position corresponding to amino acid 279. In sortie embodiments, the recombinant variant AcrB polypeptide comprises a threonine at a position corresponding to amino acid 279. In some embodiments, the recombinant variant AcrB polypeptide comprises an amino acid other than a glutamine at a position corresponding to amino acid 584. In some embodiments, the recombinant variant AcrB polypeptide comprises an arginine at a position corresponding to amino acid 584. In some embodiments, the recombinant variant AcrB polypeptide comprises an amino acid other than a leucine at a position corresponding to amino acid 617. In some embodiments, the recombinant variant AcrB polypeptide comprises a phenylalanine at a position corresponding to amino acid 617. In some embodiments, the recombinant variant AcrB polypeptide comprises an amino acid other than a leucine at a position corresponding to amino acid 822. In some embodiments, the recombinant variant AcrB polypeptide comprises proline at a position corresponding to amino acid 822. In some embodiments, the recombinant variant AcrB polypeptide comprises an amino acid residue other than a phenylalanine at a position corresponding to amino acid 927. In some embodiments, the recombinant variant AcrB-like polypeptide comprises a serine at a position corresponding to amino acid 927. In some embodiments, the recombinant variant AcrB polypeptide comprises an amino acid residue other than a phenylalanine at a position corresponding to amino acid 1033. In some embodiments, the recombinant variant AcrB polypeptide comprises a tyrosine at a position corresponding to amino acid 1033. In some embodiments, the recombinant variant AcrB polypeptide comprises an amino acid sequence of SEQ ID NO:1 or SEQ ID NO:5 in which one or more substitutions at amino acid positions corresponding to amino acids 279, 584, 617, 822, 927, or 1033 of SEQ ID NO:1 are substituted relative. In typical embodiments, the recombinant variant AcrB polypeptide reduces accumulation of alpha-olefin compounds in the host cell in comparison to a wild-type host cell that expresses native AcrB at a native level.

In a further aspect, the invention provides a recombinant variant AcrB-like polypeptide, wherein the recombinant variant AcrB polypeptide has at least 70% identity, or at least 80%, 85%, 90%, or 95% identity, to SEQ ID NO:2, SEQ ID NO:3, or SEQ ID NO:4 and comprises one or more amino acid substitutions within 2 to 8 Angstroms of, or at, a position corresponding to amino acid 279, amino acid 584, amino acid 617, amino acid 822, amino acid 927, or amino acid 1033, as numbered with reference to SEQ ID NO:1. In typical embodiments, the recombinant variant AcrB-like polypeptide reduces accumulation of alpha-olefin compounds, e.g., 1-hexene, in the host cell in comparison to a wild-type host cell that expresses a native AcrB-like polypeptide at a native level.

In a further embodiment, the invention provides a nucleic acid encoding a recombinant variant AcrB or AcrB-like polypeptide as described hereinabove and a microorganism host cell comprises the nucleic acid. The host cell may be a bacterial host cell, e.g., either a gram positive or gram negative host cell. In some embodiments, the host cell is a gram negative host cell, such as *E. coli*. In some embodiments, the host cell is a yeast host cell. In some embodiments, the host cell further comprises the proteins necessary to produce 1-hexene, or a derivative thereof.

In a further aspect the invention provides a me hod of producing an alpha-olefin compound comprising culturing a host cell as described herein above under conditions sufficient for the host cell to produce the alpha-olefin compound. In some embodiments, the alpha-olefin compound is hexene or a derivative of hexene. In some embodiments, the host cell produces a greater amount of the 1-hexene, or derivative thereof as compared to a wild-type host cell that expresses the native AcrB-like polypeptide at a natural level In a further aspect, the invention provides a method for producing an alpha-olefin compound, comprising: culturing a microorganism host cell that overexpresses an AcrB-like polypeptide under conditions sufficient for the host cell to produce the alpha-olefin compound, wherein the host cell produces a greater amount of the alpha-olefin compound compared to a corresponding host cell that expresses the native AcrB-like polypeptide at native levels. In some embodiments, the alpha-olefin compound is 1-hexene, or a derivative thereof. In some embodiments, the AcrB-like polypeptide has at least 70% identity, or at least 80%, 85%, 90%, or 95% identity, to the amino acid sequence of SEQ ID NO:1, SEQ ID NO:2, SEQ ID NO:3, SEQ ID NO:4 Of SEQ ID NO:5. In some embodiments, the AcrB-like polypeptide comprises the amino acid sequence of SEQ ID NO:1, SEQ ID NO:2, SEQ Ti) NO:3, SEQ ID NO:4 or SEQ ID NO:5. In some embodiments, the AcrB-like polypeptide comprises the amino acid sequence of SEQ ID NO:1 or SEQ ID NO:5. In some embodiments, the host cell is a bacterial host cell such as a gram negative or gram positive host cell. In some embodiments, the bacterial host cell is a gram negative cell, e.g., an $E.$ $coli$ host cell. In some embodiments, the host cell is a yeast host cell. In some embodiments, the host cell further comprises the proteins necessary to produce 1-hexene, or a derivative thereof.

In a further aspect, the invention provides a cell culture medium comprising an alpha-olefin compound and a microorganism host cell that overexpresses an AcrB-like polypeptide, wherein the host cell produces a greater amount of the alpha-olefin compound compared to a corresponding host cell that expresses the native AcrB-like polypeptide at native levels. In some embodiments, the alpha-olefin compound is 1-hexene, or a derivative thereof. In some embodiments, the AcrB-like polypeptide has at least 70% identity, or at least 80%, 85%, 90%, or 95% identity, to the amino acid sequence of SEQ ID NO:1, SEQ ID NO:2, SEQ ID NO:3, SEQ ID NO:4 or SEQ ID NO:5. In some embodiments, the AcrB-like polypeptide comprises the amino acid sequence of SEQ ID NO:1, SEQ ID NO:2, SEQ ID NO:3, SEQ ID NO:4 or SEQ ID NO:5. In some embodiments, the AcrB-like polypeptide comprises the amino acid sequence of SEQ ID NO:1 or SEQ ID NO:5. In some embodiments, the host cell is a bacterial host cell such as a gram negative of gram positive host cell. In some embodiments, the bacterial host cell is a gram negative cell, e.g., an $E.$ $coli$ host cell. In some embodiments, the host cell is a yeast host cell. In some embodiments, the host cell further comprises the proteins necessary to produce 1-hexene, or a derivative thereof.

BRIEF DESCRIPTION OF THE DRAWINGS

FIG. 8 provides an alignment of SEQ ID NOs:1, 2, 3, 4, and 5. Transmembrane domains and amino acids involved in binding or H+ transport are shown in SEQ ID NO:1. As understood in the art, not all of the amino acids of SEQ ID NOS: 2, 3, 4, and 5 are explicitly shown in the alignments to SEQ ID NO:1 so that the overall homologies of the sequences to SEQ ID NO:1 are more readily apparent.

DETAILED DESCRIPTION OF THE INVENTION

Figure 1:
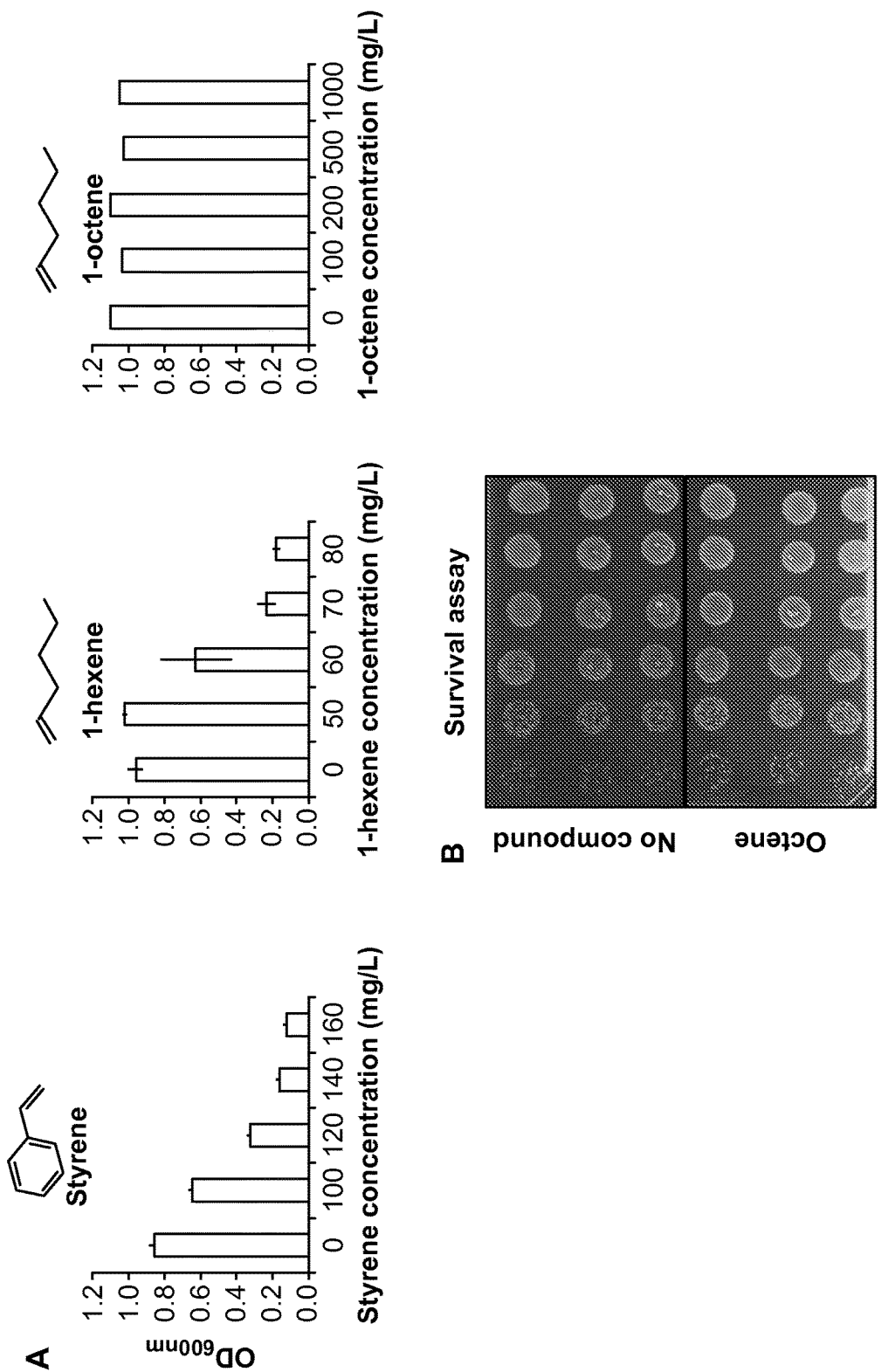
FIG. 1. Impact of styrene, 1-hexene and 1-octene on cell growth. A: The olefin compounds were added to different concentrations as indicated to an $E.$ $coli$ K12 culture at an $OD_{600}$=0.2. OD was monitored after 2 hour at 37° C. The bars represent standard deviation between duplicates B: A survival test in presence of 1-octene was performed. Six different dilutions of a culture (10 cells to $10^7$ cells, left to right) of $E.$ $coli$ K12 were spotted in triplicate on an agar plate. An overlay of 1-octene was added over the cells (controls had no overlay). Plates were incubated at room temperature for 2 days and then opened to allow evaporation of the olefin.

Before the present invention is described, it is to be understood that this invention is not limited to particular embodiments described, as such may, of course, vary. It is also to be understood that the terminology used herein is for the purpose of describing particular embodiments only, and is not intended to be limiting.

Definitions

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a". "and", and "the" include plural referents unless the context clearly dictates otherwise. Thus, for example, reference to "an efflux pump" includes a plurality of such efflux pumps; reference to a "host cell" includes a plurality of such host cells.

As used herein, the term "α-olefin-tolerant" or "alpha-olefin-tolerant" in the context of a host cell refers to a host cell that has been engineered to have an AcrB-like polypeptide, e.g. AcrB, that provides for increased survival of the host cell, i.e., the cell has increased tolerance, in the presence of an α-olefin, such as 1-hexene, compared to the counterpart host cell that produces the wild type AcrB-like polypeptide, e.g., wild type AcrB, at a native level, i.e., at a level that occurs in nature. As used herein, a host cell that is "more tolerant" to an α-olefin compound, e.g., 1-hexene, refers to a host cell that has increased α-olefin tolerance relative to the counterpart wild type host cell.

As used herein, the term "AcrB polypeptide" refers to an E. coli K12 AcrB membrane polypeptide comprising the amino acid sequence of SEQ ID NO:1, or a variant thereof, that functions as an efflux pump to transport compounds out of a host cell. An "AcrB polypeptide" in the context of the present invention has at least 65% identity, typically at least 70%, 75%, 80%, 85%, or 90% identity, or greater, e.g., 91%, 92%, 93%, 94%, 95%, 96%, 97%, 98% or 99% or greater, amino acid sequence identity, preferably over a region of at least about 100, 200, 300, 400, 500, 600, 700, 800, 900, or more amino acids, or over the total length of the polypeptide, to SEQ ID NO:1. A nucleic acid that encodes an AcrB polypeptide refers to a gene, cDNA, pre-mRNA, mRNA, and the like, including nucleic acids that encode variants of a naturally occurring AcrB amino acid sequence as described herein. AcrB polypeptide structure is well known (see, e.g., Husain and Nikaido 2010; Murakami et al. 2002). In the present invention, although an AcrB polypeptide can function as a component of a HAE1 family efflux pump, e.g., with AcrA and TolC, in some embodiments, an AcrB polypeptide functions independent of other HAE1 efflux pump components.

As used herein, the term "AcrF polypeptide" refers to an E. coli HAE1 family member membrane polypeptide comprising the amino acid sequence of SEQ ID NO:5 or a variant thereof, that functions as an efflux pump to transport compounds out of a host cell. An "AcrF polypeptide" in the context of the present invention has at least 65% identity, typically at least 70%, 75%, 80%, 85%, or 90% identity, or greater, e.g., 91%, 92%, 93%, 94%, 95%, 96%, 97%, 98% or 99% or greater, amino acid sequence identity, preferably over a region of at least about 100, 200, 300, 400, 500, 600, 700, 800, 900, or more amino acids, or over the total length of the polypeptide, to SEQ ID NO:5. A nucleic acid that encodes an AcrF polypeptide refers to a gene, cDNA, pre-mRNA, mRNA, and the like, including nucleic acids that encode variants of a naturally occurring AcrF amino acid sequence as described herein. HAE1 family polypeptide structure is well known (see, e.g., Husain and Nikaido 2010; Murakami et al. 2002, which provide an illustrative AcrB structure). In the present invention, although an AcrF polypeptide can function as a component of a HAE1 family efflux pump. e.g., AcrE and TolC, in some embodiments, an AcrF polypeptide functions independent of other HAE1 efflux pump components.

As used herein, the term "*Pseudomonas putida* KT2440 polypeptide NCBI NP_743544" refers to a *Pseudomonas putida* HAE1 family member membrane polypeptide comprising the amino acid sequence of SEQ ID NO:2, or a variant thereof, that functions as an efflux pump to transport compounds out of a host cell. A "*Pseudomonas putida* KT2440 polypeptide NCBI NP_743544" in the context of the present invention has at least 65% identity, typically at least 70%/0, 75%, 80%, 85%, or 90% identity, or greater, e.g., 91%, 92%, 93%, 94%, 95%, 96%, 97%, 98% or 99% or greater, amino acid sequence identity, preferably over a region of at least about 100, 200, 300, 400, 500, 600, 700, 800, 900, or more amino acids, or over the total length of the polypeptide, to SEQ ID NO:2. A nucleic acid that encodes a *Pseudomonas putida* KT2440 polypeptide NCBI NP_743544 refers to a gene, cDNA, pre-mRNA, mRNA, and the like, including nucleic acids that encode variants of a naturally occurring *Pseudomonas putida* KT2440 polypeptide NCBI NP_743544 amino acid sequence as described herein. HAE1 family polypeptide structure is well known (see, e.g., Husain and Nikaido 2010; Murakami et al. 2002, which describe AcrB structures). In the present invention, although a *Pseudomonas putida* KT2440 polypeptide NCBI NP_743544 polypeptide can function as a component of a HAE1 family efflux pump, in some embodiments, a *Pseudomonas putida* KT2440 polypeptide NCBI NP_743544 polypeptide functions independent of other HAE1 efflux pump components.

As used herein, the term "*Marinobacter aqueolei* EPL polypeptide NCBI YP_960752" refers to a *Marinobacter aqueolei* EPL HAE1 family member membrane polypeptide comprising the amino acid sequence of SEQ ID NO:3, or a variant thereof, that functions as an efflux pump to transport compounds out of a host cell. A *Marinobacter aqueolei* EPL polypeptide NCBI YP_960752" in the context of the present invention has at least 65% identity, typically at least 70%, 75%, 80%, 85%, or 90% identity, or greater, e.g., 91%, 92%, 93%, 94%, 95%, 96%, 97%, 98% or 99% or greater, amino acid sequence identity, preferably over a region of at least about 100, 200, 300, 400, 500, 600, 700, 800, 900, or more amino acids, or over the total length of the polypeptide, to SEQ ID NO:3. A nucleic acid that encodes a *Marinobacter aqueolei* EPL polypeptide NCBI YP_960752 refers to a gene, cDNA, pre-mRNA, mRNA, and the like, including nucleic acids that encode variants of a naturally occurring *Marinobacter aqueolei* EPL polypeptide NCBI YP_960752 amino acid sequence as described herein. HAE1 family polypeptide structure is well known (see, e.g., Husain and Nikaido 2010; Murakami et al. 2002, which describe AcrB structures). In the present invention, although a *Marinobacter aqueolei* EPL polypeptide NCBI YP_960752 can function as a component of a HAE1 family efflux pump, in some embodiments, a *Marinobacter aqueolei* EPL polypeptide NCBI YP_960752 functions independent of other HAE1 efflux pump components.

As used herein, the term "*Pseudoalteromonas haloplanktis* TAC125 polypeptide NCBI YP_341810" refers to a *Pseudoalteromonas haloplanktis* TAC125 HAE1 family member membrane polypeptide comprising the amino acid sequence of SEQ ID NO:4, or a variant thereof, that functions as an efflux pump to transport compounds out of a host cell. A "*Pseudoalteromonas haloplanktis* TAC125 polypeptide NCBI YP_341810" in the context of the present invention has at least 65% identity, typically at least 70%, 75%, 80%, 85%, or 90% identity, or greater, e.g., 91%, 92%, 93%, 94%, 95%, 96%, 97%, 98% or 99% or greater, amino acid sequence identity, preferably over a region of at least about 100, 200, 300, 400, 500, 600, 700, 800, 900, or more amino acids, or over the total length of the polypeptide, to SEQ ID NO:4. A nucleic acid that encodes a *Pseudoalteromonas haloplanktis* TAC125 polypeptide NCBI YP_341810 refers to a gene, cDNA, pre-mRNA, mRNA, and the like, including nucleic acids that encode variants of a naturally occurring *Pseudoalteromonas haloplanktis* TAC125 polypeptide NCBI YP_341810 amino acid sequence as described herein. HAE1 family polypeptide structure is well known (see. e.g., Husain and Nikaido 2010; Murakami et al. 2002, which describe AcrB structures). In the present invention, although a *Pseudoalteromonas haloplanktis* TAC125 polypeptide NCBI YP_341810 can function as a component of a HAE1 family efflux pump, in some embodiments, a *Pseudoalteromonas haloplanktis* TAC125 polypeptide NCBI YP_341810 functions independent of other HAE1 efflux pump components.

As used herein, the term "AcrB-like polypeptide" encompasses an *E. coli* AcrB polypeptide, an AcrF polypeptide, a *Pseudomonas putida* KT2440 polypeptide NCBI NP_743544, a *Marinobacter aqueolei* EPL polypeptide NCBI YP_960752, and a *Pseudoalteromonas haloplanktis* TAC125 polypeptide NCBI YP_341810, and variants of the polypeptide as described herein. An AcrB-like polypeptide has at least 50% amino acid sequence identity, or at least 55%, 60%, or 65% identity, preferably at least 70%, 75%, 80%, 85%, or 90% identity, or greater, e.g., 91%, 92%, 93%, 94%, 95%, 96%, 97%, 98% or 99% or greater, amino acid sequence identity, preferably over a region of at least about 100, 200, 300, 400, 500, 600, 700, 800, 900, or more amino acids, or over the total length of the polypeptide, to SEQ ID NO:1. A nucleic acid that encodes an AcrB-like polypeptide refers to a gene, cDNA, pre-mRNA, mRNA, and the like, including nucleic acids that encode variants of a naturally occurring AcrB, AcrF, *Pseudomonas putida* KT2440 polypeptide NCBI NP_743544, *Marinobacter aqueolei* EPL polypeptide NCBI YP_960752, or *Pseudoalteromonas haloplanktis* TAC125 polypeptide NCBI YP_341810 amino acid sequences described herein. AcrB polypeptide structure is well known (see. e.g., Husain and Nikaido 2010; Murakami et al. 2002). In the present invention, although an AcrB-like polypeptide can function as a component of a HAE1 family efflux pump, e.g., with AcrA and TolC, in some embodiments, AcrB-like polypeptides are used in embodiments in which the AcrB-like polypeptide functions independent of other HAE1 efflux pump components.

The terms "wild type", "native", "endogenous", and "naturally occurring" are used herein in the context of an AcrB-like polypeptide or polynucleotide to refer to an AcrB or AcrB homolog such as AcrF, *Pseudomonas putida* KT2440 polypeptide NCBI NP_743544, *Marinobacter aqueolei* EPL polypeptide NCBI YP_960752, or *Pseudoalteromonas haloplanktis* TAC125 polypeptide NCBI YP_341810, that is present in a Gram negative bacteria in nature.

A "variant" as used herein with respect to an AcrB-like polypeptide or AcrB-like polynucleotide; comprises one or more modifications relative to a native AcrB-like polypeptide or comprises one or more modifications relative to a native AcrB-like polynucleotide. Thus, a "variant" of an AcrB polypeptide or AcrB polynucleotide comprises one or more modifications relative to a native AcrB polypeptide or nucleic acid. Similarly, a "variant" with respect to an AcrF polypeptide or AcrF polynucleotide comprises one or more modifications relative to a native AcrF polypeptide or comprises one or more modifications relative to the native AcrF polynucleotide; and a "variant" with respect to a *Pseudomonas putida* KT2440 polypeptide NCBI NP_743544 or polynucleotide, *Marinobacter aqueolei* EPL polypeptide NCBI YP_960752 or polynucleotide, or *Pseudoalteromonas haloplanktis* TAC125 polypeptide NCBI YP_341810 or polynucleotide refers to a polypeptide that comprises one or more modifications relative to the native polypeptide or a polynucleotide that comprises one or more modifications relative to the native polynucleotide. Modifications include substitutions, insertions, deletions and/or truncations of one or more specific amino acid residues or of one or more specific nucleotides or codons in the polypeptide or polynucleotide.

In the context of this invention, the term "mutant" with respect to a mutant polypeptide or mutant polynucleotide is used interchangeably with "variant". A "non-naturally" occurring AcrB-like polypeptide refers to a variant or mutant AcrB-like polypeptide that is not present in a cell in nature and that is produced by genetic modification, e.g., using genetic engineering technology or mutagenesis techniques, of a native AcrB-like polynucleotide, such as a native AcrB or AcrF polynucleotide, or a native polynucleotide that encodes *Pseudomonas putida* KT2440 polypeptide NCBI NP_743544, *Marinobacter aqueolei* EPL polypeptide NCBI YP_960752, or *Pseudoalteromonas haloplanktis* TAC125 polypeptide NCBI YP_341810.

A "sequence mutation" in the context of the present invention refers to a substitution, deletion, or insertion of one more amino acids in an amino acid sequence in comparison to a native polypeptide.

The terms "numbered with reference to", or "corresponding to," or "determined with reference to" when used in the context of the numbering of a given amino acid sequence, refers to the numbering of the residues of a specified reference sequence when the given amino sequence is maximally aligned and compared to the reference sequence. For example, a residue in a variant AcrB-like polypeptide "corresponds to" an amino acid at a position in SEQ ID NO:1 when the residue aligns with the amino acid in a comparison of SEQ ID NO: and the variant protein.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press): positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The terms "peptide," "polypeptide" and "protein" are used interchangeably in the context of the present invention.

The term "substantially identical," used in the context of two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence, e.g., across a region of 500 amino acids or 750 amino acids or more, or across the length of, a reference sequence such as SEQ ID NO:1, or one of SEQ ID NOS:2 to 5 using the programs described herein; preferably BLAST using standard parameters.

Percent identity with respect to amino acid or nucleotide sequences is defined herein as the percentage of amino acid or nucleotide residues in the candidate sequence that are identical with the known polypeptides, after aligning the sequences for maximum percent identity and introducing gaps, if necessary, to achieve the maximum percent homology. Identity at the nucleotide or amino acid sequence level may be determined using methods known in the art, including but not limited to BLAST (Basic Local Alignment Search Tool) analysis using the algorithms employed by programs such as the BLAST programs blastp, blastn, blastx, tblastn and tblastx (Altschul (1997), Nucleic Acids Res. 25, 3389-3402, and Karlin (1990), Proc. Natl. Acad. Sci. USA 87, 2264-2268), which are tailored for sequence similarity/identity searching.

Nucleic acid or protein sequences that are substantially identical to a reference sequence include "conservatively modified variants." One of skill will recognize that individual substitutions, in a nucleic acid, peptide, polypeptide, or protein sequence that alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gin (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gin. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained: Ser for Thr or vice versa, such that a free —OH can be maintained; and Gln for Asn or vice versa, such that a free —NH2 can be maintained.

A polynucleotide or polypeptide is "heterologous" to an organism or a second polynucleotide or polypeptide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter. As an example of a "heterologous" sequence, an AcrB polypeptide containing an amino acid substitution with reference to SEQ ID NO:1 is heterologous to an *E. coli* host cell, as it has been modified from the native AcrB polypeptide sequence of SEQ ID NO:1.

A "host cell" as used herein refers to a cell that is genetically modified. The term includes a parental cell that is genetically modified as well as progeny and genetically modified derivatives. Genetic modification can be achieved by any suitable genetic engineering technique and/or mutagenesis techniques (e.g., chemical or UV mutagenesis and subsequent selection). Using recombinant technology, nucleic acid molecules can be introduced, deleted, inhibited or otherwise modified in the host cell. A "host cell" encompasses a cell from any prokaryote or eukaryote. A "microorganism host cell" as used here refers to a cell from a single-cell organism, e.g., a bacteria; a single-cell fungi, such as a yeast; an archaea, a cyanobacteria, and the like.

A "recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid. A polypeptide is "recombinant" when it is artificial or engineered, or derived from or contains an artificial or engineered protein. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant. A "recombinant" host cell contains a recombinant nucleic acid or recombinant protein.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA sequence if it stimulates or modulates the transcription of the DNA sequence in an appropriate host cell or other expression system.

Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. One example of an expression cassette is a polynucleotide construct that comprises a polynucleotide sequence encoding an AcrB-like polypeptide of the invention protein operably linked to a promoter, e.g., an inducible promoter, where the expression cassette is introduced into a microorganism, such as a bacterial cell. In some embodiments, an expression cassette comprises a polynucleotide sequence encoding an AcrB-like polypeptide of the invention, e.g., an AcrB variant, where the polynucleotide is targeted to a position in the genome of a microorganism such that expression of the polynucleotide sequence is driven by a promoter that is present in the microorganism. The promoter may be a native promoter, or a non-native promoter that has been introduced into the microorganism.

In instances when a NCBI/GenBank Accession No. (such as YP_957870) is employed to refer to the inner membrane protein of an efflux pump, it is understood in the art that the entire nucleotide sequence of the operon, and the known/deduced amino acid sequences of the proteins forming the efflux pump, are available from the literature, including the NCBI database available at the http www site for the ncbi, national library of medicine, national institutes of health-.gov.

This invention employs various routine recombinant nucleic acid techniques. Generally, the nomenclature and the laboratory procedures in recombinant DNA technology described below are well known and commonly employed in the art. Many manuals that provide direction for performing recombinant DNA manipulations are available, e.g., Sambrook & Russell, Molecular Cloning, A Laboratory Manual (3rd Ed, 2001): and Current Protocols in Molecular Biology (Ausubel, et al., John Wiley and Sons, New York, 2009, supplements through 2014).

Introduction

The present invention is based, in part, on the discovery of a mechanism for manipulating an efflux pump polypeptide to improve tolerance of a microorganism, such as a yeast or bacteria, towards α-olefin compounds, e.g., 1-hexene, or derivatives thereof, by genetically modifying an AcrB-like polypeptide, e.g., an AcrB polypeptide of SEQ ID NO:1. In some embodiments, the microorganism has improved tolerance to 1-hexene. In some embodiments, the microorganism has improved tolerance to 1-butene, 1-pentene, 1-heptene, or 1-octene. In some embodiments, the microorganism has improved tolerance to multiple α-olefin compounds, such as one or more of 1-hexene, 1-pentene, 1-butene, 1-heptene, or 1-octene. In some embodiments, the microorganism may also exhibit improved tolerance to compounds in addition to an α-olefin, for example, improved tolerance to a hydrocarbon such as pentane, hexane, heptane; or to an alcohol such as hexanol or heptanol as well as improved tolerance to the α-olefin.

In one aspect, the invention thus provides nucleic acids encoding non-naturally occurring AcrB-like polypeptide and recombinant host cells engineered to express such polypeptides. A microorganism modified to express a variant AcrB-like polypeptide as described herein can be employed in methods of producing an α-olefin, e.g., 1-hexene. The yield of the α-olefin is increased in comparison to the yield obtained from a corresponding microorganism that expresses the naturally occurring AcrB-like polypeptide, e.g., SEQ ID NO:1 or SEQ ID NO:5; or SEQ ID NO:2, 3, or 4, at native levels, i.e., the corresponding microorganism has not been engineered to express a variant AcrB-like polypeptide as described herein or engineered to overexpress a naturally occurring AcrB-like polypeptide.

In a further aspect, the invention also provides methods of producing α-olefin compounds, e.g., 1-hexene, using a host cell that has been genetically modified to overexpresses a naturally occurring AcrB-like polypeptide or a variant thereof at a level greater than the native amount of polypeptide produced by a counterpart host cell that does not have the genetic modification.

The following sections describe AcrB-like polypeptide and nucleic acid sequences in accordance with the invention, methods of engineering a microorganism to express the polypeptides, and methods of using such microorganism to produce an α-olefin, e.g., 1-hexene or 1-butene, 1-pentene, 1-heptene, or 1-octene.

AcrB-Like Polypeptide and Nucleic Acid Sequences

In one aspect, the invention provides nucleic acids encoding non-naturally occurring AcrB-like polypeptides and recombinant host cells engineered to express such polypeptides. Such polypeptides have one or more amino acid substitutions compared to a native AcrB-like polypeptide sequence, such as SEQ ID NO:1, SEQ ID NO:2, SEQ ID NO:3, SEQ ID NO:4, or SEQ ID NO:5.

In the context of the present invention, illustrative substitution mutations are typically described with reference to the *E. coli* K12 AcrB polypeptide sequence (SEQ ID NO:1): MPNFFIDRPIFAWVIAIIIMLAGGLAILKLPVAQYPTIAPPAVTISASYPGADAKTVQDT VTQVIEQNMNGIDNLMYMSSNSDSTGTVQITLTFESGTDADIAQVQVQNKLQLAMP LLPQEVQQQGVSVEKSSSSFLMVVGVINTDGTMTQEDISDYVAANMKDAISRTSGV GDVQLFGSQYAMRIWMNPNELNKFQLTPVDVITAIKAQNAQVAAGQLGGTPPVKG QQLNASIIAQTRLTSTEEFGKILLKVNQDGSRVLLRDVAKIELGGENYDIIAEFNGQPA SGLGIKLATGANALDTAAAIRAELAKMEPFFPSGLKIVYPYDTTPFVKISIHEVVKTLV EAIILVFLVMYLFLQNFRATLIPTIAVPVVLLGTFAVLAAFGFSINTLTMFGMVLAIGL LVDDAIVVVENVERVMAEEGLPPKEATRKSMGQIQGALVGIAMVLSAVFVPMAFFG GSTGAIYRQFSITIVSAMALSVLVALILTPALCATMLKPIAKGDHGEGKKGFFGWFNR MFEKSTHHYTDSVGGILRSTGRYLVLYLIIVVGMAYLFVRLPSSFLPDEDQGVFMTM VQLPAGATQERTQKVLNEVTHYYLTKEKNNVESVFAVNGFGFAGRGQNTGIAFVSL KDWADRPGEENKVEAITMRATRAFSQIKDAMVFAFNLPAIVELGTATGFDFELIDQA GLGHEKLTQARNQLLAEAAKHPDMLTSVRPNGLEDTPQFKIDIDQEKAQALGVSIND INTTLGAAWGGSYVNDFIDRGRVKKVYVMSEAKYRMLPDDIGDWYVRAADGQMV PFSAFSSSRWEYGSPRLERYNGLPSMEILGQAAPGKSTGEAMELMEQLASKLPTGVG YDWTGMSYQERLSGNQAPSLYAISLIVVFLCLAALYESWSIPFSVMLVVPLGVIGALL AATFRGLTNDVYFQVGLLTTIGLSAKNAILIVEFAKDLMDKEGKGLIEATLDAVRMR LRPILMTSLAFILGVMPLVISTGAGSGAQNAVGTGVMGGMVTATVLAIFFVPVFFVV VRRRFSRKNEDIEHSHTVDHH. Thus, where SEQ ID NO:1 is the reference sequence, the position designation of a mutated amino acid in a variant polypeptide aligned to the reference sequence is the number of the position in SEQ ID NO:1. Illustrative transmembrane domains of SEQ ID NO:1 and SEQ ID NO: amino acids identified from structural studies as being important for binding or for H+ transport are shown in FIG. 8. The positions of illustrative substitutions in SEQ ID NO:1 that improve tolerance are also shown in FIG. 8.

In some embodiments, an α-olefin-tolerant host cell comprises a nucleic acid that encodes a variant AcrB-like polypeptide that has an amino acid sequence that has at least 50% amino acid sequence identity, or at least 55%, 60%, 65%, 70%, 75%, 80%, 85%, 90%, preferably 91%, 92%, 93%, 94%, 95%, 96%, 97%, 98% or 99% or greater amino acid sequence identity over a region of at least 1,000 or more amino acids, or over the length of the entire polypeptide, to an amino acid sequence of SEQ ID NO:1, where the mutant protein confers tolerance to the host cell relative to a counterpart host cell that has not been modified to express the variant protein or to overexpress native AcrB polypeptide. In some embodiments, the variant AcrB-like polypeptide comprises one or more amino acid substitutions as determined with reference to SEQ ID NO:1. Thus, in some embodiments, the invention provides a variant AcrB-like polypeptide, wherein the variant polypeptide is substantially identical to SEQ ID NO:1 and has one or more amino acid substitutions at a position corresponding to residue 279, 584, 617, 822, 927, or 1033 of SEQ ID NO:1. In some embodiments, a polypeptide of the invention is at least 70% identical, or at least 80%, at least 85%, at least 90% or at least 95% identical, to SEQ ID NO:1 and has at least one amino acid substitution at a position corresponding to residue 279, 584, 617, 822, 927, or 1033 of SEQ ID NO:1. In some embodiments, a polypeptide of the invention is at least 70% identical, or at least 80%, at least 85%, at least 90% or at least 95% identical, to SEQ ID NO:1, and has an amino acid substitution, e.g., alanine to threonine, at a position corresponding to position 279 of SEQ ID NO:1. In some embodiments, a polypeptide of the invention is at least 70% identical, or at least 80%, at least 85%, at least 90% or at least 95% identical, to SEQ ID NO:1, and has an amino acid substitution, e.g., glutamine to arginine, at a position corresponding to position 584 of SEQ ID NO:1. In some embodiments, a polypeptide of the invention is at least 70% identical, or at least 80%, at least 85%, at least 90% or at least 95% identical, to SEQ ID NO:1, and has an amino acid substitution, e.g., phenylalanine to leucine, at a position corresponding to position 617 of SEQ ID NO:1. In some embodiments, a polypeptide of the invention is at least 70% identical, or at least 80%, at least 85%, at least 90% or at least 95% identical, to SEQ ID NO:1, and has an amino acid substitution, e.g., leucine to proline, at a position corresponding to position 822 of SEQ ID NO:1. In some embodiments, a polypeptide of the invention is at least 70% identical, or at least 80%, at least 85%, at least 90% or at least 95% identical, to SEQ ID NO:1, and has an amino acid substitution, e.g., phenylalanine to serine, at a position corresponding to position 927 of SEQ ID NO:1. In some embodiments, a polypeptide of the invention is at least 70% identical, or at least 80%, at least 85%, at least 90% or at least 95% identical, to SEQ ID NO:1, and has an amino acid substitution, e.g., from phenylalanine to tyrosine, at a position corresponding to position 1033 of SEQ ID NO:1.

In further embodiments, an AcrB-like polypeptide in accordance with the invention has at least two amino acid substitutions, or at least three amino acid substitutions, selected from positions 279, 584, 617, 822, 927 and 1033, as numbered with reference to SEQ ID NO:1. In some embodiments, an AcrB-like polypeptide in accordance with the invention has 3 or fewer substitutions at positions 279, 584, 617, 822, 927, or 1033 as numbered with reference to SEQ ID NO:1.

In some embodiments, an AcrB-like polypeptide in accordance with the invention has a mutation, typically a substitution, at a residue that is in close proximity, e.g., within 2 to within 8 Angstroms, or in some embodiments, within 2 to 5 Angstroms or 2 to 6 Angstroms, with respect to the secondary structure of the AcrB-like polypeptide, to one of residues 279, 584, 617, 822, 927, and 1033 as numbered with reference to SEQ ID NO:1. The structure of the AcrB polypeptide has been well characterized (see, e.g., Murakami et al, 2002 and additional references cited in the Examples section). One of skill can thus identify residues that are in close proximity and of likely functional relevance. For example, in some embodiments, a variant AcrB-like polypeptide conferring increased tolerance of a host cell to an α-olefin may have a mutation, e.g., a substitution, at a position in close proximity to residue 279, e.g., at a position corresponding to residue 141, 151, 178, 179, 277, 278, 280, 281, 283, 284, 285, 286, 287, 288, 610, 611, 612, 613, or 614 as numbered with reference to SEQ ID NO:1. In some embodiments, the position in close proximity to residue 279 is within 3 to 5 Angstroms and corresponds to position 178, 278, 280, 285, 286, 287, or 612 as numbered with reference to SEQ ID NO:1. In some embodiments, a variant AcrB-like polypeptide conferring increased tolerance of a host cell to an α-olefin may have a mutation. e.g., a substitution, at a position in close proximity to residue 584, e.g., at a position corresponding to residue 275, 276, 277, 278, 582, 583, 585, 586, 587, 588, 589, 613, 614, 621, 622, or 623 as numbered with reference to SEQ ID NO:1. AcrB functions as a trimer; thus in some embodiments, a residue in close proximity to residue 584, e.g., at a position corresponding to residue 220, 221, 222, 223, 228, 229, or 231 as determined with reference to SEQ ID NO:1, is present in another AcrB polypeptide molecule that is part of the trimer. In some embodiments, the position in close proximity to residue 584 is within 3 to 6 Angstroms and corresponds to position 222, 223, 275, 276, 277, 278, 582, 583, 585, 586, 587, 588, 613, 614, or 622 as numbered with reference to SEQ ID NO:1. In some embodiments, the position in close proximity to residue 584 is within 3 to 5 Angstroms corresponds to residue 222, 276, 277, 278, 583, 585, 586, 587, 588, or 622 as numbered with reference to SEQ ID NO:1. In some embodiments, a variant AcrB polypeptide conferring increased tolerance of a host cell to an α-olefin may have a mutation, e.g., a substitution, at a position in close proximity to residue 617, e.g., at a position corresponding to residue 134, 135, 136, 573, 575, 615, 616, 618, 619, 620, 624, 625, or 626 as numbered with reference to SEQ ID NO:1. In some embodiments, the position in close proximity to residue 617 is within 3 to 6 Angstroms and corresponds to residue 134, 135, 136, 615, 616, 618, or 619 as numbered with reference to SEQ ID NO:1. In some embodiments, the position in close proximity to residue 617 is within 3 to 5 Angstroms and corresponds to residue 616, 618, or 619 as numbered with reference to SEQ ID NO:1. In some embodiments, a variant AcrB-like polypeptide conferring increased tolerance of a host cell to an α-olefin may have a mutation, e.g., a substitution, at a position in close proximity to residue 822, e.g., at a position corresponding to residue 79, 80, 160, 161, 165, 313, 685, 686, 687, 688, 689, 817, 818, 819, 820, 821, 823, 824, or 825 as numbered with reference to SEQ ID NO:1. In some embodiments, the position in close proximity to residue 822 is within 3 to 5 Angstroms and corresponds to residue 687, 818, 819, 820, 821, 823, or 824 as numbered with reference to SEQ ID NO:1. In some embodiments, a variant AcrB-like polypeptide conferring increased tolerance of a host cell to an α-olefin may have a mutation, e.g., a substitution, at a position in close proximity to residue 927, e.g., at a position corresponding to residue 556, 559, 561, 909, 912, 913, 914, 915, 916, 917, 921, 922, 923, 924, 925, 926, 928, 929, 930, 931, 932, 933, 1002, 1003, 1005, 1006, or 1007 as numbered with reference to SEQ ID NO:1. In some embodiments, the position in close proximity to residue 927 is within 3 to 5 Angstroms and corresponds to residue 912, 913, 923, 924, 925, 926, 928, 929, 930, 931, or 1006 as numbered with reference to SEQ ID NO:1. In some embodiments, a variant AcrB-like polypeptide conferring increased tolerance of a host cell to an α-olefin may have a mutation. e.g., a substitution, at a position in close proximity to residue 1033, e.g., at a position corresponding to residue 896, 953, 958, 959, 960, 961, 963, 1028, 1029, 1030, 1031, 1032, 1034, 1035, or 1036 as numbered with reference to SEQ ID NO:1. In some embodiments, the position in close proximity to residue 1033 is within 3 to 5 Angstroms and corresponds to residue 894, 895, 896, 960, 1031, 1032, 1034, 1035, or 1036 as numbered with reference to SEQ ID NO:1.

In addition, based on the structural information available, one of skill can additionally identify residues of an AcrB-like polypeptide that would likely be tolerant to substitution. For example, an AcrB-like polypeptide variant having a mutation at one or more positions corresponding to 279, 584, 617, 822, 927 or 1033 of SEQ ID NO:1 may comprise substitutions at other positions that do not have an effect on the ability of the polypeptide to confer α-olefin tolerance to a host cell and do not otherwise impair pump activity. Accordingly, one of skill can identify variant AcrB-like polypeptides having a mutation described herein and the specified percent identity to the reference sequence, e.g., SEQ ID NO:1, that would retain the desired function.

In additional embodiments, a mutation as described herein can be introduced in an AcrB-like polypeptide that has another mutation in a domain that enhances efflux of a compound, for example at a site for enlargement in the entrance of the cleft that facilitates conformational changes or improve the affinity for the substrate (Fisher et al. 2013; Foo and Leong 2013).

In some embodiments, an AcrB-like polypeptide of the invention is a homolog of an *E. coli* AcrB efflux protein that is modified at a site corresponding to one or more of positions 279, 584, 617, 822, 927 or 1033 of SEQ ID NO:1, to improve tolerance of an organism to an α-olefin. For example, *Pseudomonas putida* KT2440 polypeptide NCBI NP_743544, *Marinobacter aqueolei* EPL NCBI YP_960752, and *Pseudoalteromonas haloplanktis* TAC125 NCBI YP_341810 have AcrB homologs designated by the accession number provided in parenthesis. The polypeptide sequences are shown in SEQ ID NOS:2, 3, and 4. These homologs have 66%, 59%, and 62% identity, respectively, to AcrB SEQ ID NO:1 when the full-length sequences are aligned. One or more mutations, e.g., a substitution at one or more positions selected from the positions in SEQ ID NO:2, 3, or 4 corresponding to a position within 2 to 8 Angstroms, or at, positions 279, 584, 617, 822, 927 or 1033 of SEQ ID NO:1, may be introduced into such homologs to obtain a variant that confers α-olefin tolerance, e.g., 1-hexene tolerance, to a host cell. Further, one of skill understands that a structural model of an AcrB homlog such as SEQ ID NO:2, 3, or 4 can be generated and compared to the structure of AcrB to determine residues of SEQ ID NOS:2, 3, or 4 that correspond to the regions within 2 to 8 Angstroms of positions 279, 584, 617, 822, 927 or 1033 of SEQ ID NO:1. Such modified homologs may contain other mutations, e.g., conservative substitutions, relative to the native sequence that do not have an effect on ability of the polypeptide to confer α-olefin tolerance to a host cell and do not otherwise impair pump activity.

In some embodiments, a native AcrB-like polypeptide modified in accordance with the invention to obtain a variant that confer α-olefin tolerance, e.g., 1-hexene tolerance, to a host cell is *E. coli* AcrF (SEQ ID NO:5), which has 78% identity to SEQ ID NO:1. Thus, in some embodiments, an AcrB-like polypeptide of the invention may be a variant of SEQ ID NO:5 that has one or more substitutions at position 279, 584, 617, 734, 822, 927, or 1033 as numbered with reference to SEQ ID NO:1, i.e., at position 279, 583, 616, 733, 821, 926, or 1032 of SEQ ID NO:5; or at one or more positions within 2 to 8 Angstroms of position 279, 583, 616, 821, 926, or 1032 of SEQ ID NO:5. Such modified homologs may contain other mutations, e.g., conservative substitutions, relative to the native sequence that do not have an effect on ability of the polypeptide to confer α-olefin tolerance to a host cell and do not otherwise impair pump activity.

In a further aspect, the invention also provides a host cell that is modified to overexpress an AcrB-like polypeptide to confer α-olefin tolerance to the host cell. Such a host cell can be used to produce the α-olefin. For example, a host cell can be modified to overexpress a native AcrB-like polypeptide, e.g., a polypeptide comprising the amino acid sequence of SEQ ID NO:1, SEQ ID NO:2, SEQ ID NO:3, SEQ ID NO:4, or SEQ ID NO:5. In some embodiments, a host cell can be modified to overexpress a variant AcrB-like polypeptide. In some embodiments, a host cell may be modified to overexpress an AcrB polypeptide of SEQ ID NO:1. In some embodiments, a host cell may be modified to overexpress a native AcrB-like homolog polypeptide, such as an AcrB-like polypeptide of SEQ ID NO:2, 3, or 4. In some embodiments, a host cell may be modified to over express a native AcrF polypeptide of SEQ ID NO:5.

In the context of this invention, the product of a gene is considered to be overexpressed when the level of protein is increased by at least 5%, at least 10%, at least 20%, at least 30%, or at least 50% or greater in comparison to the natural level of AcrB or AcrB-like polypeptide that is produced by a counterpart wild type host cell of the same genetic background that has not been genetically modified to overexpress the protein.

An α-olefin-tolerant host cell of the present invention typically exhibits at least 5%, more often at least 10%, at least 15%, at least 20%, at least 25%, or at least 50%, or greater survival compared to the counterpart host cell that comprises a wild type AcrB or AcrB-like polypeptide expressed at natural levels when tested in the presence of an α-olefin, e.g., 1-hexene.

Tolerance to an α-olefin, e.g., 1-hexene, can be assessed using known assays. For example, a gene encoding a variant of an AcrB polypeptide of SEQ ID NO:1 can be introduced into a host cell, e.g., a bacterial host cell such as *E. coli*, and survival of the host cell in the presence of an α-olefin can be assessed. Illustrative assays are provided in the Examples section. In one illustrative assay, a plasmid-borne nucleic acid sequence encoding an AcrB-like variant polypeptide (along with a wild-type copy of acrA) is introduced into a ΔacrAB *E. coli* host cell and colonies are selected and grown overnight. A control strain may comprise a plasmid-borne copy of a nucleic acid sequence encoding the native acrB sequence (along with a wild type copy of acrA). In this example, the polynucleotide encoding the AcrB sequence is operably linked to an inducible promoter, such as a lac-inducible promoter. Dilutions are then prepared and the cells are plated onto agar plates with 1-hexene exposure using sufficient 1-hexene to saturate the atmosphere and expression of the variant protein (or for the control, wild type protein) is induced. An α-olefin tolerant strain expressing an AcrB-like variant shows greater growth in the presence of 1-hexene relative to strains expressing the wild type (control) sequence of AcrB at native levels. This phenomenon is more readily observed at lower cell dilutions in this assay.

Nucleic Acids Encoding a Variant Polypeptide

Isolation or generation of polynucleotide sequences to express a variant AcrB-like, polypeptide and/or to overexpress a native AcrB-like polypeptide of the invention can be accomplished by any number of techniques well known in the art, e.g. using PCR as described herein. The sequences of native AcrB-like nucleic acids are known in the art and can be obtained using the protein accession numbers and sequences provided herein. Appropriate primers and probes can be generated from comparisons of the nucleic acid sequences to amplify a nucleic acid encoding the polypeptide sequence of interest. Alternatively, a library can be screened to obtain a nucleic acid encoding the polypeptide. A desired mutation can be introduced into a sequence using known techniques, e.g., PCR followed by assembly of the gene by overlap extension.

Alternatively, a nucleic acid sequence encoding a non-naturally occurring AcrB-like polypeptide that confers enhanced α-olefin tolerance to a host cell can be generated using mutagenesis. For example, in some embodiments, one of skill can prepare a library of variants of an acrB gene, e.g., by error prone PCR, and introduce the library into host cells, such as an *E. coli*. Transformants can then be evaluated for tolerance to an α-olefin and evaluated to identify mutations in the acrB gene that conference tolerance.

Nucleic acid sequences encoding an AcrB-like polypeptide that confers increased α-olefin tolerance, e.g., increased 1-hexene tolerance, to a host cell, may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See, e.g., See e.g., Henaut and Danchin in "*Escherichia coli* and *Salmonella*," Neidhardt, et al. Eds., ASM Pres, Washington D.C. (1996), pp. 2047-2066; Nucleic Acids Res. 20:2111-2118; Nakamura et al., 2000, Nucl. Acids Res. 28:292.

Preparation of Recombinant Expression Constructs

To use isolated sequences in the above techniques, recombinant DNA vectors suitable for transformation of host cells are prepared. Preparation of recombinant vectors is well known in the art. For example, a DNA sequence encoding an AcrB-like polypeptide of the invention can be combined with transcriptional and other regulatory sequences that direct the transcription of the sequence from the gene in the intended cells. Control elements include promoters, optionally containing operator sequences, and other elements depending on the nature of the host. In some embodiments, an expression vector that comprises an expression cassette that comprises the gene also comprises a promoter operably linked to the gene. Such a promoter can be a promoter from a native gene that encodes AcrB or an AcrB homolog or can be a heterologous promoter. In other embodiments, a promoter and/or other regulatory elements that direct transcription of the gene are endogenous to the microorganism and an expression cassette comprising the gene encoding the AcrB-like polypeptide is introduced, e.g., by homologous recombination, such that the heterologous gene is operably linked to an endogenous promoter and expression is driven by the endogenous promoter. In some embodiments, a promoter that is endogenous microorganism can also be genetically modified or replaced to enhance production of an AcrB-like polypeptide when the polynucleotide encoding the AcrB-like polypeptide is integrated in a host chromosome at a position such that the polynucleotide is operably linked to the promoter.

As noted above, expression of the gene encoding an AcrB-like polypeptide can be controlled by a number of regulatory sequences including promoters, which may be either constitutive or inducible; and, optionally, repressor sequences. Examples of suitable promoters, especially in a bacterial host cell, are the promoters obtained from the *E. coli* lac operon and other promoters derived from genes involved in the metabolism of other sugars, e.g., galactose and maltose. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra.

Suitable promoters of use in a yeast host cell include promoters obtained from the genes for *Saccharomyces cerevisiae* enolase (ENO-1), *Saccharomyces cerevisiae* galactokinase (GAL 1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TP1), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488 or are otherwise known in the art.

An expression vector may also comprise additional sequences that influence expression of a gene encoding the AcrB-like polypeptide. Such sequences include enhancer sequences, a ribosome binding site, or other sequences such as transcription termination sequences, and the like.

A vector expressing a nucleic acid encoding an AcrB-like polypeptide of the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism. e.g., a bacterial cell such as *E. coli*. Suitable markers for other microbial host cells, such as yeast host cell are also well known and include, for example, ADE2, HIS3, LEU2, LYS2, MET3, TRP1, and URA3.

Although any suitable expression vector may be used to incorporate the desired sequences, readily available bacterial expression vectors include, without limitation: plasmids such as pSCIO1, pBR322, pBBR1MCS-3, pUR, pEX, pMR1OO, pCR4, pBAD24, pUC19, or plasmids derived from these plasmids; and bacteriophages, such as M1 3 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

A nucleic acid encoding an AcrB-like polypeptide may optionally also be introduced into a host cell that expresses other components of an AcrAB-TolC efflux pump, or homologous tripartite pump. However, in some embodiments, an AcrB-like polypeptide functions independent of the tripartite pump. Accordingly, the AcrA and TolC, or the homologs of AcrA and TolC, need not expressed in the host cell.

In some embodiments, the invention provides methods of producing an α-olefin compound, e.g., 1-hexene, wherein the method employ a host cell, e.g., *E. coli*, genetically modified to overexpress a naturally occurring AcrB or AcrB-like polypeptide, such as a polypeptide having a sequence of any one of SEQ ID NOS:1, 2, 3, 4, or 5, or a variant thereof. Such host cells can be obtained using known methods, such as those detailed above, for generating a construct comprising a nucleic acid encoding the naturally occurring AcrB or AcrB-like polypeptide that can be introduced into a host cell and expressed at the desired level.

In some embodiments, a promoter that influences expression of the native AcrB or AcrB-like polypeptide may be modified to increase expression. For example, an endogenous AcrB promoter may be replaced by a promoter that provides for increased expression compared to the native AcrB promoter.

In alternative embodiments, such a host cell that overexpresses a naturally occurring AcrB or AcrB-like polypeptide can be obtained by other techniques, e.g., by mutagenizing a microorganism, e.g., *E. coli* cells, and screening cells to identify a cell that expresses the native AcrB or AcrB-like polypeptide, e.g., SEQ ID NO:1, 2, 3, 4, or 5, at a level higher than native (e.g., at a level greater than that produced by the counterpart cell prior to mutagenesis).

Host Cells

The present invention provides for a modified host cell comprising a nucleic acid encoding any non-naturally occurring variant AcrB-like polypeptide as described herein. Further, the invention provides a genetically modified host cell that overexpresses a native AcrB polypeptide compared to counterpart host cells that express native levels of native AcrB; or that overexpresses a native AcrF or AcrB homolog *Pseudomonas putida* KT2440 polypeptide NCBI NP_743544, *Marinobacter aqueolei* EPL polypeptide NCBI YP_960752, or *Pseudoalteromonas haloplanktis* TAC125 polypeptide NCBI YP_341810 compared to counterpart host cells that express native levels of the native AcrF or AcrB homolog.

In some embodiments, a host cell has further genetic modifications. For example, in some embodiments, an *E. coli* host cell may have a deletion of an endogenous acrB gene or acrAB gene locus, or an alternative bacterial host cell may have a deletion of a homologous gene or gene locus that corresponds to acrB or AcrAB.

In some embodiments, a host cell is genetically engineered to produce an α-olefin of interest, e.g., 1-hexene, or a derivative of the α-olefin. Thus, for example, a host cell may be engineered to express one or more genes that encode enzymes for production of an α-olefin compound, e.g., a C5-C12, α-olefin compound such as pentene or hexene (see, e.g., WO/2012/050931, WO/2012/109601, each incorporated by reference).

A host cell comprising an AcrB-like polypeptide as described herein is typically a microorganism, such as a bacterial or yeast host cell. In some embodiments, the host cell is a bacterial host cell, such as a Gram-negative bacterial host cell. Alternatively, the bacterial host cell need not be Gram-negative. In some embodiments of the invention, the host cell is a proteobacteria. In some embodiments of the invention, the bacterium is any bacterium that produces an α-olefin. In some embodiments of the invention, the bacterium is an enteric bacterium. In some embodiments of the invention, the bacterium is a species of the genus *Planctomyces, Bradyrhizobium, Rhodobacter, Rhizobium, Myxococcus, Klebsiella, Azotobacter, Escherichia, Salmonella, Pseudomonas, Caulobacter, Chlamydia, Acinetobacter, Acetobacter, Enterobacter, Sinorhizobium, Vibrio,* or *Zymomonas.* In some embodiments, the host cell is *E. coli.* In some embodiments, the host cell is *Pseudomonas putida*, e.g., *Pseudomonas putida* KT2440; *Marinobacter aqueolei*, e.g., *Marinobacter* aqueolei EP; *Pseudoalteromonas haloplanktis. Pseudoalteromonas haloplanktis* TAC125, or *Zymomonas mobilis.* In some embodiments, the host cells include species assigned to *Azotobacter, Erwinia. Bacillus, Clostridium, Enterococcus, Lactobacillus, Lactococcus, Oceanobacillus, Proteus, Serratia, Shigella, StaphLococcus, Streptococcus, Streptomyces, Vitreoscilla, Synechococcus, Synechocystis,* and *Paracoccus* taxonomical classes. In some embodiments, the host cells are cyanobacteria.

In some embodiments, the host cell is a yeast. Examples of yeast host cells include, without limitation, *Candida, Hansenula, Kluveromvces, Pichia, Saccharomyces, Schizosaccharomyces,* or *Yarrowia* host cells. In some embodiments, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In some embodiments, the yeast host cell is a *Kluyveromyces lactis* cell. In another embodiment, the yeast host cell is a *Yarrowia lipolytica* cell.

Screening of Host Cells for α-Olefin Tolerance

Host cells can be screened for tolerance to an α-olefin as described herein. In a further aspect, the invention provides methods of screening for α-olefin-tolerant host cells.

In one embodiment, a high-throughput screening assay can be employed to evaluate α-olefin tolerance of a library of candidate cells that have been genetically modified, e.g., by mutagenesis of an AcrB-like gene. In this embodiment, following transformation of a library, prepared in a vector where expression of the AcrB-like gene is under control of an inducible promoter, into suitable host cells, e.g., *E. coli* K12 ΔacrAB, colonies are collected and inoculated into a small volume liquid culture, e.g., 96 deep well plates, and cultured for sufficient time to allow the cells to reach stationary phase, e.g., overnight at 37° C. with agitation. Cells are then diluted, e.g., 100-fold, and an aliquot of the dilution is spotted onto growth medium agar plates supplemented with an inducer and exposed to 1-hexene. Exposure to 1-hexene is performed by saturating the atmosphere. This assay also preferably comprises a step in which duplicate plates are not exposed to 1-hexene. Growth of various dilutions of the cells can then be monitored to determine whether the cells exhibit increased tolerance to 1-hexene compared to control cells that have a wild type AcrB-like gene, or that have not been mutagenized. Colonies that exhibit increased growth in the presence of 1-hexene compared to the control cells exposed to 1-hexene are then selected and further evaluated. Optionally, the screening method may further comprise a "pre-screen" step in which library transformants are initially plated onto agar plates containing an inducer and are assessed for growth in the presence or absence of a saturating atmosphere of 1-hexene. Colonies that grow in the presence of 1-hexene compared to a control may then be selected, grown in a liquid culture, and the dilution analysis screening assay performed.

Methods of Producing an α-Olefin

A host cell comprising a variant AcrB-like polypeptide of the invention and/or that overexpresses an AcrB-like polypeptide, such as a native AcrB polypeptide or native AcrB polypeptide homolog, e.g., a native polypeptide having a sequence of SEQ ID NO:1, 2, 3, 4, or 5, can be employed to produce an α-olefin compound or a derivative of an α-olefin compound. In some embodiments, the host cell produces 1-hexene; or 1-butene, 1-pentene, 1-heptene, or 1-octene. To produce the α-olefin, a host cell genetically modified to express an AcrB-like polypeptide as described herein can be cultured under conditions suitable to allow expression of the polypeptide and expression of genes that encode the enzymes that are used to produce the α-olefin or a derivative of the α-olefin. A host cell modified to express an AcrB-like polypeptide as described herein provides a higher yield of α-olefin relative to a non-modified counterpart host cell that expresses a native AcrB or AcrB homolog at native levels. A host cell modified to overexpress a native AcrB or AcrB homolog such as a polypeptide having the amino acid sequence of SEQ ID NO:1, 2, 3, 4 or 5, also provides a higher yield of α-olefin relative to a non-modified counterpart host cell that expresses a polypeptide comprising SEQ ID NO:1, 2, 3, 4, or 5 at native levels.

The α-olefin can then be separated and purified using known techniques. As used herein, the term "purify," "purified," or "purification" means the removal or isolation of a molecule from its environment by, for example, isolation or separation from the cells and/or cell culture medium that is producing the α-olefin. As used herein, "purified" also refer to the removal of contaminants from a sample. For example, when α-olefins are produced in a host cell, the α-olefins can be purified by the removal of host cell proteins.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

Example 1. Toxicity of Olefins and AcrB Involvement

Toxicity of Olefins, and AcrB Involvement.

Figure 2:
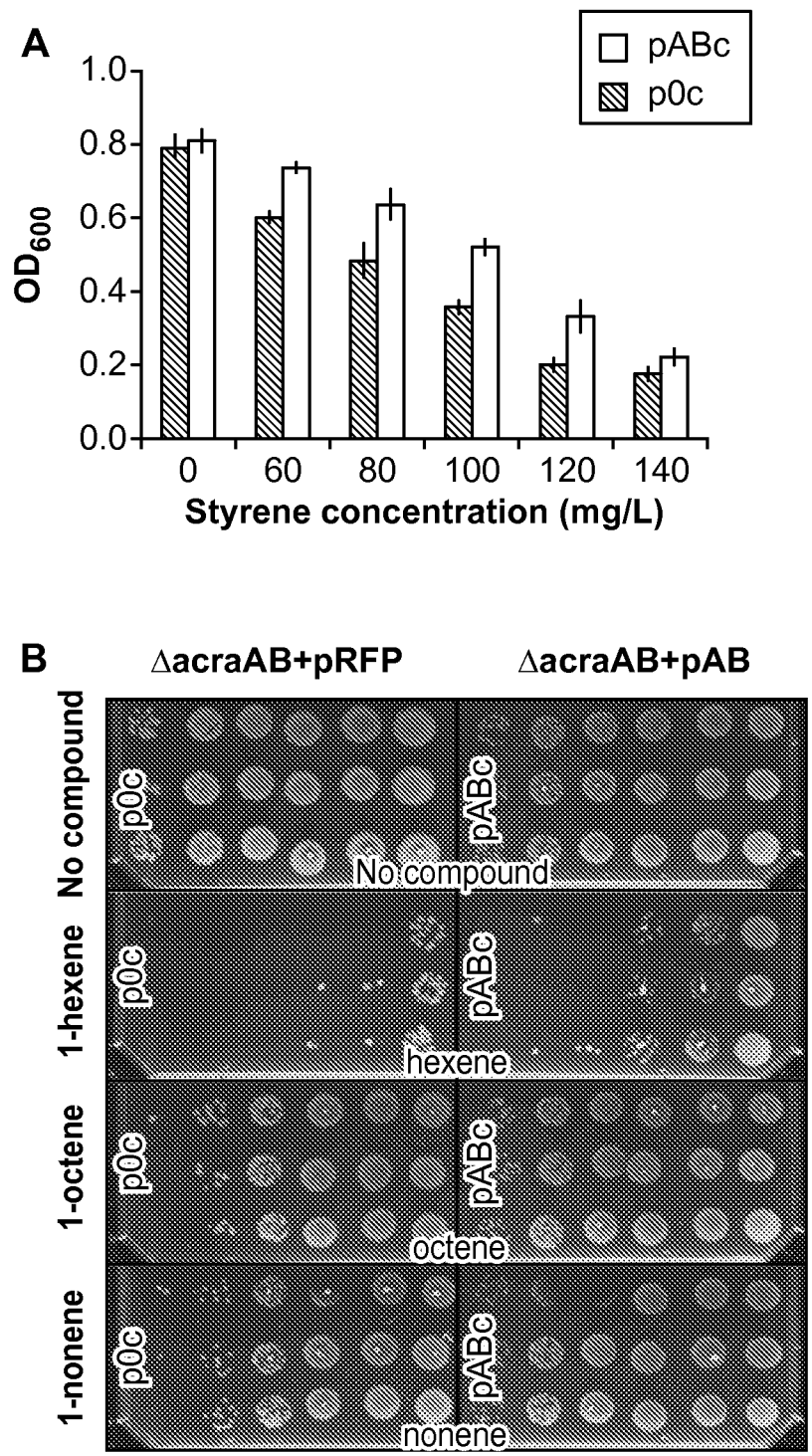
FIG. 2: impact of AcrAB production on growth, in presence of styrene 1-hexene, 1-octene and 1-nonene on cell growth. A: Different concentrations of styrene were added to an $OD_{600}$=0.2 culture of $E.$ $coli$ K12 ΔacrAB containing the pABc (white) or the control plasmid p0c (black). OD density was monitored after 2 hours of growth at 37° C. The bars represent standard deviation between duplicates. B: A survival test in presence of 1-hexene, 1-octene, or 1-nonene saturated atmosphere was performed. Six different dilutions of cultures (10 cells to $10^7$ cells, left to right on the figure) were spotted in triplicate on an agar plates. Plates were then exposed to the aforementioned chemicals.

In this example, toxicity of olefin compounds was evaluated. A toxic dose was defined as the concentration of compound that decreased growth by half. This concentration for E. coli K12 is 65 mg/L, 110 mg/L and >1 g/L for 1-hexene, styrene and 1-octene, respectively (FIG. 1A) for the media and growth conditions used. The compound 1-octene is less toxic than the two other olefins tested (FIG. 1B). The involvement of the tripartite pump, AcrAB-TolC in styrene or alpha-olefin tolerance was then assessed. AcrA and acrB mutants (E. coli K12 ΔacrAB) were constructed and transformed into a strain with a plasmid-borne acrA and acrB in an operon under the control of an arabinose inducible promoter (pABc) or a control plasmid (p0c). Exogenously added styrene was tested in liquid culture (FIG. 2A). The E. coli K12 ΔacrAB cells transformed to express AcrA and AcrB exhibited enhanced survival in the presence of styrene compared to those E. coli K12 ΔacrAB cells transformed with the control plasmid. A survival assay on agar plate in an atmosphere saturated with the volatile compound was developed for 1-hexene, 1-octene, and 1-nonene. For 1-hexene, 1-octene, and 1-nonene, the expression of the pump gave a strong advantage in the survival and growth of the strain (FIG. 2B).

AcrAB Involvement on Olefin Production.

Among olefins used for plastic production, styrene is the only one that has been reported to be produced at levels that high enough to pose toxicity to E. coli growth (McKenna et al, 2011). Accordingly, the involvement of the AcrAB-TolC tripartite pump in cells that produced styrene was evaluated. AcrAB was deleted in the L-phenylalanine overproducing E. coli strain (E. coli NST74 ΔacrAB) and then introduced on a plasmid with the plasmid encoding the styrene production genes. Two different IPTG induced promoters for fdc1 and pal1 (Ptrc, a strong promoter and PlacUV5, a weak promoter, respectively) were used to generate $p_{trc}$Sty and $p_{lac}$Sty. These plasmids, and the corresponding control plasmids ($p_{trc}$0 and $p_{lac}$0) were introduced in the strain containing plasmids encoding the pump (pABc and control, p0c). It was found that acrAB was important for growth, and consequently production, in the styrene production strain. The absence of the pump had a small negative impact on growth when styrene production was not induced, however, the absence of the pump had a strong negative impact when styrene production was induced. Further, the quantity of styrene produced by the cells was significantly higher when the pump-containing plasmid was present. These data thus further confirmed that AcrAB-TolC played an important role in growth in the presence of a toxic compound such as styrene.

Improvement of Tolerance by Pump Overproduction.

Figure 3:
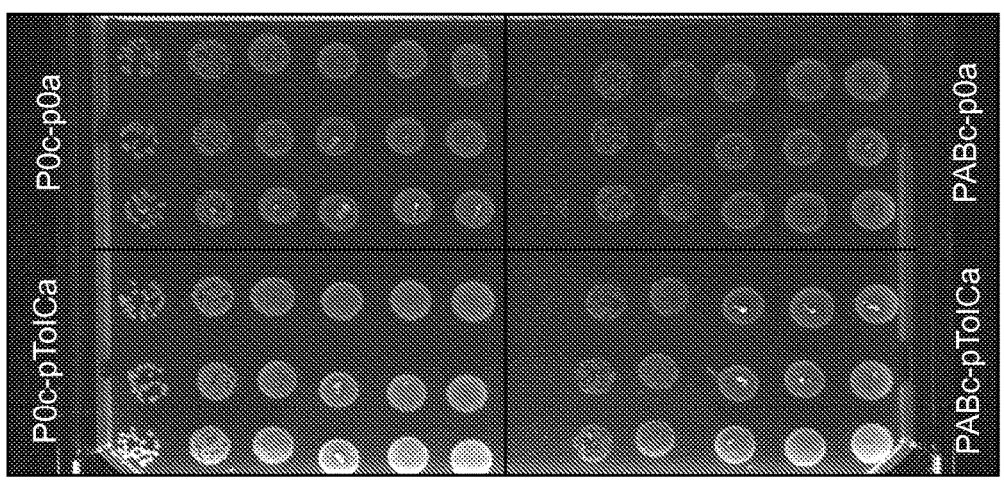
FIG. 3: impact of over-production of AcrA, AcrB and TolC on tolerance to 1-hexene. A. Survival tests of $E.$ $coli$ K112 wild type containing pABc or p0c and either pTolCa or p0a in a 1-hexene saturated atmosphere were performed. Six different dilutions of cultures (10 cells to $10^7$ cells, left to right on the picture) were spotted in triplicate on an agar plate. Plates were then exposed to 1-hexene.
Figure 3:
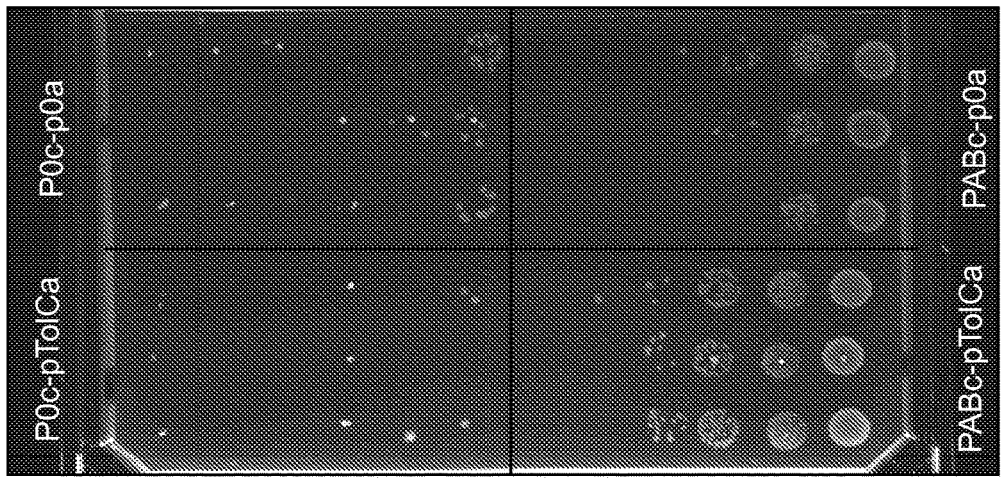

The results described above indicated that overexpression of the AcrAB-TolC pump provided an advantage in presence of 1-hexene. The plasmid pABc encoding AcrA and AcrB (or the control p0c) and the plasmid pTolCa encoding the outer membrane protein TolC (or its control p0a) were introduced into the E. coli K12 wild type strain and the survival of the strain tested in presence of 1-hexene. As this alpha-olefin is extremely volatile, a survival assay on agar plates in an atmosphere saturated in 1-hexene (see methods) was employed. It was observed that over-expressing acrA and acrB and TolC in the wild type strain led to an increased tolerance to 1-hexene (FIG. 3). Thus, expression of this pump over and above its native levels provided additional benefit towards this solvent-like compound. FIG. 3 shows that the over expression of only TolC in the wild type does not improve the survival. However, the overexpression of the genes acrA and acrB led to a strain with 1-hexene tolerance greater than the wild type, suggesting than TolC is not the limiting protein of the complex and is in excess in comparison to AcrA and AcrB. This imbalance can be explained by the fact that TolC is also involved in other membrane complexes (Ramos et al, 2002). The results also show that there was an upper limit to inducing the expression the pump, and induction of pump expression by adding more inducer (10, 20, 30, 40, and 50 mM of arabinose) caused a reduction in growth (data not shown). Thus, while an increase in the levels of AcrAB-TolC improved tolerance to 1-hexene, further increase in tolerance to the olefin compound is achieved using a more efficient pump.

Evaluating RND Efflux Pumps from Other Organisms.

Figure 7:
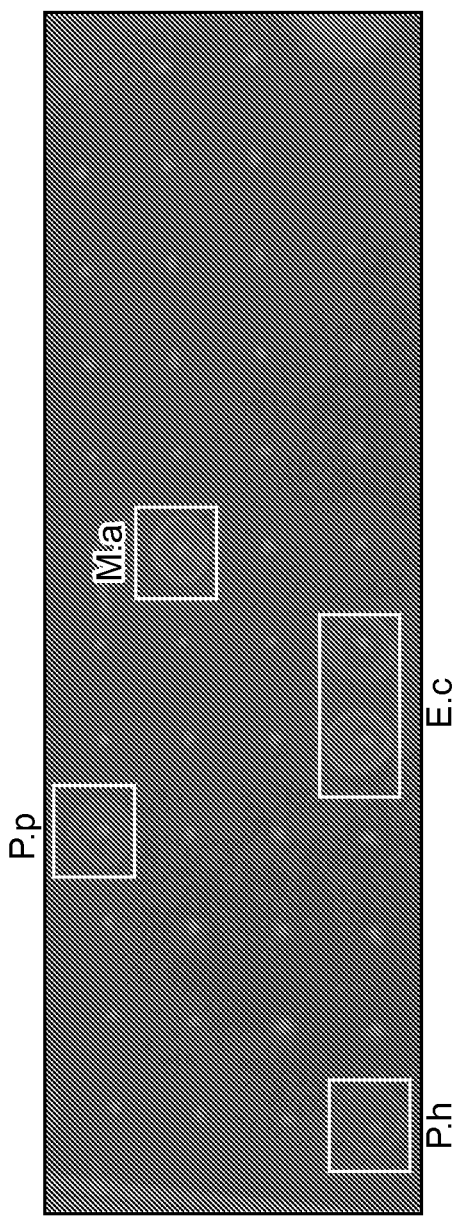
FIG. 7: Impact of homologous pumps on growth in presence of 1-hexene. Survival test of $E.$ $coli$ DH1 ΔacrAB producing either the AcrAB wild type or AcrAB homologs in a 1-hexene saturated atmosphere was performed. One dilution of cultures ($10^6$ cells) was spotted on agar plate. This experiment was repeated and showed similar results. From left to right and from top to bottom of the picture, are culture of strains producing the pumps $A.$ $vinelandii$ (YP_002797425), $A.$ $vinelandii$ (MexF), $A.$ $vinelandii$ (YP_002801502), $P.$ $putida$ (TtgB), $P.$ $putida$ (NP_745594), $P.$ $putida$ (MexF), $P.$ $putida$ (NP_743067), $P.$ $aeruginosa$ (MexB), $P.$ $aeruginosa$ (NP_250708), $P.$ $aeruginosa$ (MexF), $P.$ $aeruginosa$ (NP_253065), $P.$ $fluorescens$ (YP_258460), $P.$ $fluorescens$ (YP_260376), $P.$ $fluorescens$ (YP_258159), $P.$ $fluorescens$ (YP_258289), $R.$ $metallidurans$ (YP_586997), $R.$ $melallidurans$ (YP_583276), $R.$ $metallidurans$ (YP_583852), $M.$ $aqueolei$ (YP_960752), $M.$ $aqueolei$ (YP_957870), $P.$ $syringae$ (YP_276144), $P.$ $syringae$ (YP_275089), $P.$ $syringae$ (MdtB), $P.$ $syringae$ (YP_273025), $P.$ $syringae$ (YP_273463), $P.$ $syringae$ (YP_272632), $G.$ $metallireducens$ (YP_383777), $G.$ $metallireducens$ (YP_384620), $G.$ $metallireducens$ (YP_385464), $G.$ $metallireducens$ (YP_384608), $G.$ $metallireducens$ (YP_386066), $B.$ $pertussis$ (NP_880739), $D.$ $vulgaris$ (YP_009662), $S.$ $putrefaciens$ (YP_001181626), $A.$ $borkumensis$ (YP_692684), $B.$ $borkumensis$ (YP_694242), $P.$ $haloplanktis$ (AcrB), $S.$ $halifaxensis$ (YP_001672433), $S.$ $halifaxensis$ (YP_001673423), $S.$ $halifaxensis$ (YP_001674385), $E.$ $coli$ (AcrEF), $E.$ $coli$ (AcrAB), $E.$ $coli$ (AcrD).

An existing library of heterologous efflux pumps in E. coli (Dunlop et al. 2011) was used to test if another pump may provide better tolerance to 1-hexene than the native E. coli AcrAB-TolC system. Using the agar plate-based method, this strain library constructed in a DH1 ΔacrAB background was tested and the survival compared in presence of 1-hexene relative to the strain expressing an equivalent plasmid-borne copy of the native acrAB genes. The strains containing pumps from *Pseudomonas putida* KT2440, *Marinobacter aqueolei* EPL and *Pseudoalteromonas haloplanktis* TAC125 showed equivalent tolerance to 1-hexene relative to the native E. coli acrAB-expressing strain (FIG. 7).

Directed Evolution on AcrB to Improve Tolerance to 1-Hexene.

Figure 4:
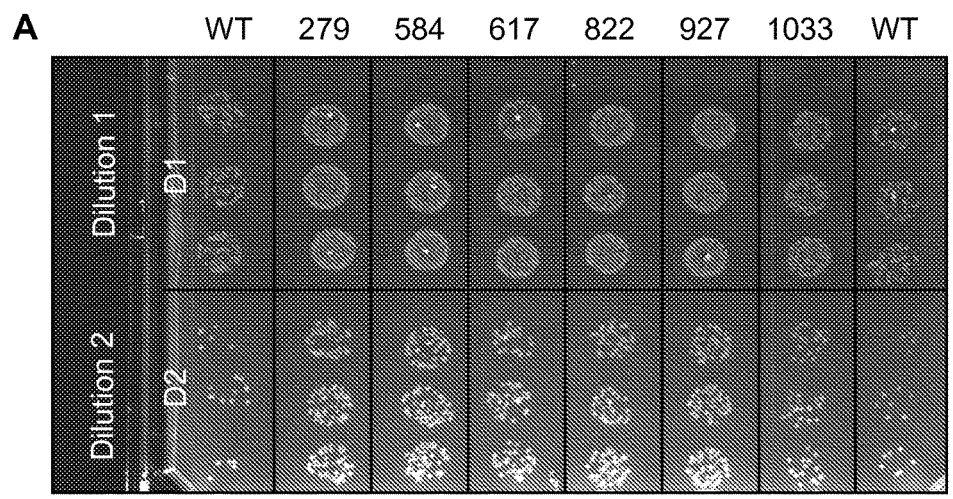
FIG. 4: Impact of beneficial mutations on AcrB on tolerance to 1-hexene, A: Survival test of $E.$ $coli$ strain producing either the AcrB wild type or variants in a 1-hexene saturated atmosphere was performed. Two dilutions of cultures (Dilution 1: $10^5$ cells and Dilution 2: $10^4$ cells) were spotted in triplicate on an agar plate. B: Localization of the 6 beneficial mutations represented on the structure of a single monomer of AcrB or C: on the structure of the AcrB trimer.
Figure 4:
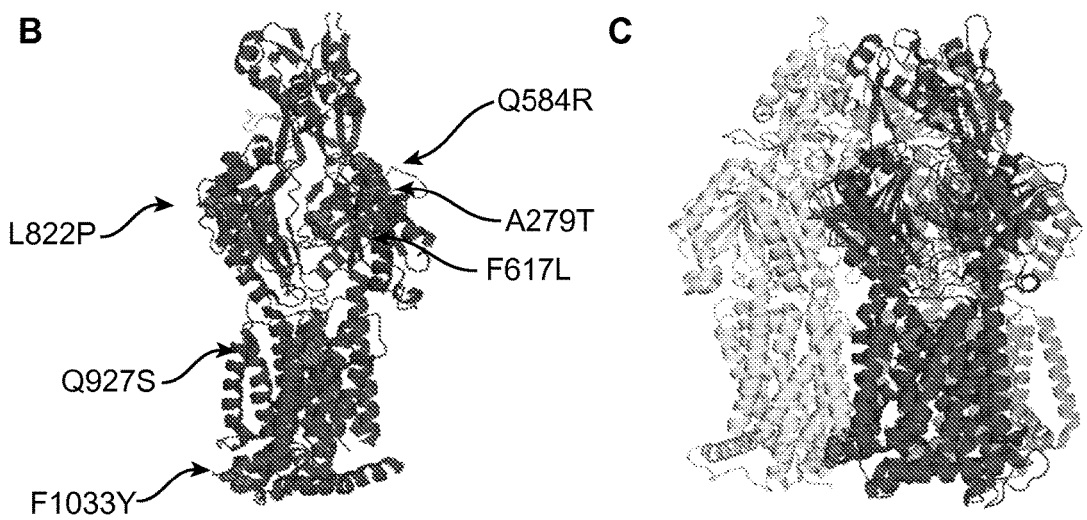

To identify AcrB variants that were more efficient at providing tolerance than the wild type AcrB, a high throughput screening using the 1-hexene saturated atmosphere assay (see, methods section) was developed. A library of AcrB variants was generated by introducing random mutations in the gene. AcrB variant genes were cloned in a low copy plasmid, in an operon with the acrA gene to maintain stoichiometry of the pump complex. The library of plasmids was introduced into E. coli K12 ΔacrAB. The library contained an average of 2.2 amino acid mutations per gene. Initially, 2500 clones expressing an AcrB variant were tested. It was observed that 1.1% of the clones had better survival in presence of 1-hexene relative to the strain encoding the wild type pump. A second library was then generated with a selection pressure directly after transformation, by incubating the freshly transformed cells in a 1-hexene atmosphere. In this condition, only 1 cell out of 8 survived and among the 500 cells tested in presence of 1-hexene, 9% were more tolerant than the strain expressing the wild type pump. The 20 most efficient variants were re-tested in duplicate, and 80% of them maintained better survival than the strain expressing the wild type AcrB, confirming the reliability of the screen. Plasmids were isolated from these strains and re-cloned them into fresh cells of the starting strain (K12 ΔacrAB). Of the freshly transformed cells, 63% maintained the increased tolerance relative to wild type, confirming that the 1-hexene tolerance phenotype tracked with the plasmids rather than in the genome of the mutant strain. Since most variants contained more than one mutation, the coding region of the acrB variant genes were sequenced to identify the mutations. Each individual mutation was generated to determine the ones that are responsible for the improved phenotype. Six amino acid mutations in AcrB were identified and confirmed that provided improvement in tolerance over the wild type sequence: A279T, Q584R, F617L, L822P, F927S and F1033Y (FIG. 4A). These mutations are localized all along the protein sequence (FIGS. 4B and C). Among the beneficial mutations, A279T, Q584R, F617L and L822P were more efficient.

Figure 6:
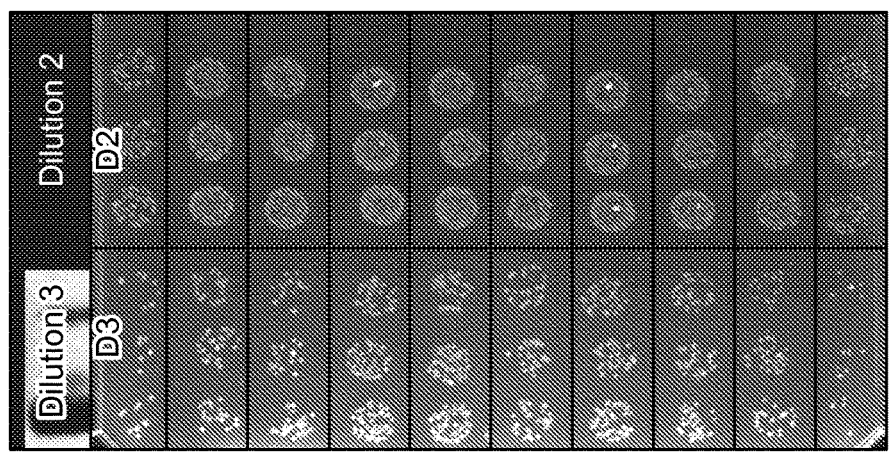
FIG. 6: Impact of beneficial mutations on AcrB on tolerance to 1-hexene. A: Survival test of $E.$ $coli$ strain producing either the AcrB Wild type or variants with 1, 2 or several beneficial mutations, in an 1-hexene saturated atmosphere was performed. Two dilutions of cultures (Dilution 2: $10^4$ cells and Dilution 3: $10^3$ cells) were spotted in triplicate on an agar plate. B: Soluble fraction of total proteins from a culture of strains producing either the wild type, either the variant F617L, either the variant 6 (A279T, Q584R, F617L) were analyzed by western blot using anti-His antibody.
Figure 6:
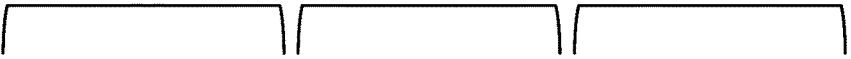

To determine if the mutations could act synergistically, selected mutations were combined in a single acrB gene generating 8 new variants with 2, 3 or 6 beneficial mutations (Var1: A279T and F617L, Var2: F617L and L822P, Var3: A279T and L822P, Var4: A279T and Q584R, Var5: A279T, F617L and L822P, Var6: A279T, Q584R and F617L, Var7: A279T, Q584R and F617L, Var8: A279T, Q584R, F617L, L822P, F927S and F1033Y). Most of the strains containing the AcrB with two beneficial mutations were found to be more tolerant to 1-hexene relative to an AcrB with one mutation (FIG. 6). However the combination of three or more mutations in the same protein did not result in additional advantage. It was also determined that the level of the AcrB variants in the soluble fraction of *E. coli* was less relative to the AcrB wild type (data not shown). Additionally, among the AcrB mutants, an increase in the number of beneficial mutations results in a decrease in the levels of the protein in the soluble fraction. These data suggest that the improvement in tolerance is likely due to an improvement in the efficiency or in the mode of action of the pump rather than due to improved protein production or stability.

Figure 5:
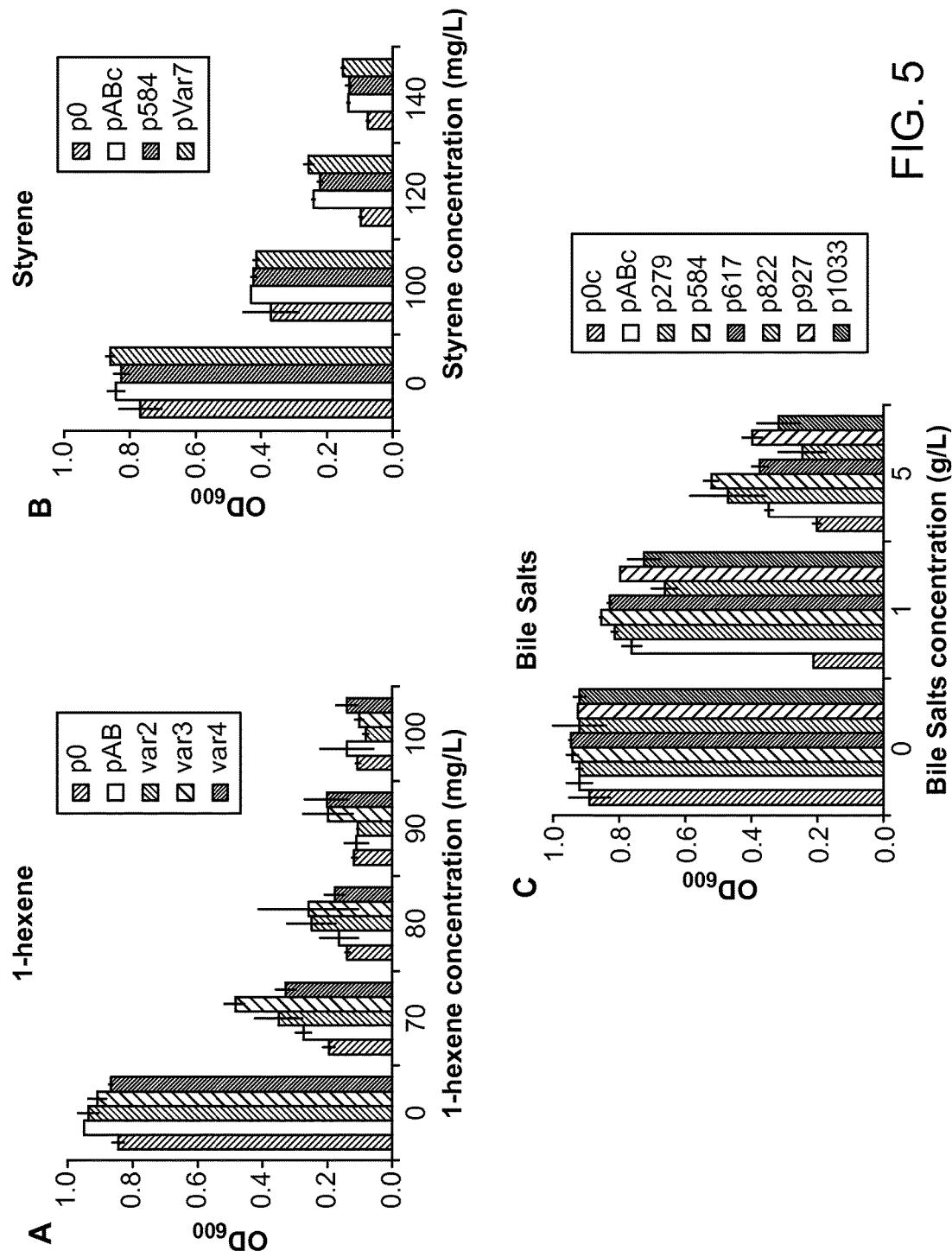
FIG. 5: Impact of beneficial AcrB mutations on growth, in presence of 1-hexene and styrene. Different concentrations of 1-hexene (A), styrene (B), or bile salts (C) were added to an $OD_{600}$=0.2 culture of $E.$ $Coli$ K12 ΔacrAB containing either the AcrB wild type (pABc) or the AcrB variants. OD densities were monitored after 2 hours of culture at 37° C. The bars represent standard deviation between duplicates.

The evolved AcrB strains were evaluated in liquid cultures containing 1-hexene, bile salts, or styrene. Growth of selected strains containing the AcrB variants in presence of different concentration of toxic olefins (FIG. 5) was analyzed. In presence of 1-hexene in the liquid cultures, it was observed that several strains producing evolved AcrB variants grew better than the wild type (FIG. 5A) confirming than these mutations were not specific to the agar plate assay. In presence of bile salts, the mutation Q584R improved the growth of the strain. None of the evolved AcrB variants that were tested provided benefit in presence of styrene relative to wild type AcrB (FIG. 5B). In contrast the evolved AcrB variants conferred tolerance to 1-hexene, relative to wild type AcrB (FIG. 5A). Thus, although AcrAB-TolC had been shown to be important to the growth of cells that produce styrene and the strains containing the AcrB variants were not tolerant to the olefin styrene, surprisingly, the strains exhibited tolerance to α-olefins, e.g., hexene.

Materials and Methods
Media, Chemicals, and Strains

Chemicals: styrene (99%), 1-hexene (99%), 1-octene (98%), nonene (96%), isopropyl b-D-1-thiogalactopyranoside (IPTG), dodecane, arabinose, bile salts, chloramphenicol (Cm), kanamycin (Km), ampicillin (Amp) are from Sigma-Aldrich (St. Louis, Mo.); dimethylformamide (DMF) is from Fisher Scientific (Hampton, N.H.); and glucose is from VWR (Westchester, Pa.).

All strains, plasmids and oligonucleotides are listed in Table 1. Oligonucleotides synthesis and sequencing were conducted at Integrated DNA Technologies (Coralville, Iowa) and Quintara (Albany, Calif.) respectively. Strains were cultured in Luria-Bertani (LB) broth supplemented with appropriate antibiotics, or inducers as necessary, and with 15 g/L agar (BD, Sparks, Md.) for plate culture and assays.

*E. coli* DH10B (Table 1) was used for sub-cloning, *E. coli* K12 BW25113 (Baba et al., 2001) was used for toxicity assay and *E. coli* NST74 was used for styrene production. *Arabidopsis thaliana* (ecotype Col-0) cDNA and *Saccharomyces cerevisiae* S288C were used to amplify genes required for styrene production: PAL2 and FDC1 (McKenna et al. 2011). The efflux pump library containing 43 different pumps from heterologous sources was in an *E. coli* DH1 ΔacrAB background (Dunlop et al, 2011).

Construction of Gene Deletion Mutants

The *E. coli* K12 BW25113 ΔacrAB and *E. coli* NST74 ΔacrAB strains were constructed using the one-step inactivation of chromosomal genes using published methods (Datsenko et al, 2000). In order to generate a ΔacrAB strain, the *E. coli* K12 BW25113 ΔacrA was used. The chromosomally-encoded kanamycin (Km) marker in the ΔacrA strain was removed using the pCP20, and the plasmid pKD46 was introduced into the resulting strain. The PCR product used to mediate gene replacement for acrB was amplified from the *E. coli* K12 BW25113 ΔacrB strain using the primers DelB F and DelB R and introduced in the Km-free *E. coli* K12 BW25113 ΔacrA strain (pKD46). $Km^R$ colonies were tested for the loss of acrB. After curing the pKD46, the $Km^R$ gene was removed generating the strain *E. coli* K12 ΔacrAB. For the *E. coli* NST74 ΔacrAB, the PCR used to mediate the replacement of acrA and acrB in the *E. coli* NST74 was amplified from *E. coli* K12 BW25113 ΔacrAB $Km^R$ using the primers DelAB F and DelAB R, and introduced in the *E. coli* NST74 carrying pKD46. $Km^R$ colonies were tested for the loss of operon encoding acrA and acrB. Here again, after curing the pKD46, the $Km^R$ gene was removed generating the final strain *E. coli* NST74 ΔacrAB.

Construction of Plasmids

High fidelity phusion polymerase (Thermo Scientific, Waltham, Mass.) was used for all gene amplifications, except for generating the acrB variant library. All restriction enzymes were fast-digest enzymes from Thermo Scientific (Waltham, Mass.), tolC was amplified using the primers TolC F and TolC R and cloned in the pBbS5a-RFP (p0a) with the restriction sites NdeI and XhoI generating the plasmid pTolCa. acrA was amplified using the primers AcrA F and AcrA R and cloned into the pBbA8c-RFP (p0c) using the restriction sites BglII and NdeI generating the plasmid pAc. acrB was amplified using the primers AcrB F and AcrB R and cloned in pAc using the restriction site NdeI and XhoI generating the plasmid pABc.

Genes encoding PAL2 and FDC1, required for styrene production, were amplified from *Arabidopsis thaliana* and *Saccharomyces cerevisiae* S288C cDNA respectively.

To generate the acrB variant library by error prone PCR, Dream Taq polymerase (Thermo Scientific, Waltham, Mass.) was used. PCR products were obtain by amplifying acrB from pABc (0.5 ng/μL), using the primers Cam F and Cam R (0.1 μM), the kit buffer (containing $MgCl_2$ at 2 mM final concentration), dNTP mix at 0.2 mM (Thermo Scientific, Waltham, Mass.), 1% DMSO and 0.1 unit/μL. No extra $Mn^{2+}$ was used to induce mutation. Twenty cycles were performed resulting in a pool of mutated acrB sequences containing 2.2 amino acid mutations, on an average. PCR fragments were gel-extracted, cloned using the Gibson cloning method (Gibson et al, 2009) into pAc digested with NdeI and XhoI, and then introduced into the E. coli K12 ΔacrAB strain.

The acrB variants with desired mutations were generated by overlap PCR using the high fidelity phusion polymerase (Thermo Scientific, Waltham, Mass.). For each single mutation variant, two PCR products were obtained by amplification from the pABc vector as listed in Table 1: PCR 1 and 2 were extracted for every variant and used to generate long fragments containing the full length genes. The resulting products were introduced with the Gibson assembly method (Gibson et al, 2009) into pAc digested by NdeI and XhoI, and transformed in E. coli DH10B. Plasmids with confirmed sequences were then introduced into the E. coli K12 ΔacrAB strain. The variants with multiple mutations were obtained by introducing additional mutation(s) in a given variant, using the same method described previously (overlapping PCR products). PyMOL (www website pymol.org/) was used to visualize the structure of AcrB and the localization of the individual mutations.

Growth Impact of AcrA-acrB Overexpression.

Colonies of E. coli K12 ΔacrAB containing the plasmid pABc were used to inoculate a 6 mL LB-Cm pre-culture tube. 100 μL of cells at $OD_{600}=1$ were used to inoculate 10 mL LB-Cm supplemented with glucose (2 g/L) and various concentration of arabinose (0, 5, 10, 20, 30, 40 and 50 mM). Cell growth at 37° C. was followed by $OD_{600}$ measurements using a spectrophotometer (Beckman Coulter DU800, Brea, Calif.).

Impact of Alpha-Olefins and Styrene on Growth.

Cells were first inoculated in 6 mL LB-Cm with glucose (2 g/L) and arabinose (5 mM). At $OD_{600}=1$ at 37° C., 100 μL of culture were transferred to 15 mL glass culture tubes (VWR, Westchester, Pa.) with a septum lid (VWR, Westchester, Pa.) containing 10 mL of LB, supplemented with the appropriate antibiotic and inducer. Septum lids were required to limit evaporation of chemicals. DMF was used as cosolvent for all three compounds to prepare stock solutions at different concentrations (styrene at 10, 12, 14 and 16 g/L, 1-hexene at 5, 6, 7 and 8 g/L and 1-octene at 10, 20, 50 and 100 g/L). At an $OD_{600}$ of 0.2, 100 μL of the olefin stock solutions was added. After 2 hours at 37° C., $OD_{600}$ was measured. All measurements are in duplicate.

For agar plate based assays, cells were first streaked overnight and few colonies were used to inoculate a preculture of 6 mL of LB-Cm with glucose (2 g/L) and arabinose (5 mM). At $OD_{60}=1$ at 37° C., the cultures were used to prepare a dilution series. Dilution 0 (D0) corresponds to the $OD_{600}$, =1, and contains ~$10^9$ cells/mL. Dilution 1 (D1) is a 10-fold dilution of D0, dilution 2 (D2) a 10-fold dilution of D1 up to dilution 5 (D5), which contains ~$10^4$ cells/mL. 10 μL of each dilution was spotted in triplicate on LB-agar plates (single well plates, Thermo Scientific, Waltham, Mass.) containing 30 mL of LB-agar, Cm (30 mg/L), glucose (2 g/L) and arabinose (5 mM). Small containers (microfuge tube lids) were placed on the open lid of the agar plate and filled with 400 to 600 μL of 1-hexene or 1-octene or with 75 μL of 1-nonene. The agar plates were then inverted over the lid, cells facing the olefin compound, sealed with parafilm, placed in the plastic bag (the original packaging for the petri dishes) and incubated for 2 days at room temperature. For 1-octene, a second condition, via overlaying 2 mL of compound on the top of the agar submerging the cells, was used. TolC overexpression impact was examined using the same method, but in this case, the LB media and the LB-agar were also supplemented with ampicillin (100 mg/L) and IPTG (100 μM).

For the high throughput screening of AcrB variants, two methods were used. After transformation of the library in E. coli K12 ΔacrAB, cells were plated on LB-agar-Cm plate either without a 1-hexene selection pressure or with 1-hexene exposure using 300 μL to saturate the atmosphere. Clones were collected and inoculated in 96 deep well plates (USA Scientific, Ocala, Fla.) using 800 μL LB (supplemented with chloramphenicol 30 mg/L, glucose 2 g/L, arabinose 5 mM) and cultured overnight at 37° C. with agitation. Cells were then diluted 100 fold and 5 μL of the dilution was spotted on agar plates (Thermo Scientific, Waltham, Mass.) containing 25 mL of LB-agar-Cm and inducer, using a liquid handler robot (Biomek FX, Beckman Coulter, Brea, Calif.). 600 μL of 1-hexene was used per plate to create a saturated atmosphere. Plates were sealed and incubated for 2 days as described in the previous paragraph.

To test the heterologous efflux pump library, the same method was used. Clones were grown in 96 DWP overnight at 37° C. in presence of IPTG 10 μM, and 5 μL of a 100× dilution of the overnight culture was spotted on agar plate using the liquid handler robot. 600 μL of 1-hexene was used to generate a toxic atmosphere.

Measuring the Toxic Effect of Styrene

E. coli NST74 ΔacrAB containing pABc or p0c and either $p_{lac}$Sty, $p_{trc}$Sty, $p_{lac}$0 or $p_{trc}$0, were inoculated into 6 mL LB (supplemented with 15 μL glucose, and 10 mM arabinose and appropriate antibiotics). At $OD_{600}=1$, 5 μL cells were inoculated in 95 μL of LB-antibiotic, 15 g/L glucose, 10 mM arabinose, biolog redox dye (Mix A) solution (Biolog, Hayward, Calif.) and various concentration of IPTG (0, 10, 20, 50 100, 200 and 300 μM). The experiment was performed in 96 well plates (Biolog, Hayward. Calif.), at 37° C. and growth was monitored using the Omnilog system (Biolog. Hayward, Calif.). In this condition all the strains containing p0c (no AcrAB production) did not grow. For the strains possessing the $p_{trc}$Sty, the impact of styrene production on growth was also tested on LB-agar plate containing 25 mg/L Km, 15 g/L glucose, 10 mM arabinose and 100 μM IPTG). For glass tubes based growth of E. coli NST74 ΔacrAB (with pABc or p0c and either $p_{lac}$Sty or $p_{lac}$0), colonies were inoculated in 10 mL of LB (supplemented with 100 mg/L ampicillin, 15 g/L glucose, 10 mM arabinose) and grown overnight at 37° C. From this culture, cells were inoculated in glass tubes (starting $OD_{600}$ of 0.02) containing 10 mL of LB (supplemented with 100 mg/L ampicillin, 15 g/L glucose, 10 mM arabinose and 100 μM IPTG. Growth was monitored using a spectrophotometer (Beckman Coulter DU800. Brea, Calif.).

Western Blotting

Cultures were incubated at 37° C. in LB-Cm, 2 g/L glucose and 5 mM arabinose. At $OD_{600}=1$, the pellet of 2 mL of culture was resupended and incubated for 15 min in 30 μL of B-Per buffer (Thermo Scientific, Waltham, Mass.) supplemented with 1 mg/ml lysozyme (Sigma-Aldrich, St. Louis, Mo.). Each sample was sonicated (SP Scientific, Gardiner, N.Y.) for 5 seconds at the lowest power setting at 4° C., then centrifuged at 4° C. for 30 min at 15 rpm. Total protein quantity present in the soluble fraction was determined using the DC Lowry Reagent according the protocol of the supplier (Bio-Rad, Hercules, Calif.). All samples were normalized to the same quantity of total soluble protein. 20 μL of normalized samples was mixed with SDS loading dye buffer (Life technologies, Carlsbad, Calif.) and DTT (Life technologies, Carlsbad, Calif.) and incubated at 98° C. for 20 min. 10 μL of samples were run on 4-12% Bis-Tris gel (Life technologies. Carlsbad, Calif.) at 165 V under SDS MES Buffer (Life technologies, Carlsbad, Calif.). Proteins were transferred to a PVDF membrane (Life technologies, Carlsbad, Calif.) using iBlot transfer system (Life technologies, Carlsbad, Calif.). The membrane was washed in PBS buffer (20 mM NaPhosphate pH=7.4, 50 mM NaCl) and blocked overnight at 4° C. with 25 mL of PBS-Tween-20 (EMD Millipore, Billerica, Mass.) supplemented with 3% of BSA (Sigma-Aldrich, St. Louis, Mo.). The primary antibody is a monoclonal mouse anti-His (Sigma-Aldrich, St. Louis, Mo.) diluted 1:5000, the secondary antibody is a goat anti-mouse HRP conjugated (Sigma-Aldrich, St. Louis, Mo.) diluted 1:10,000. Both antibodies were suspended in 1% BSA and PBS-Tween-20, and consecutively added to the membrane for 1 hour at room temperature. Three washes in PBS-Tween20 were performed after incubation of each antibody. Membrane was then incubated in 2 mL of HRP detection solution (Bio-Rad, Hercules, Calif.) for 10 min.

Summary of Illustrative Examples

In these examples, it was demonstrated that the tripartite RND efflux pump in *E. coli* composed of AcrA, AcrB and TolC subunits played a major role in the tolerance of *E. coli* cells to alpha-olefins, and is important in reaching high production levels of these toxic compounds. *E. coli* has been engineered to manufacture many bulk chemicals (Nakamura and Whited 2003; Yim et al. 2011). In these, examples, the benefit of increasing the levels of the AcrAB-TolC efflux pump was first evaluated. Increasing the expression of AcrAB-TolC had a positive impact on tolerance to 1-hexene, although in these experiments, this was limited by the toxicity linked to overexpression of membrane proteins (Wagner et al. 2007). Directed evolution of AcrB was then used to improve tolerance. Two recent studies have used directed evolution to improve AcrB tolerance to n-butanol (Fisher et al. 2013) and ca-pinene and n-octane (Foo and Leong 2013).

These examples further illustrated that engineering the AcrB subunit of this efflux pump improved tolerance to 1-hexene. AcrB variants having improved tolerance to 1-hexene were identified and the primary domains responsible for 1-hexene tolerance were characterized. It has been shown that the entrance of substrates into the efflux pump and the amino acids involved in the substrate binding depends on the properties and the size of the compounds (Eicher et al. 2012; Takatsuka et al. 2010). To better understand the domain involved in 1-hexene tolerance, several beneficial mutations obtained in the first round of evolution. Several mutations (A279T, Q584R, F617L, L822P, F927S and F1033Y) were identified that resulted in improved tolerance to 1-hexene. These mutations had an additive effect, but in some experiments, it was also observed that multiple changes may be disruptive for protein solubility. Most of the AcrB variants in these experiments resulted in decreased protein in the soluble fraction, which indicates the improvement in the tolerance conferred by these variants is due to higher pump efficiency.

Crystallographic and site-directed mutagenesis studies for AcrB have determined the role of domains and of several amino acids in the protein (Husain and Nikaido 2010; Murakami et al. 2002). Not to be bound by theory, the crystal structure and the data available provide a basis to analyze the effect of beneficial mutations. Of the many amino acid changes identified, F927S and more particularly F1033Y were in the most unexpected positions. F927S is localized in the transmembrane domain, at the top of the TM10 α-helix. This helix contains an important amino acid (K940) involved in the proton transport (Su et al. 2006) and a mutation in this helix could impact the rotational movements leading to compound export. However the mutations A279T, Q584R, F617L and L822P were found in positions known to be important for pump function. The amino acid L822 is positioned between the 2 β-sheets C13 belonging to the pore domain PN1 and Cβ14 from the PC2. The mutation of a leucine to a proline is localized between these 2 β-sheets at the "ceiling" of the vestibule, suggested to be a highly probable substrate entrance point, and could change the flexibility and/or the opening of the vestibule facilitating 1-hexene entrance into the pore. The amino acid A279 is localized at the binding pocket in which residues Glu273. Asn274, Asp276, Ile277, play an important roles (Husain et al. 2011). Q584 is localized in a position such that it may be involved in the trimer assembly. AcrB subunit is reported to fold independently, and then assemble into a trimer (Yu et al. 2011). This mutation is also clearly beneficial to the growth of *E. coli* in presence of bile salts confirming that its role is not specific to 1-hexene, although in these experiments, we could not detect any positive impact in presence of styrene. Finally, the amino acid F617 has been shown to be located in the switch loop of the hydrophobic binding pocket and reported crystal structures suggest that this amino acid could directly interact with various substrates (Bohnert et al. 2008; Eicher et al. 2012; Vargiu et al. 2011). Mutating this amino acid F617 to an alanine has been reported to have a direct impact on substrate uptake and was responsible for a substantial decrease in transport of novobiocin, but a minor effect on the transport of oxacillin and various other macrolides (Bohnert et al. 2008). In this study, a mutation to a leucine at this position had a positive impact on the transport of 1-hexene.

The experiments performed for this study, as well as other reports in the literature (Bohnert et al. 2008) suggest that the AcrB protein is destabilized when more than three mutations are introduced in the sequence. However, additional rounds of mutations, starting with variants with one or two mutations, could stabilize the protein and allow the introduction of more mutations to further improve function. Additionally, analyses of more variants showing a positive impact for 1-hexene tolerance could give a better understanding of the path(s) of this compound through the pump. Directed evolution of AcrB has also been used to improve tolerance and secretion of other compounds. It has also been shown that AcrB can be improved for n-butanol. α-pinene and n-octane (Fisher et al. 2013; Foo and Leong 2013). These studies resulted in beneficial mutations in different positions relative to the ones identified in our study. Specifically, N189H, T678S, Q737L and M844L improved the efflux of α-pinene, n-octane, while I466F, M355L, and S880P improved the growth on n-butanol. These authors proposed corresponding improvements in the AcrB-TolC interaction and enlargement in the entrance of the cleft that facilitate conformational changes or improve the affinity for the substrate. The results provided in the illustrative experiments presented in these examples thus also suggest that several domains can be targeted for mutations to lead to a more efficient pump.

TABLE 1

| strains | Description |
|---|---|
| *E. coli* DH10B | araΔ139 Δ(ara,leu)7697 fhuA lacX74 galK16 galE15 mcrA f80d(lacZΔM15) recA1 relA1 endA1 nupG rpsl. rph spoT1Δ(mrr-hsdRMS-mcrBC) |
| *E. coli* K12 B PW25113 | laclq rrnBT14 ΔlacZWJ16 hsdR514 ΔaraBA-DAH33 ΔrhaBADLD78 |
| *E. coli* NST74 | aroH367, tyrR366, tna-2, lacY5, aroF394(fbr), malT384, pheA101(fbr), pheO352, aroG397(fbr) |
| *E. coli* K12 BW25113 ΔacrA | laclq rrnBT14 ΔlacZWJ16 hsdR514 ΔaraBA-DAH33 ΔrhaBADLD78 ΔacrA KmR |
| *E. coli* K12 BW25113 ΔacrB | laclq rrnBT14 ΔlacZWJ16 hsdR514 ΔaraBA-DAH33 ΔrhaBADLD78 ΔacrB KmR |
| *E. coli* K12 BW25113 ΔacrAB | laclq rrnBT14 ΔlacZWJ16 hsdR514 ΔaraBA-DAH33 ΔrhaBADLD78 ΔacrAB KmR |
| *E. coli* NST74 ΔacrAB | aroH367, tyrR366, tna-2, lacY5, aroF394(fbr), malT384, pheA101(fbr), pheO352, aroG397(fbr) |
| *Saccharomyces cerevisiae* S288C | source of fdc1 |

| strain library of heterologous pumps | Description |
|---|---|
| *E. coli* DH1 ΔacrAB | endA1 recA1 gyrA96 thi-1 glnV44 relA1 hsdR17(rK- mK+) λ- ΔacrA KmR |

| cDNA | Description |
|---|---|
| *Arabidopsis thaliana* (ecotype Col-0) | source of pal2 |

| plasmids | Description |
|---|---|
| pCP20 | oriR101 w/ repA101ts, AmpR CmR, flp recombinase |
| pKD46 | oriR101 w/ repA101ts, AmpR, araC, pBAD λ red recombinase |
| pBbS5a-RFP (p0a) | Plac, SC101 ori, lacI, AmpR, RFP |
| pTolCa | Plac, SC101 ori, lacI, AmpR, TolC |
| pBbA8c-RFP (p0c) | PBAD, p15 ori, araC, CmR, RFP |
| pAc | PBAD, p15 ori, araC, CmR, RFP, AcrA |
| pABc | PBAD, p15 ori, araC, CmR, RFP, AcrA, AcrB |
| pBbE5a-RFP (plac0) | Plac, ColE1 ori, lacI, AmpR, RFP |
| placSty | Plac, ColE1 ori, lacI, AmpR, PAL2, FDC1 |
| pBbE1k-RFP (ptrc0) | Ptrc, ColE1 ori, laclq, KmR, RFP |
| ptrcSty | Ptrc, ColE1 ori, laclq, KmR, PAL2, FDC1 |

| primers (5'-3') | sequence (SEQ ID NOS: 6-33) |
|---|---|
| DelB F | CTGAACAGTCCAAGTCTTAACTTAAACAGGAGC |
| DelB R | CATACTAGCACTAACCCGCAGCAGG |
| DelAB F | CGTGCCATATGTTCGTGAATTTACAGGCG |
| DelAB R | CATACTAGCACTAACCCGCAGCAGG |
| TolC F | AAAGATCTTTTAAGAAGGAGATATACATATGAAGAAATTGCTCCCCATTCTTATCGGCC |
| TolC R | ACTCGAGGGATCCTCAGTGGTGGTGGTGGTGGTGGTTACGGAAAGGGTTATGACCGTTAC |
| AcrA F | TAAAGATCTTTTAAGAAGGAGATATACAGATGAACAAAAACAGAGGGTTTACGCC |
| AcrA R | AAAACATATGTTAACGGCTCCTGTTTAAGTTAAGACTTGGACTGTTCAGGCTGAGC |
| AcrB F | CCAAGTCTTAACTTAAACAGGAGCCGTTAACATATG |

TABLE 1-continued

| | |
|---|---|
| AcrB R | GATCCTTACTCGAGGGATCCTCAGTGG |
| Fdc1 F | AAAGATCTTTTAAGAAGGAGATATACATATGAGGAAGCTAAATCCAGCTTTAGAATTTAG |
| Fdc1 R | TCCTTCTTAAACCCGGGTCCTTATTTATATCCGTACCTTTTCCAATTTTCATTTACTTTG |
| Pal2 F | ATAAGGACCCGGGTTTAAGAAGGAGATATACAAATGGATCAAATCGAAGCAATGTTGTG |
| Pal2 R | CTTACTCGAGTTAGCAAATCGGAATCGGAGCTCCGTTC |
| Cam F | CGGTGCTCAGCCTGAACAGTCCAAGTC |
| Cam R | TCTTTCGACTGAGCCTTTCGTTTTATTTGATGCC |
| A279T R | GCCGTTAAACTCTGTGATGATGTCGTAG |
| A279T F | CTACGACATCATCACAGAGTTTAACGGC |
| Q584R R | GTGTACGTTCCCGCGTTGCACC |
| Q584R F | GGTGCAACGCGGGAACGTACAC |
| F617L R | CTGACCACGTCCCGCAAGGCCGAAGCCGTTAACG |
| F617L F | CGTTAACGGCTTCGGCcTTGCGGGACGTGGTCAG |
| L822P R | CATGGATGGCGGGCCGTTGTAAC |
| L822P F | GTTACAACGGCCCGCCATCCATG |
| F927S R | GGCCTACCTGGGAGTAAACGTC |
| F927S F | GACGTTTACTCCCAGGTAGGCC |
| F1033Y R | CATTCTTGCGGCTATAGCGGCGGC |
| F1033Y F | GCCGCCGCTATAGCCGCAAGAATG |

| AcrB variants | AcrB variants have been made by overlaping 2 PCRs fragments bellow |
|---|---|
| variant A279T | PCR1 (primers: Cam F + A279T R) + PCR2 (primers: A279T F + Cam R) |
| variant Q584R | PCR1 (primers: Cam F + Q584R R) + PCR2 (primers: Q584R F + Cam R) |
| variant F617L | PCR1 (primers: Cam F + F617L R) + PCR2 (primers: F617L F + Cam R) |
| variant L822P | PCR1 (primers: Cam F + L822P R) + PCR2 (primers: L822P F + Cam R) |
| variant F927S | PCR1 (primers: Cam F + F927S R) + PCR2 (primers: F927S F + Cam R) |
| variant F1033Y | PCR1 (primers: Cam F + F1033Y R) + PCR2 (primers: F1033Y F + Cam R) |

REFERENCE LISTING FOR REFERENCES CITED BY AUTHOR AND PUBLICATION YEAR

Bohnert J A, Schuster S, Seeger M A, Fahnrich E, Pos K M, Kern W V. 2008. Site-directed mutagenesis reveals putative substrate binding residues in the *Escherichia coli* RND efflux pump AcrB. Journal of bacteriology 190(24): 8225-9.

Doshi R, Nguyen T, Chang G. 2013. Transporter-mediated biofuel secretion. Proceedings of the National Academy of Sciences of the United States of America 110(19): 7642-7.

Dunlop M J, Dossani Z Y, Szmidt H L, Chu H C, Lee T S, Keasling J D, Hadi M Z, Mukhopadhyay A. 2011. Engineering microbial biofuel tolerance and export using efflux pumps. Molecular Systems Biology 7:487.

Dunlop M J, Jay D. Keasling1 a, Mukhopadhyay1 A. 2010. A model for improving microbial biofuel production using a synthetic feedback loop Systems and Synthetic Biology.

Eicher T, Cha H J, Seeger M A, Brandstatter L, El-Delik J, Bohnert J A, Kern W V, Verrey F, Grutter M G, Diederichs K and others. 2012. Transport of drugs by the multidrug transporter AcrB involves an access and a deep binding pocket that are separated by a switch-loop. Proceedings of the National Academy of Sciences of the United States of America 109(15):5687-92.

Fisher M A, Boyarskiy S, Yamada M R, Kong N, Bauer S, Tullman-Ercek D. 2013. Enhancing Tolerance to Short-Chain Alcohols by Engineering the *Escherichia coli* AcrB Efflux Pump to Secrete the Non-native Substrate n-Butanol. ACS synthetic biology.

Foo J L, Leong S S. 2013. Directed evolution of an *E. coli* inner membrane transporter for improved efflux of biofuel molecules. Biotechnology for biofuels 6(1):81.

Husain F, Bikhchandani M, Nikaido H. 2011. Vestibules are part of the substrate path in the multidrug efflux transporter AcrB of *Escherichia coli*. Journal of bacteriology 193(20):5847-9.

Husain F, Nikaido H. 2010. Substrate path in the AcrB multidrug efflux pump of *Escherichia coli*. Molecular microbiology 78(2):320-30.

Jarboe L R, Zhang X, Wang X, Moore J C, Shanmugam K T, Ingram L O. 2010. Metabolic engineering for production of biorenewable fuels and chemicals: contributions of synthetic biology. Journal of biomedicine & biotechnology 2010:761042.

McKenna R, Nielsen D R. 2011. Styrene biosynthesis from glucose by engineered *E. coli*. Metabolic engineering 13(5):544-54.

Murakami S, Nakashima R, Yamashita E, Yamaguchi A. 2002. Crystal structure of bacterial multidrug efflux transporter AcrB. Nature 419(6907):587-93.

Murakami S, Tamura N, Saito A, Hirata T, Yamaguchi A. 2004. Extramembrane central pore of multidrug exporter AcrB in *Escherichia coli* plays an important role in drug transport. The Journal of biological chemistry 279(5): 3743-8.

Murakami S, Yamaguchi A. 2003. Multidrug-exporting secondary transporters. Current opinion in structural biology 13(4):443-52.

Nakamura C E, Whited G M. 2003. Metabolic engineering for the microbial production of 1,3-propanediol. Current opinion in biotechnology 14(5):454-9.

Nikaido H. 2009. Multidrug resistance in bacteria. Annual review of biochemistry 78:119-46.

Nikaido H, Takatsuka Y. 2009. Mechanisms of RND multidrug efflux pumps. Biochimica et biophysica acta 1794 (5):769-81.

Ramos J L, Duque E, Gallegos M T, Godoy P, Ramos-Gonzalez M I, Rojas A, Teran W, Segura A. 2002. Mechanisms of solvent tolerance in gram-negative bacteria. Annual review of microbiology 56:743-68.

Schubert P, Steinbuchel A, Schlegel H G. 1988. Cloning of the *Alcaligenes eutrophus* genes for synthesis of poly-beta-hydroxybutyric acid (PHB) and synthesis of PHB in *Escherichia coli*. Journal of bacteriology 170(12):5837-47.

Seeger M A, Schiefner A, Eicher T, Verrey F, Diederichs K, Pos K M. 2006. Structural asymmetry of AcrB trimer suggests a peristaltic pump mechanism. Science 313 (5791):1295-8.

Seeger M A, von Ballmoos C, Eicher T, Brandstatter L, Verrey F, Diederichs K, Pos K M. 2008. Engineered disulfide bonds support the functional rotation mechanism of multidrug efflux pump AcrB. Nature structural & molecular biology 15(2):199-205.

Sennhauser G, Amstutz P, Briand C, Storchenegger O, Grutter M G. 2007. Drug export pathway of multidrug exporter AcrB revealed by DARPin inhibitors. PLoS biology 5(1):e7.

Sikkema J, de Bont J A, Poolman B. 1995. Mechanisms of membrane toxicity of hydrocarbons. Microbiological reviews 59(2):201-22.

Su C C, Li M, Gu R, Takatsuka Y, McDermott G, Nikaido H, Yu E W. 2006. Conformation of the AcrB multidrug efflux pump in mutants of the putative proton relay pathway. Journal of bacteriology 188(20):7290-6.

Takatsuka Y, Chen C, Nikaido H. 2010. Mechanism of recognition of compounds of diverse structures by the multidrug efflux pump AcrB of *Escherichia coli*. Proceedings of the National Academy of Sciences of the United States of America 107(15):6559-65.

Takatsuka Y, Nikaido H. 2007. Site-directed disulfide cross-linking shows that cleft flexibility in the periplasmic domain is needed for the multidrug efflux pump AcrB of *Escherichia coli*. Journal of bacteriology 189(23):8677-84.

Takatsuka Y, Nikaido H. 2009. Covalently linked trimer of the AcrB multidrug efflux pump provides support for the functional rotating mechanism. Journal of bacteriology 191(6):1729-37.

Takatsuka Y, Nikaido H. 2010. Site-directed disulfide cross-linking to probe conformational changes of a transporter during its functional cycle: *Escherichia coli* AcrB multidrug exporter as an example. Methods in molecular biology 634:343-54.

Tikhonova E B, Yamada Y, Zgurskaya H I. 2011. Sequential mechanism of assembly of multidrug efflux pump AcrAB-TolC. Chemistry & biology 18(4):454-63.

Tseng T T, Gratwick K S, Kollman J, Park D, Nies D H, Goffeau A, Saier M H, Jr. 1999. The RND permease superfamily: an ancient, ubiquitous and diverse family that includes human disease and development proteins. Journal of molecular microbiology and biotechnology 1(1):107-25.

Vargiu A V, Collu F, Schulz R, Pos K M, Zacharias M, Kleinekathofer U, Ruggerone P. 2011. Effect of the F610A mutation on substrate extrusion in the AcrB transporter: explanation and rationale by molecular dynamics simulations. Journal of the American Chemical Society 133(28):10704-7.

Vargiu A V, Nikaido H. 2012. Multidrug binding properties of the AcrB efflux pump characterized by molecular dynamics simulations. Proceedings of the National Academy of Sciences of the United States of America 109(50): 20637-42.

Wagner S, Baars L, Ytterberg A J, Klussmeier A, Wagner C S, Nord O, Nygren P A, van Wijk K J, de Gier J W. 2007. Consequences of membrane protein overexpression in *Escherichia coli*. Molecular & cellular proteomics: MCP 6(9):1527-50.

Yim H, Haselbeck R, Niu W, Pujol-Baxley C, Burgard A, Boldt I, Khandurina J, Trawick J D, Osterhout R E, Stephen R and others. 2011. Metabolic engineering of *Escherichia coli* for direct production of 1,4-butanediol. Nature chemical biology 7(7):445-52.

Yu L, Lu W, Wei Y. 2011. AcrB trimer stability and efflux activity, insight from mutagenesis studies. PloS one 6(12): e28390.

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession number, and patent applications cited herein are hereby incorporated by reference in their entirety for all purposes. Illustrative Native AcrB-Like Sequences:

```
Pseudomonas putida KT2440 (NCBI NP_743544), SEQ ID NO: 2;
synonyms: ttgB, PP_1385
     1  mskifidrpi fawvialvim ivgalsilkl pingypsiap paiaiavtyp gasagtvgdt 61  vvqvieqqln gidnlryvss esnsdgsmti tatfegatnp dtaqvqvqnk lnlatpllpq 121  evqqqgirvt kavknfllvi glvsedgsmt kddlanyivs nmqdpisrta gvgdfqvfga
```

-continued

```
 181  qyamrimldp akankfqltp vdvktavaaq nvqvssaglg glpaapgtql natilaktri
 241  qtaegfesil lkynkdgsqv rlgdvaqvgl ggenyaysaq fngkpasgla vklatganal
 301  dtakalreti kglepffppg vkavfpydtt pvvtesisgv ihtlieavvl vflvmylflq
 361  nfratiittm tvpvvllgtf gilaaagfsi ntltmfamvi aigllvddai vvvenvervm
 421  seeglppkea tkrsmegiqg alvgialvas avllpmaffa gstgviyrqf sitivsamgl
 481  svlvaliftp alcatmlkpl kkgehhtakg gffawfnrnf drsvngyers vaailrnkvp
 541  fllayalivv gmiwlfarip taflpeedgg vlfaqvqtpa gssaertgvv vdgmreyllk
 601  deadtvssvf tvngfnfagr gqssgmafim lkpwderske nsvfalagra qqhfftfrda
 661  mvfafappav lelgnatqfd vflqdrggvg heklmearnq flakaagski lsavrpnaln
 721  depqyqltid derasalgvt iadinntisi algasyvndf idrarvkkvy iqgepsarms
 781  pedlqkmyvr ngagemvpfs sfakaewtyg spklsryngv eameilgapa pgystaeama
 841  everiagelp sgigfswtgm syeeklsgsq mpalfalsvl fvflciaaly eswsipiavv
 901  lvvpigiiga liatslrgls ndvyfivgll ttiglaakna ilivefakel heggrslyda
 961  aieacrmrir piimtslafi lgvvpltias gagagsqhai gtgviggmis atvlaifwvp
1021  lffvaysslf gskepekdvt penpryeagq
```

*Marinobacter aqueolei* EPL (NCBI YP_960752), SEQ ID NO: 3

```
   1  mprffierpi fawvvalmim lggglavkni avnqfpdvap paialsvnyp gasagtvgdt
  61  vvqvieggin gldglryiss esnsdgsmti iatfeqgtdp diaqvqvqnk lgianpllpe
 121  evqrggirvs kykvnfftvf altspdgkyt qgdladyivs niqdpvartg gvgdfllfgs
 181  qyamrlwldp eklnsyqltp qdvinsvraq nvqvsagqlg glptaegvql qatvigkqrm
 241  ktaeefenil lkvnpdasqv rladvaevnl gnenyattgk ynaapaagma lrlataandl
 301  etagrvketi aelerflpeg veivfpydtt pvvsasietv amtlieavvi vfavmfifiq
 361  swratiiptl avpvvllatf gvlyafgftv nvmtmfamvi aiallvddai vvvenverlm
 421  eeeglspkea akksmdgisg allgiglvis avflpmaffg gstgviyrqf svtiisamsf
 481  svlvafiftp alcatllkpg dqhvrkgffg wfnrtfdrsa dryksgvsyl ikrkgrfmgv
 541  ylllvvavgf lfkglptafl pdedggvmiv mvqlptnatg erteavlaea gnylleeese
 601  vvksvmevrg fnfagrggns gilfvdlkpf adresfagev falagrsgar faqikdaivf
 661  pivppailel gnatgfdlyl kdngaighha lmaatnefis ranaapelnm vrhnglpdep
 721  qyqviiddek arllgvsiad inatmsaawa ssyvndflhn grvkkvyvga kpdsrlaped
 781  fdkwfvrnaq gemvpfaafa tgewvfaspr lgrygglpat qiqgapangy stgdamaale
 841  riaadlpqgl gleytglsfe ekgagngamm lyllsilvvf lclaalyesw sipfavimav
 901  plgvlgavla tmarglsndv ffgvgmlttm glaaknaili vefarqlyeq egkpllqata
 961  eaarlrlrpi imtslafifg vlpmaiasga ssasghaigt avvggtlaat ilaiffvplf
1021  yvfvvgltgk rksadd
```

*Pseudoalteromonas haloplanktis* TAC125 (NCBI YP_341810), SEQ ID NO: 4

```
   1  msryfidkpd fawvlaiivm lagilavksl piagypsiap paisitanyp gasaqtleds
  61  vtqviegkmk gldgllymss tsesngsatl tltfnadtdp diaqvgvqnk latatpllpe
 121  evqrqgvvva kaarnfllvl afvskdgsmt nidigdyvas nvgdivsrvd gvgeaglfgs
 181  gyamriwldp aklgnfkltp ndigaaitag naqvsagqlg gmpaiagggl natitagsrl
 241  qtpegfenil vktnsdgsvv rlkdvarvel ggenygvvar yngdpaagig iklasganal
```

-continued

```
 301   dtaegvkkal edlkpffpeg ldvaipydtt pfvslsiekv vhtlieavil vfvvmylflg
 361   nfratlipti avpvvllgtf ailytfgysi ntltmfamvl aigllvddai vvvenverlm
 421   teeklgaada trksmdeikg alvgiamvls avfipmaffs gstgviyrqf sitivsamgl
 481   svlvaliltp alcatllkps hvhdktsfig rffsgfnrgf dktnrgaggi vgrmisgskr
 541   yiliygvivg gmvyvfsslp taflpdedgg ilfngvmlpa gstiegtigv vekvenhyin
 601   dgaeavgsif tvtgfsfags gqnsaigfvn lkhwderqrd dlsvnavagk gmgyfstike
 661   afvfafpppa ivelgtangf nmflgdrvgl ghdellnarn mllgmasksp vlagvrpngg
 721   edmpelqldi dlakaealgv tqtdinstls tawgsryvnd fidrgrvkkv ymggeadsrm
 781   vpedlnkwyv rnnngdmvpf aafasshwsy gsprleryng fsameiqgsa apgystgqam
 841   demerlvkgl pngiasewsg isyqerssgg qapllyglsl lfvficlaal yeswsvpfav
 901   miivpigifg aimaalignl sndiylgvgl lttiglaskn ailivefaih kmeeglslvd
 961   aaiaavklrl rpvlmtslaf icgvvplaia ssagsgaqna lgisiiggtl aastlvvlfv
1021   plffvlvrkt fssksavatk ese
```

*E. coli* AcrF (SEQ ID NO: 5)

```
   1   manffirrpi fawvlaiilm magalailql pvaqyptiap pavsvsanyp aadadtvqdt
  61   vtgviegnmn gidnlmymss tsdsagsvti tltfgegtdp diaqvqvqnk lglatpllpq
 121   evqqqgisve kssssylmva gfvsdnpgtt gddisdyvas nvkdtlsrln gvgdvglfga
 181   gyamriwida dllnkykltp vdvingikvg ndgiaaggig gtpalpgggl nasiiagtrf
 241   knpeefgkvt lrvnsdasvy rlkdvarvel ggenynviar ingkpaagig iklatganal
 301   dtakaikakl aelqpffpqg mkviypydtt pfvglsihev vktlfeaiml vflvmylflg
 361   nmratlipti avpvvllgtf ailaafgysi ntltmfamvl aiallvddai vvvenvervm
 421   medkappkea teksmsqiqg alvgiamvls avfipmaffg gstgaiyrgf sitivsamal
 481   svlvaliltp alcatllkpv saehhenkgg ffgwfnttfd hsvnhytnsv gkilgstgry
 541   lliyalivag mvvlflrlps sflpeedqgv fltmlglpag atqertgkvl dqvtdyylkn
 601   ekanvesvft vnafsfsgqa qnagmafvsl kpweerngde nsaeavilyr kmelgkirdg
 661   fvipfnmpai velotatgfd felidgaglg hdaltqarng llgmaaqhpa slvsvrpnql
 721   edtaqfklev dqekagalgv slsdingtis talggtyvnd fidrgrvkkl yvqadakfrm
 781   lpedvdklyv rsangemvpf safttshwvy gsprleryng lpsmeiqgea apgtssgdam
 841   almenlaskl pagigydwtg msyqerlsgn gapalvaisf vvvflclaal yeswsipvsv
 901   mlvvplgivg vllaatlfng kndvyfmvgl lttiglsakn ailivefakd lmekegkgvv
 961   eatlmavrmr lrpilmtsla filavlplai sngagsgaqn avgigvmggm vsatllaiff
1021   vpvffvvirr cfkg
```

What is claimed is:

1. A microorganism host cell genetically modified to express a variant AcrB polypeptide, wherein the variant AcrB polypeptide has efflux pump activity, can transport 1-hexene, and comprises an amino acid sequence having at least 98% identity to SEQ ID NO:1 and at least one amino acid sequence substitution relative to SEQ ID NO:1 at a position corresponding to a position in SEQ ID NO:1 selected from the group consisting of position 279, 584, 822, 927, and 1033.

2. The host cell of claim 1, wherein the host cell is a bacterial host cell.

3. The host cell of claim 1, wherein the variant AcrB polypeptide further comprises a substitution at a position corresponding to position 617 of SEQ ID NO:1.

4. The host cell of claim 1, wherein the variant AcrB polypeptide comprises at least one substitution selected from:
- an alanine to threonine substitution at a position corresponding to position 279 of SEQ ID NO:1;
- a glutamine to arginine substitution at a position corresponding to position 584 of SEQ ID NO:1;
- a leucine to proline amino acid substitution at a position corresponding to position 822 of SEQ ID NO:1;
- a phenylalanine to serine amino acid substitution at a position corresponding to position 927 of SEQ ID NO:1; and
- a phenylalanine to tyrosine amino acid substitution at a position corresponding to position 1033 of SEQ ID NO: 1.

5. The host cell of claim 3, wherein the substitution at position 617 is a phenylalanine to leucine amino acid substitution.

6. The host cell of claim 5, wherein the host cell further comprises the proteins necessary to produce 1-hexene, or a derivative thereof.

7. A recombinant polynucleotide comprising a nucleic acid sequence encoding a variant AcrB polypeptide that has efflux pump activity and can transport 1-hexene in a host cell, wherein the variant AcrB polypeptide comprises (i) an amino acid sequence having at least 98% identity to SEQ ID NO:1; and (ii) at least one amino acid sequence substitution relative to SEQ ID NO:1 at a position corresponding to a position in SEQ ID NO:1 selected from the group consisting of position 279, 584, 822, 927, and 1033; or amino acid sequence substitutions at two or more positions corresponding to positions 279, 584, 617, 822, 927, or 1033 of SEQ ID NO:1.

8. An expression vector comprising the polynucleotide of claim 7.

9. A host cell comprising the expression vector of claim 8.

10. The host cell of claim 2, wherein the bacterial host cell is a gram negative bacterial cell.

11. The host cell of claim 10, wherein the gram negative bacterial cell is an *Escherichia coli* cell.

12. A microorganism host cell comprising a variant AcrB polypeptide that has efflux pump activity and can transport 1-hexene, wherein the variant AcrB polypeptide comprises all of SEQ ID NO:1 except for (i) one or more substitutions at positions corresponding to positions in SEQ ID NO: 1 selected from position 279, 584, 822, 927, and 1033, or (ii) two or more substitutions at positions corresponding to positions in SEQ ID NO: 1 selected from position 279, 584, 617, 822, 927, and 1033.

13. The microorganism host cell of claim 12, wherein the variant AcrB polypeptide comprises all of SEQ ID NO: 1 except for three substitutions at positions corresponding to positions in SEQ ID NO: 1 selected from position 279, 584, 617, 822, 927, and 1033.

14. The microorganism host cell of claim 12, wherein the variant AcrB polypeptide comprises at least one of the following: a threonine at a position corresponding to position 279 of SEQ ID NO:1, an arginine at a position corresponding to position 584 of SEQ ID NO:1, a proline at a position corresponding to position 822 of SEQ ID NO:1, a serine at a position corresponding to position 927 of SEQ ID NO:1, or a tyrosine at a position corresponding to position 1033 of SEQ ID NO:1, or wherein the variant AcrB polypeptide comprises at least two of the following: a threonine at a position corresponding to position 279 of SEQ ID NO:1, an arginine at a position corresponding to position 584 of SEQ ID NO:1, a leucine at a position corresponding to position 617 of SEQ ID NO: 1, a proline at a position corresponding to position 822 of SEQ ID NO:1, a serine at a position corresponding to position 927 of SEQ ID NO:1, or a tyrosine at a position corresponding to position 1033 of SEQ ID NO:1.

15. The microorganism host cell of claim 12, wherein the variant AcrB polypeptide comprises at least three of the following: a threonine at a position corresponding to position 279 of SEQ ID NO:1, an arginine at a position corresponding to position 584 of SEQ ID NO:1, a leucine at a position corresponding to position 617 of SEQ ID NO: 1, a proline at a position corresponding to position 822 of SEQ ID NO:1, a serine at a position corresponding to position 927 of SEQ ID NO:1, or a tyrosine at a position corresponding to position 1033 of SEQ ID NO:1.

16. The microorganism host cell of claim 12, wherein the microorganism host cell is a gram negative bacterial host cell.

17. The microorganism host cell of claim 16, wherein the gram negative bacterial host cell is an *E. coli* host cell.

* * * * *